United States Patent
Schwink et al.

(10) Patent No.: US 10,392,366 B2
(45) Date of Patent: Aug. 27, 2019

(54) AZETIDINE COMPOUNDS AS GPR119 MODULATORS FOR THE TREATMENT OF DIABETES, OBESITY, DYSLIPIDEMIA AND RELATED DISORDERS

(71) Applicant: SANOFI, Paris (FR)

(72) Inventors: Lothar Schwink, Frankfurt am Main (DE); Christian Buning, Frankfurt am Main (DE); Heiner Glombik, Frankfurt am Main (DE); Christoph Pöverlein, Frankfurt am Main (DE); Kurt Ritter, Frankfurt am Main (DE); Nis Halland, Frankfurt am Main (DE); Matthias Lohmann, Frankfurt am Main (DE)

(73) Assignee: SANOFI, Paris (FR)

(*) Notice: Subject to any disclaimer, the term of this patent is extended or adjusted under 35 U.S.C. 154(b) by 0 days.

(21) Appl. No.: 15/899,842

(22) Filed: Feb. 20, 2018

(65) Prior Publication Data
US 2018/0237419 A1 Aug. 23, 2018

(30) Foreign Application Priority Data

Feb. 21, 2017 (EP) .................................. 17305189

(51) Int. Cl.
| | | |
|---|---|---|
| C07D 401/12 | (2006.01) | |
| C07D 401/14 | (2006.01) | |
| C07D 403/14 | (2006.01) | |
| A61K 31/444 | (2006.01) | |
| A61K 45/06 | (2006.01) | |
| A61K 31/506 | (2006.01) | |
| A61K 31/7008 | (2006.01) | |
| C07D 417/14 | (2006.01) | |
| A61K 31/155 | (2006.01) | |
| A61K 31/351 | (2006.01) | |
| A61K 31/397 | (2006.01) | |
| C07D 487/10 | (2006.01) | |

(52) U.S. Cl.
CPC .......... *C07D 401/14* (2013.01); *A61K 31/155* (2013.01); *A61K 31/351* (2013.01); *A61K 31/397* (2013.01); *A61K 31/444* (2013.01); *A61K 31/506* (2013.01); *A61K 31/7008* (2013.01); *A61K 45/06* (2013.01); *C07D 403/14* (2013.01); *C07D 417/14* (2013.01); *C07D 487/10* (2013.01)

(58) Field of Classification Search
CPC ... C07D 401/12; C07D 401/14; C07D 403/14
See application file for complete search history.

(56) References Cited

FOREIGN PATENT DOCUMENTS

| WO | WO-2004/110994 A1 | 12/2004 |
|---|---|---|
| WO | WO-2010/048149 A2 | 4/2010 |
| WO | WO-2011/044001 A1 | 4/2011 |
| WO | WO-2011/146335 A1 | 11/2011 |
| WO | WO-2012/037393 A1 | 3/2012 |
| WO | WO-2013/070463 A2 | 5/2013 |
| WO | WO-2014/056872 A1 | 4/2014 |
| WO | WO-2014/096145 A1 | 6/2014 |
| WO | WO-2014/096148 A1 | 6/2014 |
| WO | WO-2014/096149 A1 | 6/2014 |
| WO | WO-2014/096150 A1 | 6/2014 |
| WO | WO-2015/150563 A1 | 10/2015 |
| WO | WO-2015/150564 A1 | 10/2015 |
| WO | WO-2015/150565 A1 | 10/2015 |

OTHER PUBLICATIONS

Overton, H.A. et al. (Mar. 2008). "GPR119, a Novel G Protein-Coupled Receptor Target for the Treatment of Type 2 Diabetes and Obesity," *British Journal of Pharmacology* 153(Suppl. 1):S76-S81.
Ritter, K. et al. (2016). "G Protein-Coupled Receptor 119 (GPR119) Agonists for the Treatment of Diabetes: Recent Progress and Prevailing Challenges," *Journal of Medicinal Chemistry* 59(8):3579-3592.
Rote Liste® (2016). Table of Contents, with Machine Translation in English, four pages.
Rote Liste® (2016). 56th Edition. Medicinal product list for Germany (including EU approvals and certain medicinal products). "Antiadiposita/Appetitzügler," Chapter 6, pp. 311-312, two pages (German Language).
Rote Liste® (2016). 56th Edition. Medicinal product list for Germany (including EU approvals and certain medicinal products). "Antidiabetika,"Chapter 12, pp. 390-406, seventeen pages (German Language).
Rote Liste® (2016). 56th Edition. Medicinal product list for Germany (including EU approvals and certain medicinal products). "Antihypertonika," Chapter 17, pp. 459-490, thirty two pages (German Language).
Rote Liste® (2016). 56th Edition. Medicinal product list for Germany (including EU approvals and certain medicinal products). "Diuretika," Chapter 36, pp. 711-715, five pages (German Language).
Rote Liste® (2016). 56th Edition. Medicinal product list for Germany (including EU approvals and certain medicinal products). "Lipidsenker," Chapter 58, pp. 889-898, ten pages (German Language).
Tyle, P. (1986). "Iontophoretic Devices for Drug Delivery," *Pharmaceutical Research* 3(6):318-326.
USP Dictionary (2014) of USAN and International Drug Names, the United States Pharmacopeial Convention, 12601 Twinbrook Parkway, Rockville, MD 20852, three pages.
Yang, J.W. et al. (Feb. 2018; e-published on Jul. 18, 2017). "Therapeutic Application of GPR119 Ligands in Metabolic Disorders," *Diabetes, Obesity and Metabolism* 20:257-269.
Extended European Search Report dated Apr. 20, 2017 in EP Application No. 17305189.7, seven pages.

*Primary Examiner* — Bruck Kifle
(74) *Attorney, Agent, or Firm* — Morrison & Foerster LLP

(57) ABSTRACT

The present disclosure relates to azetidine compounds. The azetidine compounds are GPR119 modulators and useful for the prevention and/or treatment of diabetes, obesity, dyslipidemia and related disorders. The present disclosure furthermore relates to the use of azetidine compounds as active ingredients in pharmaceuticals, and pharmaceutical compositions comprising them.

44 Claims, No Drawings

AZETIDINE COMPOUNDS AS GPR119 MODULATORS FOR THE TREATMENT OF DIABETES, OBESITY, DYSLIPIDEMIA AND RELATED DISORDERS

CROSS REFERENCE TO RELATED APPLICATIONS

This application claims priority benefit to EP Application No. 17305189.7, filed Feb. 21, 2017, the disclosure of which is herein incorporated by reference in its entirety.

DETAILED DESCRIPTION

The present disclosure relates to compounds of formula I

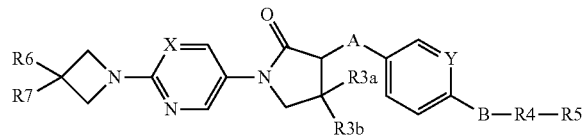

in which A, B, X, Y, R3a, R3b, R4, R5, R6 and R7 are defined as indicated below. The compounds of formula I are GPR119 modulators and useful for the prevention and/or treatment of diabetes, obesity, dyslipidemia and related disorders. The present disclosure furthermore relates to the use of compounds of the formula I as active ingredients in pharmaceuticals, and pharmaceutical compositions comprising them.

GPR119 is a G-protein coupled receptor which is expressed predominantly in the pancreas and in the K- and L-cells of the intestine. In vitro studies have shown that agonists of GPR119, via activation of the cAMP pathway in gut and pancreas derived cell lines, mediate the secretion of GLP-1 and insulin, respectively. This supports the hypothesis that modulators of GPR119, agonists in particular, may have utility to treat diabetes and related disorders by augmenting the secretion of insulin and intestinal hormones like GIP, GLP-1 and PYY. As the secretion of insulin was found to be strictly glucose-dependent, induction of hypoglycemic episodes may largely be avoided.

Furthermore, beneficial effects like reduced food intake may be expected based on the release of intestinal peptides. Stimulation of pancreatic cells by activation of GPR119 may also improve beta cell function and beta cell mass. Studies of GPR119 agonists in rodents showed the predicted glucose lowering effects. For some such animal studies, decreased food intake and weight loss was reported. Recently, clinical trials with GPR119 agonists added evidence for a positive impact on lipid parameters i.e. elevation of HDL-C together with lowering of LDL-C and triglycerides in humans. A therapeutic use of GPR119 agonists in metabolic disorders such as diabetes and obesity has been reviewed by Ritter et al. (J. Med. Chem. 59 (2016), 3579-3592), Yang et al. (Diabetes Obes. Metab. (2017), 1-13, doi: 10.1111/dom. 13062) and Overton et al. (British J. Pharmacol. 153 (2008), S76-S81), the contents of which are herein incorporated by reference in their entirety.

WO2013/070463 discloses that GPR119 agonists may be used to treat abnormalities in blood lipids. In summary, modulators of GPR119, agonists in particular, may have therapeutic utility in the prevention and/or treatment of metabolic disorders in mammals and especially in humans. Examples of such disorders and diseases include type 2 diabetes mellitus, type 1 diabetes mellitus, impaired glucose tolerance, insulin resistance, loss of beta cell function, hyperglycemia, hypercholesterolemia, dyslipidemia, hypertriglyceridemia, syndrome X, metabolic syndrome, obesity, fatty liver, steatosis, steatohepatitis, non-alcoholic steatohepatitis (NASH), cirrhosis, micro- and marcovascular disorders, high blood pressure, chronic low grade inflammation, retinopathy, neuropathy, nephropathy, atherosclerosis, coronary heart disease, endothelial dysfunction and bone-related diseases such as osteoporosis, rheumatoid arthritis or osteoarthritis.

Several modulators of GPR119 are known. For example, WO2011/146335 and WO2012/037393 describe piperidinyl-substituted lactams as GPR119 modulators. WO2010/048149 describes heterocyclic modulators of GPR119 for the treatment of disease and their preparation. WO2004/110994 describes the preparation of piperazinyl-aryloxy and piperazinyl-heteroaryloxy-N-aryl lactams as 5HT1B ligands. WO2015/150563 and WO2015/150565 describe isoindolinone derivatives as GPR119 modulators. WO2015/150564 describes fused heterocyle derivatives as GPR119 modulators.

It was an aim of the present disclosure to provide novel compounds as active ingredients in pharmaceuticals.

It was another aim of the present disclosure to provide novel compounds which will lower blood glucose in humans and which are suitable for prevention and/or treatment of diabetes, obesity, dyslipidemia or related disorders.

A further aim was to provide novel GPR119 modulators, especially agonists, which can be used therapeutically for the prevention and/or treatment of diabetes, obesity, dyslipidemia or related disorders.

Accordingly a subject of the present disclosure is a compound of formula I

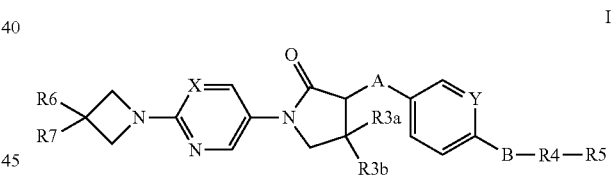

in which
X is N or C—R1;
Y is N or C—R2;
A is O or $CH_2$;
R1 is H, F or CN;
R2 is H or F;
R3a, R3b are independently of each other H or $(C_1-C_6)$-alkyl;
B is a bond, O or C=O;
R4 is a bond or $(CH_2)_p$;
p is 1 or 2;
R5 is $CF_3$, $(C_3-C_8)$-cycloalkyl, phenyl or 5- or 6-membered heteroaryl ring;
  wherein the groups $(C_3-C_8)$-cycloalkyl, phenyl and 5- or 6-membered heteroaryl ring may be optionally substituted with 1 to 3 groups selected from the list F and $(C_1-C_4)$-alkyl;
R6 is H or $(C_1-C_6)$-alkyl;
R7 is OH, $NH_2$, $(CH_2)_n$—COOR13, $(CH_2)_n$—CONR14R15, $S(O)_mR16$, NHCO—R19, O(CO)NR20R21, COR22,

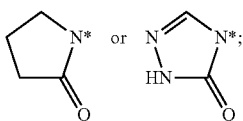

or R6 and R7, together with the carbon atom to which they are attached, form a ring of the formula L, which is spiro connected to the azetidine moiety of formula I in the position marked by the asterix;
L is

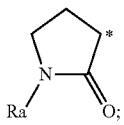

Ra is H or $(C_1-C_6)$-alkyl;
n is 0 or 1;
m is 0, 1 or 2;
R13 is H or $(C_1-C_2)$-alkyl optionally substituted with $NH_2$, $NH(C_1-C_2)$-alkyl or $N((C_1-C_2)$-alkyl$)_2$;
R14, R15 are independently of each other H, $(C_3-C_6)$-cycloalkyl, $(C_1-C_6)$-alkyl or $(C_1-C_6)$-alkyl substituted with 1 to 3 groups selected from the list $CONH_2$ and OH;
R16 is $(C_1-C_6)$-alkyl;
R19 is $(C_1-C_2)$-alkylene-O—$(C_1-C_2)$-alkyl or $(C_1-C_2)$-alkyl;
R20 is H or $(C_1-C_2)$-alkyl;
R21 is H or $(C_1-C_2)$-alkyl;
R22 is azetidinyl, pyrrolidinyl, piperidinyl or piperazinyl;
wherein the azetidinyl, pyrrolidinyl, piperidinyl or piperazinyl is optionally substituted with 1 to 3 substituents selected from the group consisting of OH and $COCH_3$;
in any of its stereoisomeric forms, or a mixture of stereoisomeric forms in any ratio, including a physiologically acceptable salt or solvate thereof.

In some embodiments,
the 3-position of the central pyrrolidinone ring depicted in formula I has (R)-configuration.

In some embodiments
A is O.

In some embodiments
A is $CH_2$.

In some embodiments
Y is CH.

In some embodiments
Y is N.

In some embodiments
X is N.

In some embodiments
X is CH.

In some embodiments
B is O.

In some embodiments
B is C=O.

In some embodiments
R3a, R3b are each H.

In some embodiments
R5 is $CF_3$.

In some embodiments
R5 is cyclopropyl.

In some embodiments
R5 is p-fluorophenyl.

In some embodiments
R7 is COOR13, CONR14R15, $SO_2$R16, S(O)R16 or OH.

In some embodiments
R7 is CONR14R15.

In some embodiments
R7 is $CON(CH_3)_2$.

In some embodiments
R7 is $SO_2$R16 or S(O)R16.

In some embodiments
R6 is H.

In some embodiments the compound of formula I is a compound of formula Ia

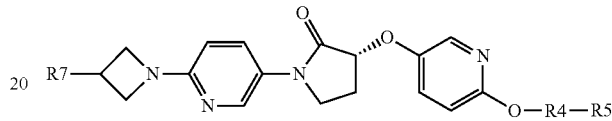

in which
R4 is $(CH_2)_p$;
p is 1 or 2;
R5 is $CF_3$ or cyclopropyl;
R7 is OH, COOR13, CONR14R15, $S(O)_m$R16 or COR22;
m is 0, 1 or 2;
R13 is H or $(C_1-C_2)$-alkyl;
R14, R15 are independently of each other H, $(C_3-C_6)$-cycloalkyl, $(C_1-C_6)$-alkyl or $(C_1-C_6)$-alkyl substituted with 1 to 3 groups selected from the list $CONH_2$ and OH;
R16 is $(C_1-C_6)$-alkyl;
R22 is azetidinyl, pyrrolidinyl, piperidinyl or piperazinyl;
wherein the azetidinyl, pyrrolidinyl, piperidinyl or piperazinyl may be optionally substituted with 1 to 3 groups selected from the list OH and $COCH_3$;
in any of its stereoisomeric forms, or a mixture of stereoisomeric forms in any ratio, including a physiologically acceptable salt or solvate thereof.

In some embodiments the compound of formula I is a compound of formula Ib

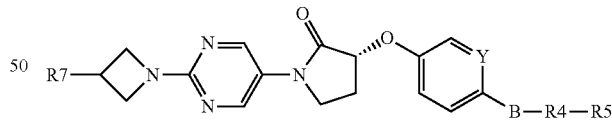

in which
Y is N or C—R2;
R2 is H or F;
B is a bond, O or C=O;
R4 is a bond or $(CH_2)_p$;
p is 1 or 2;
R5 is $CF_3$, $(C_3-C_8)$-cycloalkyl, phenyl or 5- or 6-membered heteroaryl ring;
wherein the groups $(C_3-C_8)$-cycloalkyl, phenyl and 5- or 6-membered heteroaryl ring may be optionally substituted with 1 to 3 groups selected from the list F and $(C_1-C_4)$-alkyl,
R7 is COOR13, CONR14R15, $S(O)_m$R16, COR22,

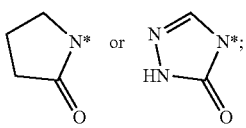

m is 0, 1 or 2;
R13 is H or ($C_1$-$C_2$)-alkyl; optionally substituted with $NH_2$, $NH(C_1$-$C_2)$-alkyl or $N((C_1$-$C_2)$-alkyl$)_2$;
R14, R15 are independently of each other H, ($C_3$-$C_6$)-cycloalkyl, ($C_1$-$C_6$)-alkyl or ($C_1$-$C_6$)-alkyl substituted with 1 to 3 groups selected from the list $CONH_2$ and OH;
R16 is ($C_1$-$C_6$)-alkyl;
R22 is azetidinyl, pyrrolidinyl, piperidinyl or piperazinyl; wherein the azetidinyl, pyrrolidinyl, piperidinyl or piperazinyl may be optionally substituted with 1 to 3 groups selected from the list OH and $COCH_3$;
in any of its stereoisomeric forms, or a mixture of stereoisomeric forms in any ratio, including a physiologically acceptable salt or solvate thereof.

In some embodiments the compound of formula I is a compound of formula Ic

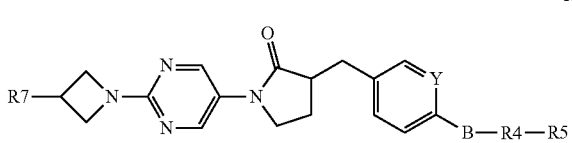

in which
Y is N or C—R2;
R2 is H or F;
B is a bond, O or C═O;
R4 is a bond or $(CH_2)_p$;
p is 1 or 2;
R5 is $CF_3$, ($C_3$-$C_8$)-cycloalkyl, phenyl or 5- or 6-membered heteroaryl ring;
wherein the groups ($C_3$-$C_8$)-cycloalkyl, phenyl and 5- or 6-membered heteroaryl ring may be optionally substituted with 1 to 3 groups selected from the list F and ($C_1$-$C_4$)-alkyl;
R7 is COOR13, CONR14R15, S(O)$_m$R16, COR22,

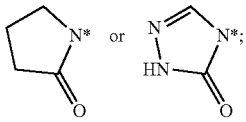

m is 0, 1 or 2;
R13 is H or ($C_1$-$C_2$)-alkyl;
R14, R15 are independently of each other H, ($C_3$-$C_6$)-cycloalkyl, ($C_1$-$C_6$)-alkyl or ($C_1$-$C_6$)-alkyl substituted with 1 to 3 groups selected from the list $CONH_2$ and OH;
R16 is ($C_1$-$C_6$)-alkyl;
R22 is azetidinyl, pyrrolidinyl, piperidinyl or piperazinyl; wherein the azetidinyl, pyrrolidinyl, piperidinyl or piperazinyl may be optionally substituted with 1 to 3 groups selected from the list OH and $COCH_3$;
in any of its stereoisomeric forms, or a mixture of stereoisomeric forms in any ratio, including a physiologically acceptable salt or solvate thereof.

In another embodiment, the compound of formula I is selected from the group consisting of compounds 1-01 to 1-54, 2-01 to 2-11, 3-01 to 3-04, 4-01 to 4-27 and 5-01 to 5-05, in any stereoisomeric form, including a physiologically acceptable salt or solvate thereof.

In another embodiment, the compound of formula I is selected from the group consisting of compounds 1-06, 1-10, 4-25 and 4-26, in any stereoisomeric form, including a physiologically acceptable salt or solvate thereof.

In another embodiment, the compound of formula I is selected from the group consisting of compounds 1-12, 1-16, 1-17, 1-37, 4-15 and 4-22, in any stereoisomeric form, including a physiologically acceptable salt or solvate thereof.

In another embodiment, the compound of formula I is selected from the group consisting of compounds 1-42 and 1-43, in any stereoisomeric form, including a physiologically acceptable salt or solvate thereof.

In another embodiment, the compound of formula I is selected from the group consisting of compounds 5-04 and 5-05, in any stereoisomeric form, including a physiologically acceptable salt or solvate thereof.

In some embodiments, the compounds of formula I are GPR119 agonists having an $EC_{50}$ from about 50 μM or less, from about 0.001 to about 10 μM, from about 0.001 to about 5 μM, from about 0.001 to about 1 μM, or from about 0.001 to about 0.3 μM in an in vitro cellular assay measuring GPR119-mediated cAMP release as described herein. Structural elements such as groups, substituents, hetero ring members, numbers or other features, for example alkyl groups, which can occur more than one time in the compounds of the formula I, can all independently of one another have at each occurrence any of the indicated meanings and can in each case be identical to or different from one another. For example, the alkyl groups in a dialkylamino group can be identical or different. It is understood that where a group is indicated to be optionally substituted, the disclosure includes embodiments in which the group is unsubstituted as well as embodiments in which the group is substituted.

Herein, the terms "including" and "comprising" are used in their open, non-limiting sense. As used herein, the terms "($C_1$-$C_6$)", "($C_3$-$C_6$)", "($C_1$-$C_4$)", "($C_1$-$C_2$)", etc. refer to moieties having 1 to 6 carbon atoms, 3 to 6 carbon atoms, 1 to 4 carbon atoms, 1 to 2 carbon atoms, etc., respectively.

The term "alkyl", as used herein, refers to saturated, monovalent hydrocarbon radicals. The term "alkenyl", as used herein, refers to monovalent hydrocarbon radicals, which contain at least one carbon-carbon double bond, wherein each double bond can have E- or Z-configuration. The term "alkynyl", as used herein, refers to monovalent hydrocarbon radicals, which contain at least one carbon-carbon triple bond. The alkyl, alkenyl and alkynyl groups can be linear, i.e. straight-chain, or branched. This also applies when they are part of other groups, for example alkyloxy groups (i.e., alkoxy groups, O-alkyl groups), alkyloxycarbonyl groups or alkyl-substituted amino groups, or when they are substituted. Depending on the respective definition, the number of carbon atoms in an alkyl group can be 1, 2, 3, 4, 5 or 6, or 1, 2, 3, or 4. Examples of alkyl are methyl, ethyl, propyl (including n-propyl and isopropyl), butyl (including n-butyl, sec-butyl, isobutyl and tert-butyl), pentyl (including n-pentyl, 1-methylbutyl, isopentyl, neopentyl and tert-pentyl), hexyl (including n-hexyl, 3,3-dimethylbutyl and isohexyl). Double bonds and triple bonds in alkenyl groups and alkynyl groups respectively can be present in any positions. Examples of alkenyl and alkynyl are ethenyl, prop-1-enyl, prop-2-enyl (=allyl), but-2-enyl, 2-methylprop-2-enyl, 3-methylbut-2-enyl, hex-3-enyl, hex-4-enyl, prop-2-ynyl (=propargyl), but-2-ynyl, but-3-ynyl, hex-4-ynyl or hex-5-ynyl. Substituted alkyl groups, alkenyl groups and alkynyl groups can be substituted at any position, provided that the respective compound is sufficiently stable and is suitable for the desired purpose, such as use as a drug substance. The requirement that a specific group and a compound of the formula I are sufficiently stable and suitable for the desired purpose, such as use as a drug substance, applies in general with respect to the definitions of all groups in the compounds of formula I.

Independently of one another and independently of any other substituents, alkyl groups, divalent alkyl groups, alkenyl groups, alkynyl groups, cycloalkyl groups and heterocycloalkyl groups are optionally substituted by one or more fluorine substituents which can be located at any position, i.e., the said groups can be unsubstituted by fluorine substituents or substituted by fluorine substituents, for example by 1, 2 or 3, by 1 or 2, or by 1 fluorine substituents. Examples of fluorine-substituted said groups are trifluoromethyl, difluoromethyl and fluoromethyl.

Deuterium (D or $^2$H) is a stable, non-radioactive isotope of hydrogen. Independently of one another and independently of any other substituents, one or more hydrogen atoms in the alkyl groups, divalent alkyl groups, alkenyl groups, alkynyl groups, cycloalkyl groups and heterocycloalkyl groups may be replaced by deuterium.

The term "alkanediyl" or "alkylene", as used herein, refers to saturated, divalent hydrocarbon radicals. The term "alkenediyl", as used herein, refers to divalent hydrocarbon radicals, which contain at least one carbon-carbon double bond, wherein each double bond can have E- or Z-configuration. The term "alkynediyl", as used herein, refers to divalent hydrocarbon radicals, which contain at least one carbon-carbon triple bond. The preceding explanations regarding alkyl, alkenyl and alkynyl groups apply as well to alkanediyl, alkenediyl and alkynediyl groups, which can likewise be linear and branched. Examples of divalent alkyl groups are —CH$_2$— (i.e., methylene), —CH$_2$—CH$_2$—, —CH$_2$—CH$_2$—CH$_2$—, —CH$_2$—CH$_2$—CH$_2$—CH$_2$—, —CH(CH$_3$)—, —C(CH$_3$)$_2$—, —CH(CH$_3$)—CH$_2$—, —CH$_2$—CH(CH$_3$)—, —C(CH$_3$)$_2$—CH$_2$— and —CH$_2$—C(CH$_3$)$_2$—.

The term "cycloalkyl", as used herein, unless otherwise indicated, refers to a mono-valent radical of a saturated hydrocarbon ring system, which is monocyclic. In a monocyclic cycloalkyl group, the number of ring carbon atoms can be, for example, 3, 4, 5, 6, 7 or 8. In one embodiment, the number of ring carbon atoms in a cycloalkyl group, independently of the number of ring carbon atoms in any other cycloalkyl group, is 3, 4, 5 or 6. In another embodiment, the number of ring carbon atoms in a cycloalkyl group is 3 or 4. In another embodiment, the number of ring carbon atoms in a cycloalkyl group is 3. In another embodiment, the number of ring carbon atoms in a cycloalkyl group is 5 or 6. In another embodiment, the number of ring carbon atoms in a cycloalkyl group is 5. In another embodiment, the number of ring carbon atoms in a cycloalkyl group is 6. Examples of cycloalkyl groups are cyclopropyl, cyclobutyl, cyclopentyl and cyclohexyl.

The term "heterocycle", as used herein, unless otherwise indicated, refers to a cycloalkyl as defined above, in which 1, 2, 3 or 4 carbon atoms are replaced by nitrogen or oxygen atoms, provided that the heterocycloalkyl system is stable and suitable as a subgroup for the desired purpose of the compound of formula I, such as use as a drug substance.

Depending on the definition of the respective heterocyclic group, in one embodiment, the number of ring heteroatoms which can be present in a heterocyclic group, independently of the number of ring heteroatoms in any other heterocyclic group, is 1 or 2, wherein the ring heteroatoms are identical or different. In another embodiment, the number of ring heteroatoms is 2. In another embodiment, the number of ring heteroatoms is 1. The heterocycloalkyl group can be attached by any ring carbon atom or saturated ring nitrogen atom, with the exception of spiro- or bridgehead atoms.

Exemplary monocyclic heterocycloalkyl groups are derived from, but not limited to, the ring systems azetidine, oxetane, pyrrolidine, tetrahydrofuran, 1,3-dioxolane, piperidine, piperazine, morpholine, tetrahydropyran or 1,4-dioxane:

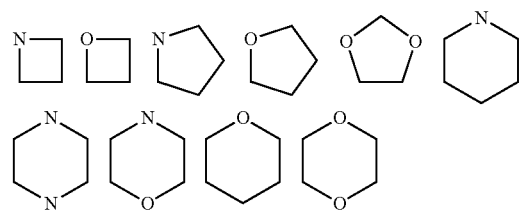

In one embodiment monocyclic heterocycloalkyl groups are derived from azetidine, pyrrolidine, piperidine, piperazine or morpholine:

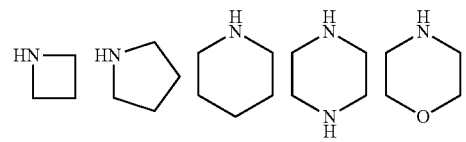

The term "aryl", as used herein, refers to a radical derived from an aromatic hydro-carbon by removal of one hydrogen, such as phenyl.

The term "heteroaryl" as used herein, refers to a radical derived from a fully unsaturated monocyclic ring system, in which 1, 2 or 3 carbon atoms are replaced by heteroatoms. The ring heteroatoms are generally chosen from N, O and S, wherein N includes ring nitrogen atoms which carry a hydrogen atom or a substituent as well as ring nitrogen atoms which do not carry a hydrogen atom or a substituent. Ring heteroatoms can be located in any position, provided that the heterocyclic system is stable and suitable as a subgroup for the desired purpose of the compound of formula I, such as use as a drug substance. Heteroaryl radicals are derived from 5-membered or 6-membered monocyclic rings.

Exemplary heteroaryl systems are derived from, but not limited to, the following ring systems: pyrrole, furan, thiophene, imidazole, pyrazole, oxazole (=[1,3]oxazole), isoxazole (=[1,2]oxazole), thiazole (=[1,3]thiazole), isothiazole (=[1,2]thiazole), [1,2,3]triazole, [1,2,4]triazole, [1,2,4]oxadiazole, [1,3,4]oxadiazole, [1,2,4]thiadiazole, [1,3,4]thiadiazole, pyridine, pyridazine, pyrimidine, pyrazine, [1,2,3]triazine, [1.2.4]triazine or [1.3.5]triazine:

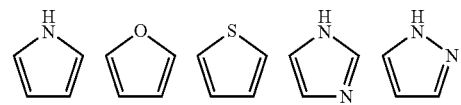

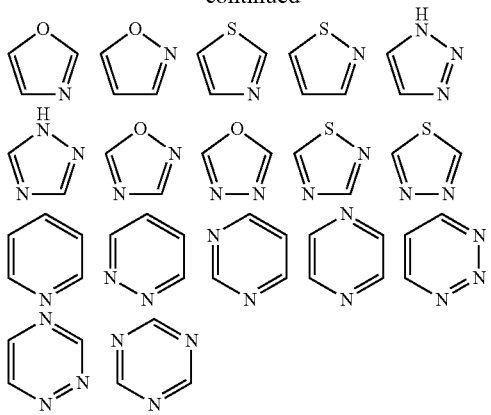

Groups like phenyl and residues of aromatic heterocycles which are optionally substituted by one or more substituents, can be unsubstituted or substituted, for example by 1, 2 or 3, or by 1 or 2, or by 1, identical or different substituents which can be located in any position. Aromatic nitrogen heterocycles which in the parent ring system carry a hydrogen atom on a ring nitrogen atom in a 5-membered ring, such as a pyrrole or imidazole ring, for example, can be substituted on ring carbon atoms and/or on such ring nitrogen atoms. In one embodiment of the present disclosure, substituents on such ring nitrogen atoms are chosen from $(C_1-C_4)$-alkyl groups, i.e. such ring nitrogen atoms in aromatic heterocycles carry a hydrogen atom or a $(C_1-C_4)$-alkyl substituent. When it is stated with respect to ring nitrogen atoms in aromatic heterocycles and any other heterocycles that they can carry a hydrogen atom or a substituent, such ring nitrogen atoms either carry a hydrogen atom or a substituent or they do not carry a hydrogen atom or substituent. Ring nitrogen atoms which carry a hydrogen atom or a substituent occur in a nitrogen-containing aromatic 5-membered ring as is present, for example, in pyrrole or imidazole, and in a non-aromatic ring including a saturated ring. Ring nitrogen atoms which do not carry a hydrogen atom or a substituent unless they are present in positively charged form, including any further ring nitrogen atoms in addition to ring nitrogen atoms which carry a hydrogen atom or a substituent, occur in an aromatic ring as is present in thiazole, imidazole or pyridine, for example, and in a non-aromatic ring in which they are part of a double bond, and they occur as ring nitrogen atoms via which a ring is bonded. Suitable ring nitrogen atoms in aromatic heterocycles in the compounds of the formula I, such as the ring nitrogen atom in a pyridine ring, can in general also be present as an N-oxide or as a quaternary salt, for example as an N—$(C_1-C_4)$-alkyl salt such as N-methyl salt, wherein in one embodiment of the present disclosure the counter anion in such quaternary salt is a physiologically acceptable anion which is derived from an acid that forms a physiologically acceptable salt.

In monosubstituted phenyl groups, the substituent can be located in the 2-position, the 3-position or the 4-position. In disubstituted phenyl groups, the substituents can be located in 2,3-position, 2,4-position, 2,5-position, 2,6-position, 3,4-position or 3,5-position. In trisubstituted phenyl groups, the substituents can be located in 2,3,4-position, 2,3,5-position, 2,3,6-position, 2,4,5-position, 2,4,6-position or 3,4,5-position.

Ring heteroatoms can be located in any positions, provided that the heterocyclic system is known in the art and is stable and suitable as a subgroup for the desired purpose of the compound of formula I, such as use as a drug substance. In one embodiment of the present disclosure, two ring oxygen atoms cannot be present in adjacent ring positions of any heterocycle. In another embodiment, two ring heteroatoms selected from the group consisting of oxygen and sulfur cannot be present in adjacent ring positions of any heterocycle. Substituents on heterocyclic groups can be located in any positions. For example, in a pyridin-2-yl group, substituents can be located in the 3-position and/or 4-position and/or 5-position and/or 6-position. Similarly, in a pyridin-3-yl group, substituents can be located in the 2-position and/or 4-position and/or 5-position and/or 6-position. Likewise, in a pyridin-4-yl group, substituents can be located in the 2-position and/or 3-position and/or 5-position and/or 6-position.

When an oxo group is bonded to a carbon atom, it replaces two hydrogen atoms on a carbon atom of the parent system. Thus, if a $CH_2$ group in a chain or a ring is substituted by oxo, i.e. by a doubly bonded oxygen atom, it becomes a CO group. As will be understood by a skilled artisan, an oxo group cannot occur as a substituent on a carbon atom in an aromatic ring, e.g. an aryl or heteroaryl ring, such as in a phenyl group, for example.

The present disclosure includes all stereoisomeric forms of the compounds of formula I and their salts and solvates. With respect to each chiral center, independently of any other chiral center, the compounds of formula I can be present in S configuration or substantially S configuration, or in R configuration or substantially R configuration, or as a mixture of the S isomer and the R isomer in any ratio. The present disclosure includes all possible enantiomers and diastereomers and mixtures of two or more stereoisomers, for example mixtures of enantiomers and/or diastereomers, in all ratios. Thus, compounds according to the present disclosure which can exist as enantiomers can be present in enantiomerically pure form, both as levorotatory and as dextrorotatory antipodes, and in the form of mixtures of the two enantiomers in all ratios including racemates. In the case of a E/Z isomerism, or cis/trans isomerism, for example on double bonds or rings such as cycloalkyl rings, the present disclosure includes both the E form and Z form, or the cis form and the trans form, as well as mixtures of these forms in all ratios. In one embodiment of the present disclosure, a compound which can occur in two or more stereoisomeric forms is a pure, or substantially pure, individual stereoisomer. The preparation of individual stereoisomers can be carried out, for example, by separation of a mixture of isomers by customary methods, for example by chromatography or crystallization, by the use of stereochemically uniform starting materials in the synthesis, or by stereoselective synthesis. Optionally, a derivatization can be carried out before a separation of stereoisomers. The separation of a mixture of stereoisomers can be carried out at the stage of the compound of formula I or at the stage of a starting material or an intermediate during the synthesis. The present disclosure also includes all tautomeric forms of the compounds of formula I and their salts and solvates.

In embodiments where certain of the compounds of formula I contain one or more acidic and/or basic groups, i.e. salt-forming groups, the present disclosure also includes their corresponding physiologically or toxicologically acceptable salts, i.e. non-toxic salts, in particular their pharmaceutically acceptable salts.

The present disclosure furthermore includes all solvates of compounds of formula I, for example hydrates or adducts with alcohols such as $(C_1-C_4)$-alkanols, active metabolites of the compounds of formula I, and also prodrugs and derivatives of the compounds of formula I, which in vitro may not necessarily exhibit pharmacological activity but which in vivo are converted into pharmacologically active compounds, for example esters or amides of carboxylic acid groups.

One or more compounds of the present disclosure can be combined with one or more other pharmacologically active compounds, such as all drugs mentioned in the Rote Liste 2016, e.g. all antidiabetics mentioned in the Rote Liste 2016, chapter 12, all weight-reducing agents or appetite suppressants mentioned in the Rote Liste 2016, chapter 06, all lipid-lowering agents mentioned in the Rote Liste 2016, chapter 58, all antihypertensives mentioned in the Rote Liste 2016 chapter 17, and all diuretics mentioned in the Rote Liste 2016, chapter 36.

The active ingredient combinations can be applied either by separate administration of the active ingredients to the patient or in the form of combination products in which a plurality of active ingredients are present in one pharmaceutical preparation. When administered separately, administration may occur simultaneously or sequentially, in any order. The amount of the compound of the present disclosure and the other pharmaceutically active ingredient(s) and the relative timings of administration will be selected in order to achieve the desired combined therapeutic effect. The administration of the combination may be concomitantly in: (1) a unitary pharmaceutical composition including all pharmaceutically active ingredients; or (2) separate pharmaceutical compositions each including at least one of the pharmaceutically active ingredients. Alternatively, the combination may be administered separately in a sequential manner wherein one treatment agent is administered first and the other treatment agent is administered second, or vice versa. Such sequential administration may be close in time or remote in time.

Most of the active ingredients mentioned hereinafter are disclosed in the USP Dictionary of USAN and International Drug Names, US Pharmacopeia, Rockville 2014.

Other active ingredients which are suitable for such combinations with compounds of the present disclosure include those which, for example, potentiate the therapeutic effect of compounds of the present disclosure or which may allow that the dosage of the compounds of the present disclosure is reduced.

Therapeutic agents which are suitable for combinations include, for example, antidiabetic agents such as:

Insulin and insulin derivatives, for example: insulin glargine (e.g. Lantus®), higher than 100 U/mL concentrated insulin glargine, e.g. 270-330 U/mL of insulin glargine or 300 U/mL of insulin glargine (e.g. Toujeo®), insulin glulisine (e.g. Apidra®), insulin detemir (e.g. Levemir®), insulin lispro (e.g. Humalog®, Liprolog®), insulin degludec (e.g. DegludecPlus®, IdegLira (NN9068)), insulin aspart and aspart formulations (e.g. NovoLog®), basal insulin and analogues (e.g. LY2605541, LY2963016, NN1436), PEGylated insulin lispro (e.g. LY-275585), long-acting insulins (e.g. NN1436, Insumera (PE0139), AB-101, AB-102, Sensulin LLC), intermediate-acting insulins (e.g. Humulin®N, Novolin®N), fast-acting and short-acting insulins (e.g. Humulin®R, Novolin®R, Linjeta®(VIAject®), PH20 insulin, NN1218, HinsBet®, premixed insulins, SuliXen®, NN1045, insulin plus Symlin®, PE-0139, ACP-002 hydrogel insulin, and oral, inhalable, transdermal and buccal or sublingual insulins (e.g. Exubera®, Nasulin®, Afrezza®, insulin tregopil, TPM-02 insulin, Capsulin®, Oral-lyn®, Cobalamin® oral insulin, ORMD-0801, Oshadi oral insulin, NN1953, NN1954, NN1956, VIAtab®). Also suitable are those insulin derivatives which are bonded to albumin or another protein by a bifunctional linker.

Glucagon-like-peptide 1 (GLP-1), GLP-1 analogues, and GLP-1 receptor agonists, for example: lixisenatide (e.g. Lyxumia®), exenatide (e.g. exendin-4, rExendin-4, Byetta®, Bydureon®, exenatide NexP), liraglutide (e.g. Victoza®), semaglutide, taspoglutide, albiglutide, dulaglutide, ACP-003, CJC-1134-PC, GSK-2374697, PB-1023, TTP-054, langlenatide (HM-11260C), efpeglenatide, CM-3, GLP-1 Eligen, AB-201, ORMD-0901, NN9924, NN9926, NN9927, Nodexen, Viador-GLP-1, CVX-096, ZYOG-1, ZYD-1, ZP-3022, CAM-2036, DA-3091, DA-15864, ARI-2651, ARI-2255, exenatide-XTEN (VRS-859), exenatide-XTEN+Glucagon-XTEN (VRS-859+AMX-808) and polymer-bound GLP-1 and GLP-1 analogues.

Dual GLP-1/GIP agonists (e.g. RG-7697 (MAR-701), MAR-709 (NN9709), BHM081, BHM089, BHM098, LY3298176, LBT-6030, ZP-I-70) or compounds disclosed in WO2014/096145, WO2014/096148, WO2014/096149 and WO2014/096150, herein incorporated by reference in its entirety.

Dual GLP-1/glucagon receptor agonists (e.g. BHM-034, OAP-189 (PF-05212389, TKS-1225), TT-401/402, ZP2929, LAPS-HMOXM25, MOD-6030, SAR425899) or compounds disclosed in WO2014/056872, herein incorporated by reference in its entirety.

Triple GLP-1/glucagon/GIP receptor agonists (e.g. Triagonist 1706 (NN9423), HM15211).

Dual GLP-1R agonist/Proprotein convertase subtilisin/kexin type 9 (e.g. MEDI-4166).

Dual GLP-1/GLP-2 receptor agonists (e.g. ZP-GG-72).

Dual GLP-1/gastrin agonists (e.g. ZP-3022).

Other Suitable Combination Partners are:

Further gastrointestinal peptides such as peptide YY 3-36 (PYY3-36) or analogues thereof and pancreatic polypeptide (PP) or analogues thereof (e.g. PYY 1562 (NN9747/NN9748).

Calcitonin and calcitonin analogs, amylin and amylin analogues (e.g. pramlintide, Symlin®), dual calcitonin and amylin receptor agonists such as Salmon Calcitonin (e.g. Miacalcic®), davalintide (AC2307), mimlyin, AM833 (NN9838), KBP-042, KBP-088, elcatonin.

Glucagon-like-peptide 2 (GLP-2), GLP-2 analogues, and GLP-2 receptor agonists, for example: teduglutide (e.g. Gattex®), elsiglutide, glepaglutide, FE-203799, HM15910.

Glucagon receptor agonists (e.g. G530S (NN9030), dasiglucagon, HM15136) or antagonists, glucose-dependent insulinotropic polypeptide (GIP) receptor agonists (e.g. ZP-I-98, AC163794) or antagonists (e.g. GIP(3-30)NH2), ghrelin antagonists or inverse agonists, xenin and analogues thereof.

Human fibroblast growth factor 21 (FGF21) and derivatives or analogues such as LY2405319 and NN9499 or other variants of FGF21.

Dipeptidyl peptidase-IV (DPP-4) inhibitors, for example: alogliptin (e.g. Nesina®, Kazano®), linagliptin (e.g. Ondero®, Trajenta®, Tradjenta®, Trayenta®), saxagliptin (e.g. Onglyze®, Komboglyze XR®), sitagliptin (e.g. Januvia®, Xelevia®, Tesavel®, Janumet®, Velmetia®, Juvisync®, Janumet XR®), anagliptin, teneligliptin (e.g. Tenelia®), trelagliptin, vildagliptin (e.g. Galvus®, Galvumet®), gemigliptin, omarigliptin, evogliptin, dutogliptin, DA-1229, MK-3102, KM-223, KRP-104, PBL-1427, Pinoxacin hydrochloride, and Ari-2243.

Sodium-dependent glucose transporter 2 (SGLT-2) inhibitors, for example: canagliflozin, dapagliflozin, remogliflozin, remogliflozin etabonate, sergliflozin, empagliflozin, ipragliflozin, tofogliflozin, luseogliflozin, ertugliflozin, EGT-0001442, LIK-066, SBM-TFC-039, and KGA-3235 (DSP-3235).

Dual inhibitors of SGLT-1 and SGLT-2 (e.g. sotagliflozin, LX-4211, LIK066).

SGLT-1 inhibitors (e.g. LX-2761, KGA-3235) or SGLT-1 inhibitors in combination with anti-obesity drugs such as ileal bile acid transfer (IBAT) inhibitors (e.g. GSK-1614235 and GSK-2330672).

Biguanides (e.g. metformin, buformin, phenformin).

Thiazolidinediones (e.g. pioglitazone, rosiglitazone), glitazone analogues (e.g. lobeglitazone).

Peroxisome proliferator-activated receptors (PPAR-)(alpha, gamma or alpha/gamma) agonists or modulators (e.g. saroglitazar (e.g. Lipaglyn®), GFT-505), or PPAR gamma partial agonists (e.g. Int-131).

Sulfonylureas (e.g. tolbutamide, glibenclamide, glimepiride (e.g. Amaryl®), glipizide) and meglitinides (e.g. nateglinide, repaglinide, mitiglinide).

Alpha-glucosidase inhibitors (e.g. acarbose, miglitol, voglibose).

G-protein coupled receptor 119 (GPR119) agonists (e.g. GSK-1292263, PSN-821, MBX-2982, APD-597, ARRY-981, ZYG-19, DS-8500, HM-47000, YH-Chem1, YH18421, DA-1241).

GPR40 agonists (e.g. TUG-424, P-1736, P-11187, JTT-851, GW9508, CNX-011-67, AM-1638, AM-5262).

GPR120 agonists and GPR142 agonists.

Systemic or low-absorbable TGR5 (GPBAR1=G-protein-coupled bile acid receptor 1) agonists (e.g. INT-777, XL-475, SB756050).

Other Suitable Combination Partners are:

Diabetes immunotherapeutics, for example: oral C-C chemokine receptor type 2 (CCR-2) antagonists (e.g. CCX-140, JNJ-41443532), interleukin 1 beta (IL-1ß) antagonists (e.g. AC-201), or oral monoclonal antibodies (MoA) (e.g. methalozamide, VVP808, PAZ-320, P-1736, PF-05175157, PF-04937319).

Anti-inflammatory agents for the treatment of the metabolic syndrome and diabetes, for example: nuclear factor kappa B inhibitors (e.g. Triolex®).

Adenosine monophosphate-activated protein kinase (AMPK) stimulants, for example: Imeglimin (PXL-008), Debio-0930 (MT-63-78), R-118.

Inhibitors of 11-beta-hydroxysteroid dehydrogenase 1 (11-beta-HSD-1) (e.g. LY2523199, BMS770767, RG-4929, BMS816336, AZD-8329, HSD-016, BI-135585).

Activators of glucokinase (e.g. PF-04991532, TTP-399 (GK1-399), GKM-001 (ADV-1002401), ARRY-403 (AMG-151), TAK-329, TMG-123, ZYGK1).

Inhibitors of diacylglycerol O-acyltransferase (DGAT) (e.g. pradigastat (LCQ-908)), inhibitors of protein tyrosine phosphatase 1 (e.g. trodusquemine), inhibitors of glucose-6-phosphatase, inhibitors of fructose-1,6-bisphosphatase, inhibitors of glycogen phosphorylase, inhibitors of phosphoenol pyruvate carboxykinase, inhibitors of glycogen synthase kinase, inhibitors of pyruvate dehydrogenase kinase.

Modulators of glucose transporter-4, somatostatin receptor 3 agonists (e.g. MK-4256).

One or more lipid lowering agents are also suitable as combination partners, for example: 3-hydroxy-3-methylglutaryl-coenzym-A-reductase (HMG-CoA-reductase) inhibitors such as simvastatin (e.g. Zocor®, Inegy®, Simcor®), atorvastatin (e.g. Sortis®, Caduet®), rosuvastatin (e.g. Crestor®), pravastatin (e.g. Lipostat®, Selipran®), fluvastatin (e.g. Lescol®), pitavastatin (e.g. Livazo®, Liva®), lovastatin (e.g. Mevacor®, Advicor®), mevastatin (e.g. Compactin®), rivastatin, cerivastatin (e.g. Lipobay®), fibrates such as bezafibrate (e.g. Cedur® retard), ciprofibrate (e.g. Hyperlipen®), fenofibrate (e.g. Antara®, Lipofen®, Lipanthyl®), gemfibrozil (e.g. Lopid®, Gevilon®), etofibrate, simfibrate, ronifibrate, clinofibrate, pemafibrate, clofibrate, clofibride, nicotinic acid and derivatives thereof (e.g. niacin, including slow release formulations of niacin), nicotinic acid receptor 1 agonists (e.g. GSK-256073), PPAR-delta agonists, acetyl-CoA-acetyltransferase (ACAT) inhibitors (e.g. avasimibe), cholesterol absorption inhibitors (e.g. ezetimibe, Ezetrol®, Zetia®, Liptruzet®, Vytorin®, S-556971), bile acid-binding substances (e.g. cholestyramine, colesevelam), ileal bile acid transport (IBAT) inhibitors (e.g. GSK-2330672, LUM-002), microsomal triglyceride transfer protein (MTP) inhibitors (e.g. lomitapide (AEGR-733), SLx-4090, granotapide), modulators of proprotein convertase subtilisin/kexin type 9 (PCSK9) (e.g. alirocumab (e.g. Praluent®), evolocumab (e.g. Repatha®), LGT-209, PF-04950615, MPSK3169A, LY3015014, ALD-306, ALN-PCS, BMS-962476, SPC5001, ISIS-394814, 1620, LGT-210, 1D05, BMS-PCSK9Rx-2, SX-PCK9, RG7652), LDL receptor up-regulators, for example liver selective thyroid hormone receptor beta agonists (e.g. eprotirome (KB-2115), M607811, sobetirome (QRX-431), VIA-3196, ZYT1), HDL-raising compounds such as: cholesteryl ester transfer protein (CETP) inhibitors (e.g. anacetrapib (MK0859), dalcetrapib, evacetrapib, JTT-302, DRL-17822, TA-8995, R-1658, LY-2484595, DS-1442), or dual CETP/PCSK9 inhibitors (e.g. K-312), ATP-binding cassette (ABC1) regulators, lipid metabolism modulators (e.g. BMS-823778, TAP-301, DRL-21994, DRL-21995), phospholipase A2 (PLA2) inhibitors (e.g. darapladib, Tyrisa®, varespladib, rilapladib), ApoA-I enhancers (e.g. RVX-208, CER-001, MDCO-216, CSL-112), cholesterol synthesis inhibitors (e.g. ETC-1002), lipid metabolism modulators (e.g. BMS-823778, TAP-301, DRL-21994, DRL-21995) and omega-3 fatty acids and derivatives thereof (e.g. icosapent ethyl (AMR101), Epanova®, Lovaza®, Vascepa®, AKR-063, NKPL-66, PRC-4016, CAT-2003).

Other suitable combination partners are one or more active substances for the treatment of obesity, such as for example:

Bromocriptine (e.g. Cycloset®, Parlodel®), phentermine and phentermine formulations or combinations (e.g. Adipex-P, Ionamin, Qsymia®), benzphetamine (e.g. Didrex®), diethylpropion (e.g. Tenuate®), phendimetrazin (e.g. Adipost®, Bontril®), bupropion and combinations (e.g. Zyban®, Wellbutrin XL®, Contrave®, Empatic®), sibutramine (e.g. Reductil®, Mende®), topiramat (e.g. Topamax®), zonisamid (e.g. Zonegran®), tesofensine, opioid antagonists such as naltrexone (e.g. Naltrexin®, naltrexone and bupropion), cannabinoid receptor 1 (CB1) antagonists (e.g. TM-38837), melanin-concentrating hormone (MCH-1) antagonists (e.g. BMS-830216, ALB-127158(a)), MC4 receptor agonists and partial agonists (e.g. AZD-2820, RM-493), neuropeptide Y5 (NPY5) or NPY2 antagonists (e.g. velneperit, S-234462), NPY4 agonists (e.g. PP-1420), beta-3-adrenergic receptor agonists, leptin or leptin mimetics, agonists of the 5-hydroxytryptamine 2c (5HT2c) receptor (e.g. lorcaserin, Belviq®), pramlintide/meterleptin, lipase inhibitors such as cetilistat (e.g. Cametor®), orlistat (e.g. Xenical®, Calobalin®), angiogenesis inhibitors (e.g. ALS-L1023), betahistidin and histamine H3 antagonists (e.g. HPP-404), AgRP (agouti related protein) inhibitors (e.g. TTP-435), serotonin re-uptake inhibitors such as fluoxetine (e.g. Fluctine®), duloxetine (e.g. Cymbalta®), dual or triple monoamine uptake inhibitors (dopamine, norepinephrine and serotonin re-uptake) such as sertraline (e.g. Zoloft®), tesofensine, methionine aminopeptidase 2 (MetAP2) inhibitors (e.g. beloranib), and antisense oligonucleotides against production of fibroblast growth factor receptor 4 (FGFR4) (e.g. ISIS-FGFR4Rx) or prohibitin targeting peptide-1 (e.g. Adipotide®).

Other suitable combination partners are one or more active substances for the treatment of fatty liver diseases including non-alcoholic fatty liver disease (NAFLD) and non-alcoholic steatohepatitis (NASH), such as for example:

Insulin sensitizers (e.g. rosiglitazone, pioglitazone), other PPAR modulators (e.g. elafibranor, saroglitazar, IVA-337), FXR agonists (e.g. obethicolic acid (INT-747), GS-9674, LJN-452, EDP-305), FGF19 analogues (e.g. NGM-282), FGF21 analogues (PF-05231023), GLP-1 analogues (e.g. liraglutide), SCD1 inhibitors (e.g. aramchol), anti-inflammatory compounds (e.g. CCR2/CCR5 antagonist cenicriviroc, pentamidine VLX-103), compounds reducing oxidative stress (e.g. ASK1 inhibitor GS-4997, VAP-1 inhibitor PXS-4728A), caspase inhibitors (e.g. emricasan), LOXL2 inhibitors (e.g. simtuzumab), galectin-3 protein inhibitors (e.g. GR-MD-02).

Moreover, combinations with drugs for influencing high blood pressure, chronic heart failure or atherosclerosis, for example: nitric oxide donors, AT1 antagonists or angiotensin II (AT2) receptor antagonists such as telmisartan (e.g. Kinzal®, Micardis®), candesartan (e.g. Atacand®, Blopress®), valsartan (e.g. Diovan®, Co-Diovan®), losartan (e.g. Cosaar®), eprosartan (e.g. Teveten®), irbesartan (e.g. Aprovel®, CoAprovel®), olmesartan (e.g. Votum®, Olmetec®), tasosartan, azilsartan (e.g. Edarbi®), dual angiotensin receptor blockers (dual ARBs), angiotensin converting enzyme (ACE) inhibitors, ACE-2 activators, renin inhibitors, prorenin inhibitors, endothelin converting enzyme (ECE) inhibitors, endothelin receptor (ET1/ETA) blockers, endothelin antagonists, diuretics, aldosterone antagonists, aldosterone synthase inhibitors, alpha-blockers, antagonists of the alpha-2 adrenergic receptor, beta-blockers, mixed alpha-/beta-blockers, calcium antagonists, calcium channel blockers (CCBs), nasal formulations of the calcium channel blocker diltiazem (e.g. CP-404), dual mineralocorticoid/CCBs, centrally acting antihypertensives, inhibitors of neutral endopeptidase, aminopeptidase-A inhibitors, vasopeptide inhibitors, dual vasopeptide inhibitors such as neprilysin-ACE inhibitors or neprilysin-ECE inhibitors, dual-acting AT receptor-neprilysin inhibitors, dual AT1/ETA antagonists, advanced glycation end-product (AGE) breakers, recombinant renalase, blood pressure vaccines such as anti-RAAS (renin-angiotensin-aldosteron-system) vaccines, AT1- or AT2-vaccines, drugs based on hypertension pharmacogenomics such as modulators of genetic polymorphisms with antihypertensive response, thrombocyte aggregation inhibitors, and others or combinations thereof are suitable.

In some embodiments, a pharmaceutical combination, e.g. a composition or kit, is provided comprising at least one compound of formula I, metformin, and optionally at least one other additional active ingredient, e.g. a DPP-IV inhibitor, an SGLT-2 inhibitor, or a dual SGLT-1/SGLT-2 inhibitor. The combination may be a unitary pharmaceutical composition, e.g. an oral unitary pharmaceutical composition or a kit comprising separate pharmaceutical compositions, each including at least one of the pharmaceutically active ingredients, e.g. separate oral pharmaceutical compositions.

In another aspect, the present disclosure relates to the use of a compound according to the present disclosure or a physiologically acceptable salt or solvate thereof combined with at least one of the active substances described above as a combination partner, for preparing a medicament which is suitable for the treatment or prevention of diseases or conditions which can be affected by binding to the GPR119 and modulating its activity. In one embodiment, the disease or condition is associated with a metabolic syndrome. In one embodiment, the disease or condition is diabetes or obesity or complications thereof.

The present disclosure also provides a method for the treatment or prevention of diseases or conditions which can be affected by binding to GPR119 and modulating its activity in a patient in need thereof comprising administering to the patent a therapeutically effective amount of at least one compound of formula (I), or a physiologically acceptable salt or solvate thereof. In some embodiments, the method comprises administering a compound of formula (I), or a physiologically acceptable salt or solvate thereof, in combination with at least one of the active substances described herein as a combination partner. In some embodiments, the method is for treating a disease or condition associated with a metabolic syndrome. In some embodiments, the method is for treating diabetes or obesity or complications thereof. In some embodiments, the method is for treating diabetes, obesity, dyslipidemia or high blood pressure. In some embodiments, the method is for treating hypertriglyceridemia.

The use of the compounds according to the present disclosure, or a physiologically acceptable salt or solvate thereof, in combination with one or more active substances may take place simultaneously, separately or sequentially.

The use of the compounds according to the present disclosure, or a physiologically acceptable salt or solvate thereof, in combination with another active substance may take place simultaneously or at staggered times, but particularly within a short space of time. If administered simultaneously, the two active substances are given to the patient together; if administered at staggered times, the two active substances are given to the patient within a period of less than or equal to 12 hours, but particularly less than or equal to 6 hours.

Consequently, in another aspect, the present disclosure relates to a medicament which comprises compounds according to the present disclosure, or a physiologically acceptable salt or solvate of such a compound, and at least one of the active substances described above as combination partners, optionally together with one or more inert carriers and/or diluents.

The compounds according to the present disclosure, or a physiologically acceptable salt or solvate thereof, and the additional active substance to be combined therewith may both be present together in one formulation, for example a tablet or capsule, or separately in two identical or different formulations, for example as so-called kit-of-parts.

Compounds according to the present disclosure can be administered to animals, in particular to mammals including humans, as pharmaceuticals by themselves, in mixtures with one another, or in the form of pharmaceutical compositions. The administration can be carried out orally, for example in the form of tablets, film-coated tablets, sugar-coated tablets, granules, hard and soft gelatin capsules, solutions including aqueous, alcoholic and oily solutions, juices, drops, syrups, emulsions or suspensions; rectally, for example in the form of suppositories; or parenterally, for example in the form of solutions for subcutaneous, intramuscular or intravenous injection or infusion, in particular aqueous solutions.

Suitable pharmaceutical compositions for oral administration may be in the form of separate units, for example capsules, cachets, lozenges or tablets, each of which contains a defined amount of the compound of formula I; as powders or granules; as solution or suspension in an aqueous or nonaqueous liquid; or as an oil-in-water or water-in-oil emulsion. These compositions may, as described herein, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surfactant(s)/dispersant(s) in a suitable machine. Molded tablets can be produced by molding the compound, which is in powder form and has been moistened with an inert liquid diluent, in a suitable machine.

Pharmaceutical compositions which are suitable for peroral (sublingual) administration comprise lozenges which contain a compound of formula I with a flavoring agent, typically sucrose, and gum arabic or tragacanth, and pastilles which comprise the compound in an inert base such as gelatin and glycerol or sucrose and gum arabic.

Coated formulations and coated slow-release formulations, especially acid- and gastric juice-resistant formulations, are also contemplated. Suitable coatings resistant to gastric juice include cellulose acetate phthalate, polyvinyl acetate phthalate, hydroxypropylmethylcellulose phthalate and anionic polymers of methacrylic acid and methyl methacrylate.

Pharmaceutical compositions suitable for rectal administration are preferably in the form of single-dose suppositories. These can be produced by mixing a compound of formula I with one or more conventional solid carriers, for example cocoa butter, and shaping the resulting mixture.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the present disclosure generally contain 0.1 to 5% by weight of the active compound.

Other suitable administration forms are, for example, percutaneous or topical administration, for example in the form of ointments, creams, tinctures, sprays, powders or transdermal therapeutic systems; inhalative administration, for example in the form of nasal sprays or aerosol mixtures; or forms such as microcapsules, implants or rods.

Pharmaceutical compositions suitable for topical use on the skin are preferably in the form of ointment, cream, lotion, paste, spray, aerosol or oil. The carriers used may be petrolatum, lanolin, polyethylene glycols, alcohols and combinations of two or more of these substances. The active ingredient is generally present in a concentration of 0.1 to 15% by weight of the composition, for example 0.5 to 2%.

Transdermal administration is also contemplated. Pharmaceutical compositions suitable for transdermal uses may be in the form of single patches which are suitable for long-term close contact with the patient's epidermis. Such patches suitably contain the active ingredient in an aqueous solution which is buffered where appropriate, dissolved and/or dispersed in an adhesive, or dispersed in a polymer. A suitable active ingredient concentration is about 1% to 35%, preferably about 3% to 15%. A particular option is for the active ingredient to be released by electrotransport or iontophoresis as described, for example, in Pharmaceutical Research, 2(6): 318 (1986).

The dosing of compounds according to the present disclosure to achieve the desirable therapeutic effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, 0.1 ng to 100 mg, typically 1 ng to 100 mg, per milliliter. Single doses may contain, for example, 1 mg to 10 g of the active ingredient. Thus, ampoules for injections may contain, for example, from 1 mg to 100 mg, and orally administrable single-dose formulations, for example tablets or capsules, may contain, for example, from 1.0 to 1000 mg, typically from 10 to 600 mg. For prevention and/or treatment of the above-mentioned conditions, the compounds of formula I themselves may be used as the compound, but they are preferably present with a compatible carrier in the form of a pharmaceutical composition. A skilled artisan will understand that the carrier must be acceptable in the sense that it is compatible with the other ingredients of the composition and is not harmful for the patient's health. The carrier may be a solid or a liquid or both and is preferably formulated with the compound as a single dose, for example as a tablet, which may contain 0.05% to 95% by weight of the active ingredient. Other pharmaceutically active substances may likewise be present, including other compounds of formula I. The pharmaceutical compositions of the present disclosure can be produced by one of the known pharmaceutical methods, which comprise mixing the ingredients with pharmacologically acceptable carriers and/or excipients.

The compound(s) of the present disclosure can be prepared for use in suitable pharmaceutical compositions. The suitable pharmaceutical compositions may be in the form of one or more administration units.

The compositions may be prepared by any suitable pharmaceutical method which includes a step in which the compound(s) of the present disclosure and the carrier (which may consist of one or more additional ingredients) are brought into contact.

The administration units may be, for example, capsules, tablets, dragées, granules sachets, drops, solutions, suspensions, lyophylisates and powders, each of which contains a defined amount of the compound(s) of the present disclosure.

Each of the above-mentioned administration units of the compound(s) of the present disclosure or pharmaceutical composition of the present disclosure (administration units)

may be provided in a package for easy transport and storage. The administration units are packaged in standard single or multi-dosage packaging, their form, material and shape depending on the type of units prepared.

In some embodiments, the present disclosure provides kits that comprise a compound of formula (I), in any of its stereoisomeric forms, or a physiologically acceptable salt or solvate thereof, and a set of instructions relating to the use of the compound for the methods described herein. In some embodiments, the kit further comprises one or more inert carriers and/or diluents. In some embodiments, the kit further comprises one or more other pharmacologically active compounds, such as those described herein.

In certain embodiments, administration units may be provided together with a device for application, for example together with a syringe, an injection pen or an autoinjector. Such devices may be provided separate from a pharmaceutical composition or prefilled with the pharmaceutical composition.

A "pen-type injection device", often referred to as "injection pen", is typically an injection device having an elongated shape that resembles a fountain pen for writing. Although such pens usually have a tubular cross-section, they could easily have a different cross-section such as triangular, rectangular or square or any variation around these geometries. Generally, pen-type injection devices comprise three primary elements: a cartridge section that includes a cartridge often contained within a housing or holder; a needle assembly connected to one end of the cartridge section; and a dosing section connected to the other end of the cartridge section. The cartridge, often also referred to as "ampoule", typically includes a reservoir that is filled with a medication, a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

Another subject of the present disclosure are processes for the preparation of the compounds of formula I and their salts and solvates, by which the compounds are obtainable and which are exemplified in the following.

Abbreviations

Abbreviations used herein have their common meanings unless defined otherwise herein. An exemplary list of abbreviations used, can be found below.

| Abbreviation | Meaning |
|---|---|
| Ac | acetyl |
| ACN | acetonitrile |
| amu | atomic mass unit |
| atm | atmosphere (pressure unit, 101325 Pa) |
| Boc$_2$O | di-tert-butyl-dicarbonate |
| BSA | bovine serum albumin |
| cAMP | cyclic adenosine monophosphate |
| CAN | cerium(IV) ammonium nitrate |
| cat. | catalyst/catalyzed |
| CDI | carbonyl diimidazole |
| comp. | compound |
| Dba | dibenzylideneacetone |
| DCM | dichloromethane |
| DEAD | diethyl azodicarboxylate |
| DIAD | diisopropyl azodicarboxylate |
| DIPEA | diisopropyl-ethyl-amine |
| DMAP | 4-dimethylaminopyridine |
| DMEM | Dulbecco's modified eagle medium |
| DMF | dimethylformamide |

-continued

| Abbreviation | Meaning |
|---|---|
| DMSO | dimethyl sulfoxide |
| Dppf | 1,1'-bis(diphenylphosphino)ferrocene |
| EA | ethyl acetate |
| EC$_{50}$ | concentration causing 50% of the maximal response |
| EDCI | ethyl dimethylaminopropyl carbodiimide |
| ESI | electrospray ionization |
| FA | formic acid |
| FCS | fetal calf serum |
| GPR119 | G-protein coupled receptor 119 |
| H | hour(s) |
| Hal | halogen (atom) |
| HATU | O-(7-azabenzotriazol-1-yl)-N,N,N',N'-tetramethyl-uronium hexafluorophosphate |
| HBSS | Hank's buffered salt solution |
| HEK 293 | human embryonic kidney 293 |
| HEPES | 4-(2-hydroxyethyl)-1-piperazineethanesulfonic acid |
| HMDS | hexamethyldisilazane |
| HMPA | hexamethylphosphoric acid triamide |
| HOBt | 1-hydroxy-benzotriazole |
| HPLC | high pressure liquid chromatography |
| HTRF | homogenous time-resolved fluorescence |
| IBMX | 1-methyl-3-(2-methylpropyl)-7H-purine-2,6-dione |
| LCMS | liquid chromatography coupled mass spectroscopy |
| LG | leaving group |
| MCPBA | meta-chloroperoxybenzoic acid |
| MeCN | methyl cyanide (acetonitrile) |
| min | minute(s) |
| Ms | methanesulfonyl |
| MS | mass spectroscopy |
| MTBE | methyl tert.-butyl ether |
| NMP | N-methyl pyrrolidin-2-one |
| NMR | nuclear magnetic resonance (spectrum) |
| PBS | phosphate buffered saline |
| PE | petroleum ether |
| PG | protecting group |
| PMBCl | para-methoxybenzyl chloride |
| R$_t$ | retention time |
| RT | room temperature |
| SFC | supercritical fluid chromatography |
| SGC | silica gel chromatography |
| SiO$_2$ | silica gel (for chromatography) |
| TBAF | tetra-n-butylammonium fluoride |
| TEA | triethylamine |
| TFA | trifluoroacetic acid |
| THF | tetrahydrofuran |
| TIPS | triisopropylsilyl |
| TLC | thin layer chromatography |
| TM | transition metal |
| TMS | tetramethylsilane |
| TMSCHN$_2$ | trimethylsilyldiazomethane |
| Ts | para-tolylsulfonyl |
| UV | ultraviolet (spectrum) |

Synthetic Methods

Variables in the formulae of the schemes represent moieties as defined above unless other meanings are given.

Detailed descriptions of the Typical Procedures to which reference is made in this section can be found in the Compounds section.

Compounds of the present disclosure having the formula I may be prepared by combining known synthetic procedures. In a first method, 3-hydroxy-pyrrolidin-2-one (A') (commercially available as racemic mixture and in both enantiomeric forms) is coupled with aryl halides B' (typically Hal is Br or I) to provide intermediates C. An example for suitable coupling conditions (CuI, N,N'-dimethyl-ethane-1,2-diamine, cesium carbonate) can be found in the Typical Procedure 1. Conversion of the hydroxy group in C to a suitable leaving group (LG; for example Br, I, OTs or OPPh$_3^+$) can be accomplished with various well known reagents (e.g. PPh$_3$/I$_2$, PPh$_3$/CBr$_4$, PPh$_3$/DIAD or TsCl/NEt$_3$) providing the intermediates D, which may be isolated or may be reacted without isolation with hydroxy-aryl building blocks of type E using an appropriate base (e.g. Na$_2$CO$_3$, K$_2$CO$_3$, Cs$_2$CO$_3$ or NaOH). For example, the conditions in the Typical Procedure 3 may be applied to couple intermediates C and E to provide compounds I (A=O; R3a, R3b=H).

A second method of synthesizing compounds I starts with a pyrrolidin-2-one substituted with a leaving group (LG) in 3-position (structures F), which may be prepared by reacting A' with the reagents mentioned above. Other procedures for making structures F are known (e.g. base-promoted cyclization of 2,4-dibromo-butyramide). Intermediates F may be isolated or generated in situ to react with hydroxy-aryls E (typically in the presence of a base as described above) to provide intermediates G. A final step, for example copper-catalyzed coupling with aryl halides B', provides the desired compounds I (A=O; R3a, R3b=H) (Scheme 1).

further compounds B' (Scheme 2b). The reagent HNR'R" can be defined as HNR14R15 or the N-atom can be part of a cycle as defined for R22.

Scheme 2b.

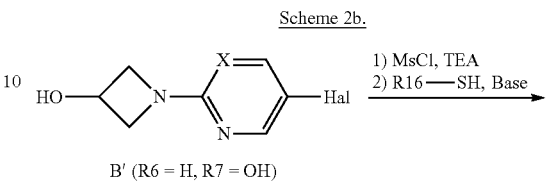

B' (R6 = H, R7 = OH)

Scheme 1.

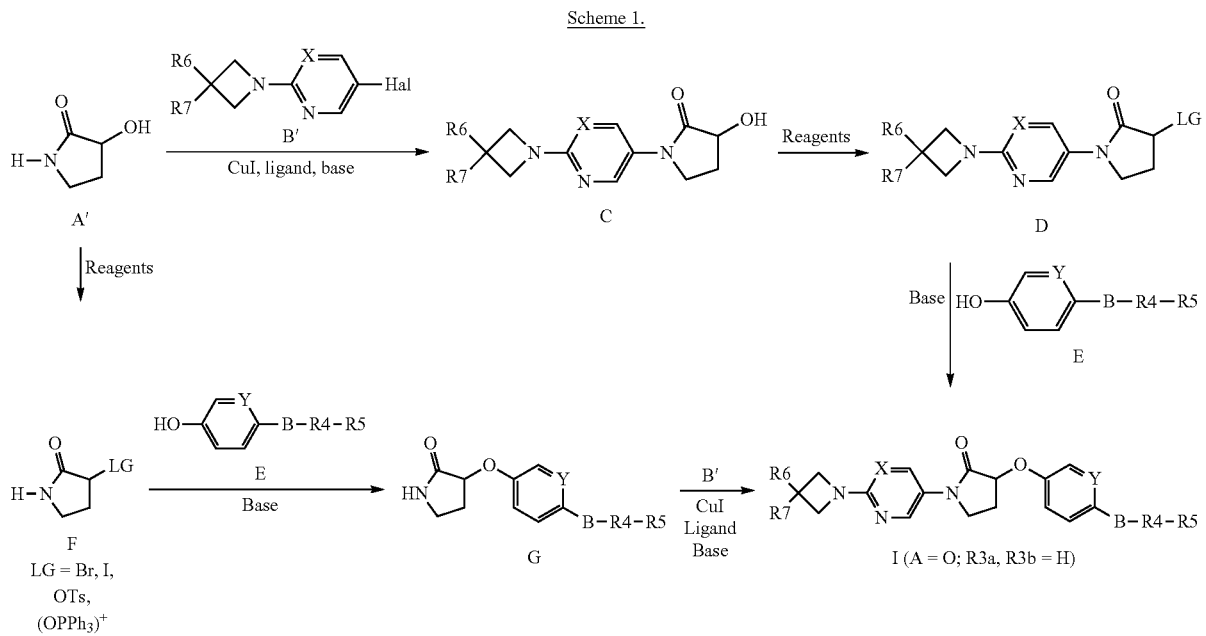

Aryl halides B' may be prepared by reaction of di-halo-pyridines and -pyrimidines, respectively, with substituted azetidines (Scheme 2a). Exemplary reaction conditions are given in the Typical Procedure 2.

Scheme 2a.

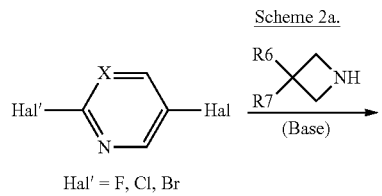

Functional group conversions can be used to vary the substituent(s) in the 3/3'-position of the azetidine to arrive at -continued

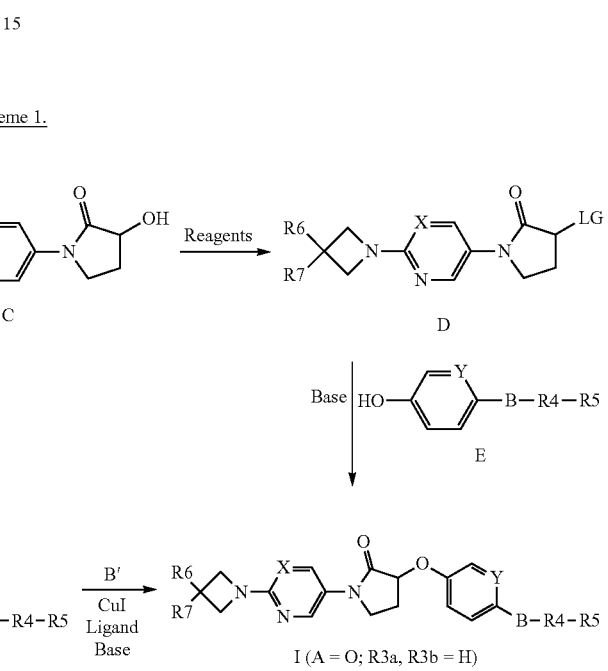

B' (R6 = H, R7 = SR16)

B' (R6 = H, R7 = S(O)$_{1-2}$R16)

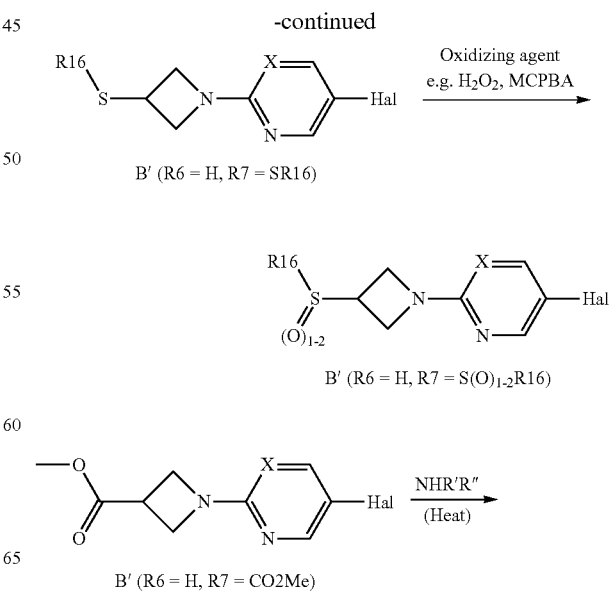

B' (R6 = H, R7 = CO2Me)

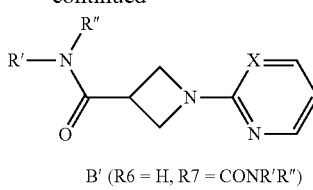

B' (R6 = H, R7 = CONR'R")

Hydroxy-pyridines of the type E (B=O) may be prepared by displacement of a halide (F, Cl, Br or I) in the 2-position of 5-bromo-2-halo-pyridines using nucleophiles of the type HO-R4-R5, followed by conversion of the 5-bromo-substituent to a hydroxy group (e.g. by oxidation of a boronate group introduced by palladium catalyzed coupling with bis-pinacolato-diboron). See Typical Procedure 6 for exemplary conditions for the nucleophilic displacement reaction; Typical Procedure 5 for examples of boronate-oxidation conditions; or Typical Procedure 4 for an example of conditions to install a boronate group.

Certain hydroxy-aryls of the type E (B=CO) may be prepared by metalating suitably protected para-bromo-arenols and subsequent reaction with electrophiles like cyanides or Weinreb-amides to provide—after deprotecion—the desired ketones. Similarly, the metalated side chain (M-R4-R5) can be reacted with a protected para-hydroxy-aryl cyanide/carboxylic acid derivative (Scheme 3).

Scheme 3.

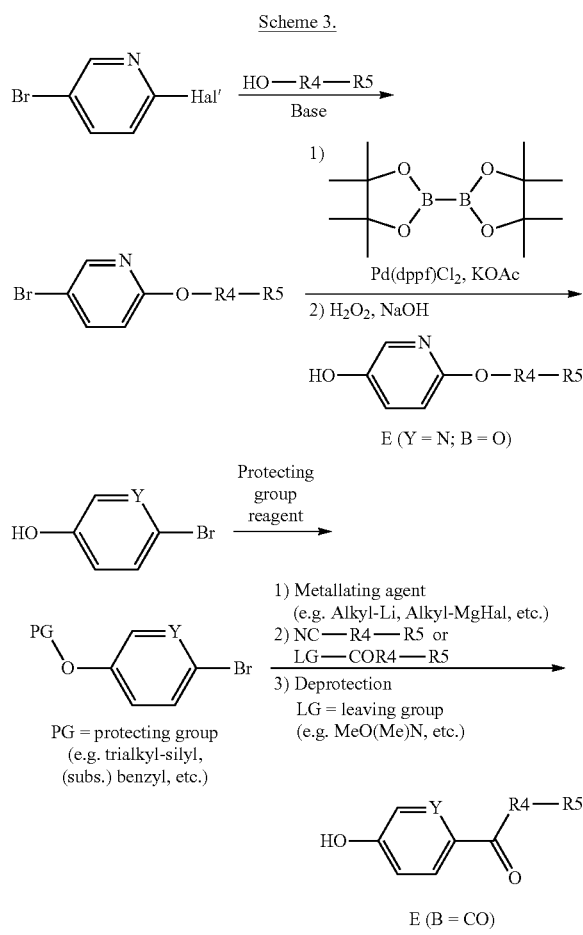

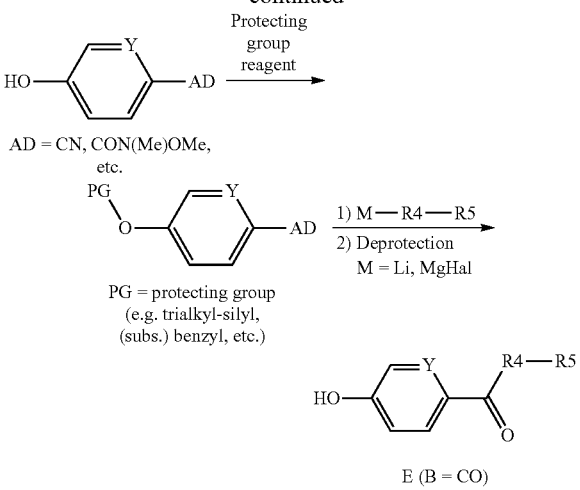

Other derivatives of formula I (e.g. with R7=$(CH_2)_n$—COOH) can be obtained by cleaving the ester functionality in structures I (R7=$(CH_2)_n$—COO($C_1$-$C_2$)-alkyl) for example using the conditions described in Typical Procedure 7. Still other compounds I (R7=$(CH_2)_n$—CONR14R15 or COR22) are provided by the reaction of said acids with amines of the structure HNR'R" using for example EDCl as coupling reagent (see Typical Procedure 8 for exemplary conditions).

Analytical Methods

Compounds were characterized by standard analytical methods. This includes at least two methods (e.g. selected from HPLC, MS and $^1$H-NMR). In particular, MS and HPLC data were obtained by combined analytical HPLC/MS (LCMS). For example, the following LCMS methods were used.

Method A

Column: Waters UPLC BEH C18 2.1*50 mm, 1.7 μm; mobile phase: ($H_2O$+0.05% FA): (MeCN+0.035% FA) 98:2 (0 min) to 5:95 (2 min) to 5:95 (2.6 min) to 95:5 (2.7 min) to 95:5 (3 min); flow rate: 0.9 mL/min; column temperature: 55° C.; ionization method: ESI$^+$; UV wavelength: 220 nm.

Method B

Column: Waters ACQUITY UPLC BEH C18 2.1*50 mm, 1.7 μm; mobile phase: ($H_2O$+0.05% FA): (MeCN+0.035% FA) 98:2 (0 min) to 5:95 (2 min) to 5:95 (2.6 min) to 95:5 (2.7 min) to 95:5 (3 min); flow rate: 0.9 mL/min; column temperature: 55° C.; ionization method: ESI$^+$; UV wavelength: 220 nm.

Method C

Column: Waters ACQUITY UPLC BEH C18 2.1*50 mm, 1.7 μm; mobile phase: ($H_2O$+0.1% FA): (MeCN+0.1% FA) 95:5 (0 min) to 0:100(2 min); flow rate: 1.0 mL/min; column temperature: 45° C.; ionization method: ESI$^+$; UV wavelength: 220 nm.

Method D

Column: Waters ACQUITY SDS UPLC BEH C18 2.1*50 mm, 1.7 μm; mobile phase: ($H_2O$+0.05% FA): (MeCN+0.035% FA) 98:2 (0 min) to 98:2 (0.2 min) to 2:98 (3.8 min) to 2:98 (4.3 min) to 98:2 (4.5 min); flow rate: 1.0 mL/min; column temperature: 55° C.; ionization method: ESI$^+$; UV wavelength: 220 nm.

Method E

Column: YMC J'sphere ODS H80 2.1*20 mm, 4 μm; mobile phase: ($H_2O$+0.05% TFA): MeCN 96:4 (0 min) to 5:95 (2.00 min) to 5:95 (2.40 min) to 96:4 (2.45 min); flow rate: 1.0 mL/min; column temperature: 30° C.; ionization method: ES+; UV wavelength: 220 nm.

In general, HPLC data is represented by the retention time ($R_t$, in min); MS data is given as the observed mass number (m/z) of the ion [M+H]+ (if present) and $^1$H-NMR data is reported by lists of chemical shifts δ (in ppm vs. TMS) of the observed signals (the number of hydrogen atoms was determined using the area under the respective signal; signal multiplicity is characterized as follows: s=singlet, d=doublet, dd=doublet of doublets, t=triplet, dt=doublet of triplets, q=quartet, m=multiplet, br=broad; coupling constants J are given in Hertz (Hz)). Deuterated solvents were used for NMR spectroscopy.

COMPOUNDS

The following compounds are particular embodiments of the present disclosure. They partially illustrate the scope of the present disclosure without limiting it. Abbreviations and chemical symbols have their usual and customary meanings unless otherwise indicated.

The compounds were prepared, isolated and analyzed by the procedures and methods given. Alternatively, they may be prepared by the general synthetic methods detailed above. Further variations of the synthetic procedures will be understood by a person skilled in the art.

When compounds containing a basic group were purified by preparative HPLC on reversed phase column material and, as customary, the eluent was a gradient mixture of water and acetonitrile containing trifluoroacetic acid (TFA), they were obtained in part in the form of their addition salt with TFA, depending on the details of the workup such as evaporation or lyophilization conditions. The compound names and their structural formulae do not specify whether any such TFA present.

Preparation of Compounds of Table 1

Compound 1-01 (Typical Procedure 1)

To a mixture of 5-bromo-2-(3-hydroxy-azetidin-1-yl)-nicotinonitrile (82 mg), (R)-3-((6-(cyclopropylmethoxy)pyridin-3-yl)oxy)pyrrolidin-2-one (80 mg) and 1,4-dioxane (3 mL) was added N,N'-dimethyl-ethane-1,2-diamine (199 mg) and cesium carbonate (262 mg).

The mixture was purged for 5 minutes with a flow of argon and CuI (4.3 mg) was added. The mixture was heated at 100° C. for 1 hour. After cooling to RT, insoluble material was removed by filtration and the filtrate concentrated. The residue was purified by preparative HPLC to provide compound 1-01.

Following generally the Typical Procedure 1, the Compounds 1-01 to 1-54 listed in Table 1 were prepared using the respective aryl bromides and 3-substituted pyrrolidinones.

TABLE 1

| Comp. | Structure | LCMS Method | Rt [min] | ESI+ m/z [amu] |
|---|---|---|---|---|
| 1-01 | 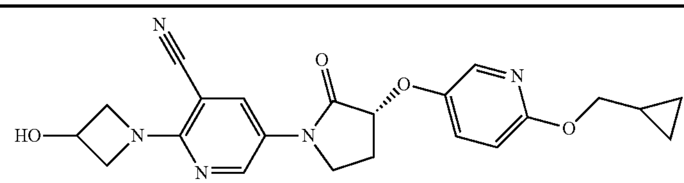 | A | 1.65 | 422.3 |
| 1-02 | 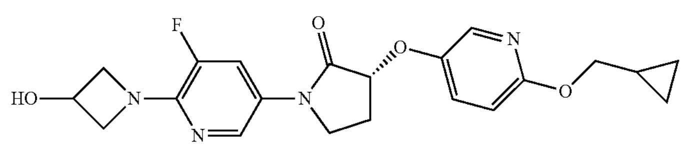 [SMILES: O=C1[C@H](Oc2ccc(OCC3CC3)nc2)CCN1c1cnc(N2CC(O)C2)c(F)c1] | A | 1.80 | 415.1 |
| 1-03 | 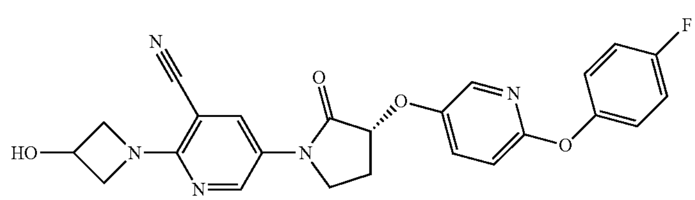 [SMILES: N#Cc1cc(N2CC[C@@H](Oc3ccc(Oc4ccc(F)cc4)nc3)C2=O)cnc1N1CC(O)C1] | A | 1.69 | 462.2 |
| 1-04 | 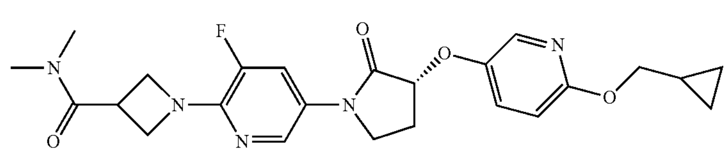 | A | 1.85 | 470.2 |
| 1-05 | 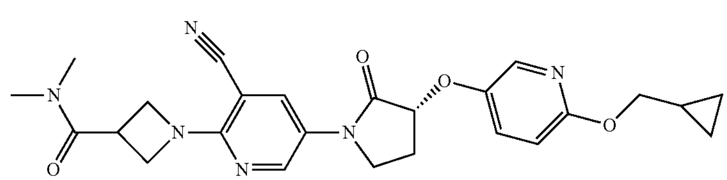 [SMILES: CN(C)C(=O)C1CN(c2ncc(N3CC[C@@H](Oc4ccc(OCC5CC5)nc4)C3=O)cc2C#N)C1] | A | 1.85 | 477.1 |

TABLE 1-continued

| Comp. | Structure | LCMS Method | Rt [min] | ESI+ m/z [amu] |
|---|---|---|---|---|
| 1-06 | 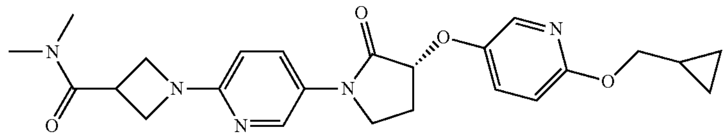 [SMILES: CN(C)C(=O)C1CN(c2ccc(N3CC[C@@H](Oc4ccc(OCC5CC5)nc4)C3=O)cn2)C1] | A | 1.40 | 452.2 |
| 1-07 | 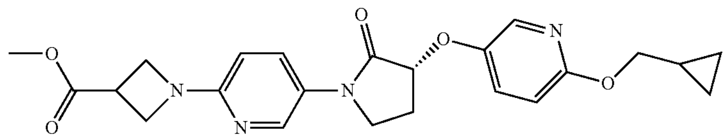 [SMILES: COC(=O)C1CN(c2ccc(N3CC[C@@H](Oc4ccc(OCC5CC5)nc4)C3=O)cn2)C1] | A | 1.52 | 439.1 |
| 1-08 | 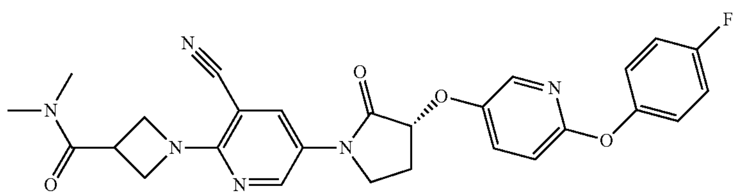 [SMILES: CN(C)C(=O)C1CN(c2ncc(N3CC[C@@H](Oc4ccc(Oc5ccc(F)cc5)nc4)C3=O)cc2C#N)C1] | A | 1.71 | 517.1 |
| 1-09 | 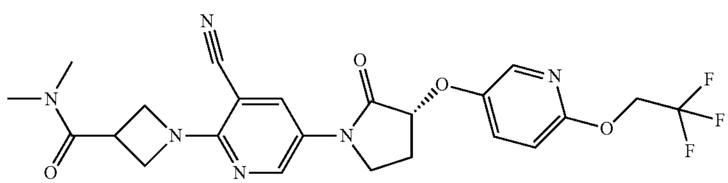 [SMILES: CN(C)C(=O)C1CN(c2ncc(N3CC[C@@H](Oc4ccc(OCC(F)(F)F)nc4)C3=O)cc2C#N)C1] | A | 1.72 | 505.1 |
| 1-10 | 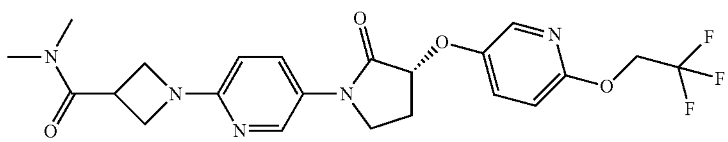 [SMILES: CN(C)C(=O)C1CN(c2ccc(N3CC[C@@H](Oc4ccc(OCC(F)(F)F)nc4)C3=O)cn2)C1] | B | 1.40 | 480.2 |
| 1-11 | 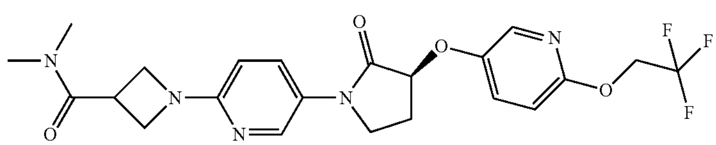 [SMILES: CN(C)C(=O)C1CN(c2ccc(N3CC[C@H](Oc4ccc(OCC(F)(F)F)nc4)C3=O)cn2)C1] | C | 0.88 | 480.0 |
| 1-12 | 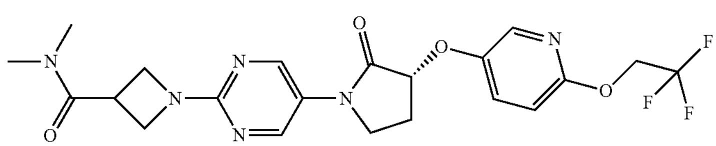 [SMILES: CN(C)C(=O)C1CN(c2ncc(N3CC[C@@H](Oc4ccc(OCC(F)(F)F)nc4)C3=O)cn2)C1] | C | 1.00 | 481.0 |
| 1-13 | 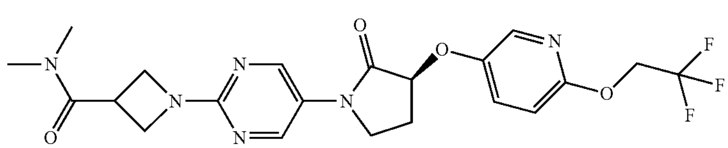 [SMILES: CN(C)C(=O)C1CN(c2ncc(N3CC[C@H](Oc4ccc(OCC(F)(F)F)nc4)C3=O)cn2)C1] | B | 1.61 | 481.2 |
| 1-14 | 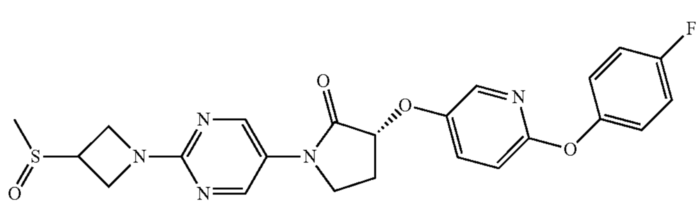 [SMILES: CS(=O)C1CN(c2ncc(N3CC[C@@H](Oc4ccc(Oc5ccc(F)cc5)nc4)C3=O)cn2)C1] | B | 1.49 | 484.1 |

TABLE 1-continued

| Comp. | Structure | LCMS Method | Rt [min] | ESI+ m/z [amu] |
|---|---|---|---|---|
| 1-15 | 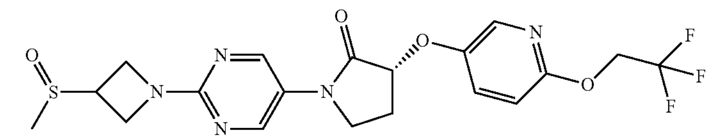 [SMILES: CS(=O)C1CN(c2ncc(N3CC[C@@H](Oc4ccc(OCC(F)(F)F)nc4)C3=O)cn2)C1] | B | 1.48 | 472.1 |
| 1-16 | 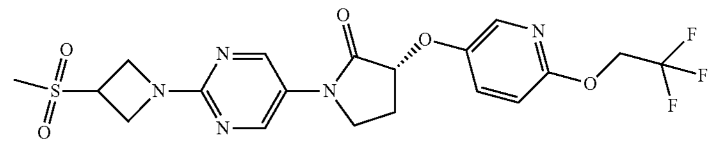 [SMILES: CS(=O)(=O)C1CN(c2ncc(N3CC[C@@H](Oc4ccc(OCC(F)(F)F)nc4)C3=O)cn2)C1] | B | 1.57 | 488.2 |
| 1-17 | 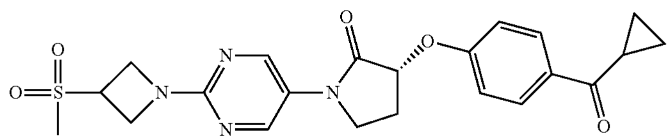 [SMILES: CS(=O)(=O)C1CN(c2ncc(N3CC[C@@H](Oc4ccc(C(=O)C5CC5)cc4)C3=O)cn2)C1] | B | 1.45 | 457.2 |
| 1-18 | 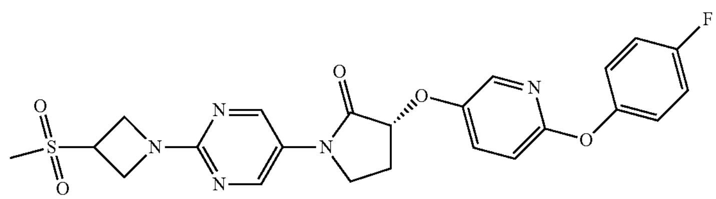 [SMILES: CS(=O)(=O)C1CN(c2ncc(N3CC[C@@H](Oc4ccc(Oc5ccc(F)cc5)nc4)C3=O)cn2)C1] | B | 1.56 | 500.1 |
| 1-19 | 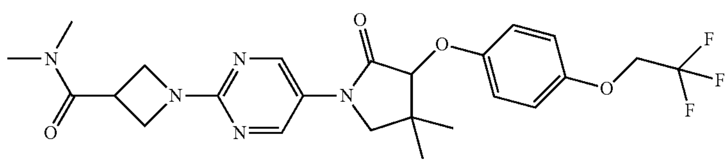 [SMILES: CN(C)C(=O)C1CN(c2ncc(N3CC(C)(C)C(Oc4ccc(OCC(F)(F)F)cc4)C3=O)cn2)C1] | C | 1.16 | 508.0 |
| 1-20 | STEREOISIOMER 1 | D | 1.47 | 441.2 |
| 1-21 | STEREOISOMER 2 | C | 0.85 | 441.0 |
| 1-22 | 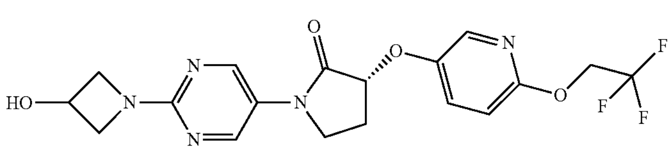 [SMILES: O=C1[C@H](Oc2ccc(OCC(F)(F)F)nc2)CCN1c1cnc(N2CC(O)C2)nc1] | D | 1.69 | 426.1 |
| 1-23 | 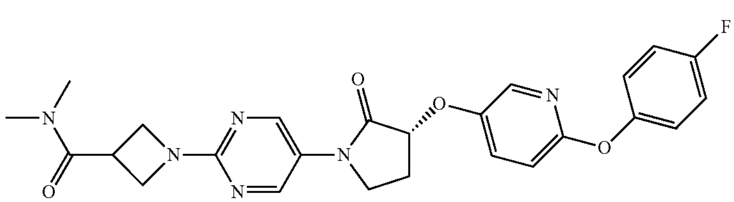 [SMILES: CN(C)C(=O)C1CN(c2ncc(N3CC[C@@H](Oc4ccc(Oc5ccc(F)cc5)nc4)C3=O)cn2)C1] | B | 1.56 | 493.2 |

TABLE 1-continued

| Comp. | Structure | LCMS Method | Rt [min] | ESI+ m/z [amu] |
|---|---|---|---|---|
| 1-24 | STEREOISOMER 1 | B | 1.49 | 472.2 |
| 1-25 | STEREOISOMER 2 | B | 1.49 | 472.2 |
| 1-26 | 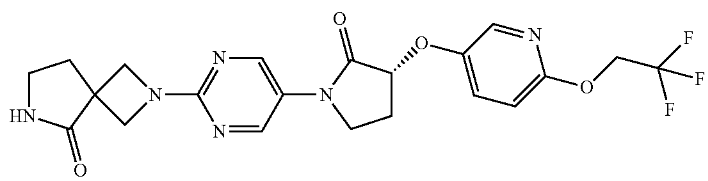 [SMILES: O=C1[C@H](Oc2ccc(OCC(F)(F)F)nc2)CCN1c1cnc(N2CC3(CCNC3=O)C2)nc1] | B | 1.53 | 479.2 |
| 1-27 | 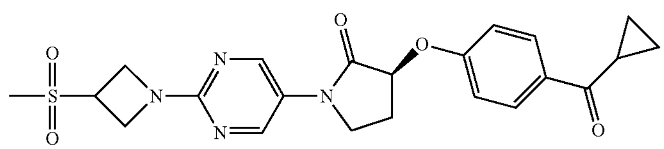 [SMILES: CS(=O)(=O)C1CN(c2ncc(N3CC[C@H](Oc4ccc(C(=O)C5CC5)cc4)C3=O)cn2)C1] | B | 1.45 | 457.3 |
| 1-28 | 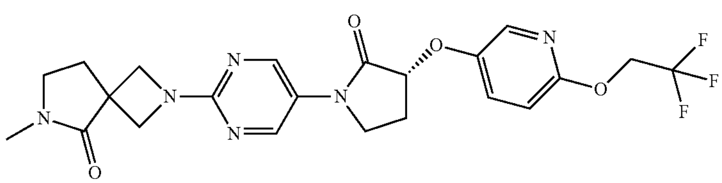 [SMILES: CN1CCC2(CN(c3ncc(N4CC[C@@H](Oc5ccc(OCC(F)(F)F)nc5)C4=O)cn3)C2)C1=O] | B | 1.57 | 493.3 |
| 1-29 | 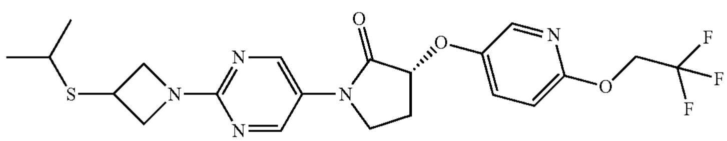 [SMILES: CC(C)SC1CN(c2ncc(N3CC[C@@H](Oc4ccc(OCC(F)(F)F)nc4)C3=O)cn2)C1] | B | 1.86 | 484.3 |
| 1-30 | 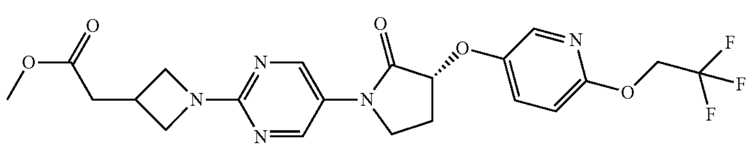 [SMILES: COC(=O)CC1CN(c2ncc(N3CC[C@@H](Oc4ccc(OCC(F)(F)F)nc4)C3=O)cn2)C1] | B | 1.68 | 482.3 |
| 1-31 | 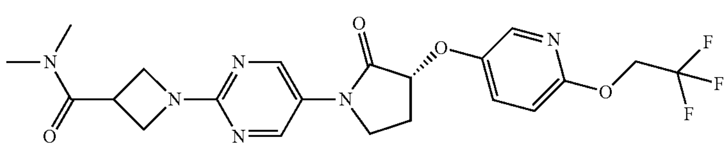 [SMILES: CN(C)C(=O)C1CN(c2ncc(N3CC[C@@H](Oc4ccc(OCC(F)(F)F)nc4)C3=O)cn2)C1] | B | 1.62 | 479.3 |
| 1-32 | 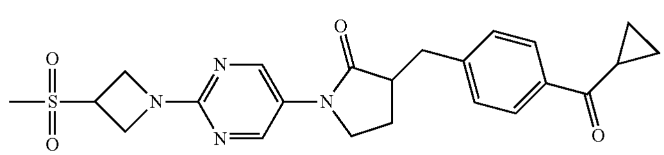 | B | 1.54 | 455.3 |

TABLE 1-continued

| Comp. | Structure | LCMS Method | Rt [min] | ESI+ m/z [amu] |
|---|---|---|---|---|
| 1-33 | 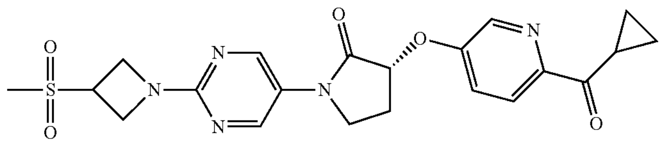 [SMILES: CS(=O)(=O)C1CN(c2ncc(N3CC[C@@H](Oc4ccc(C(=O)C5CC5)nc4)C3=O)cn2)C1] | B | 1.42 | 458.3 |
| 1-34 | 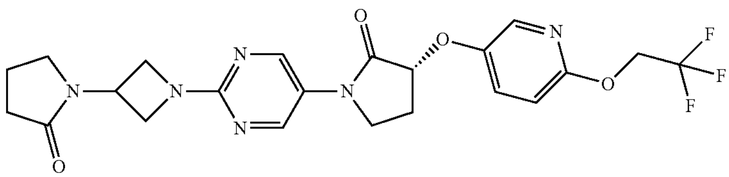 [SMILES: O=C1[C@H](Oc2ccc(OCC(F)(F)F)nc2)CCN1c1cnc(N2CC(N3CCCC3=O)C2)nc1] | B | 1.57 | 493.4 |
| 1-35 | STEREOISOMER 1 | B | 1.58 | 500.3 |
| 1-36 | STEREOISOMER 2 | C | 1.01 | 500.0 |
| 1-37 | 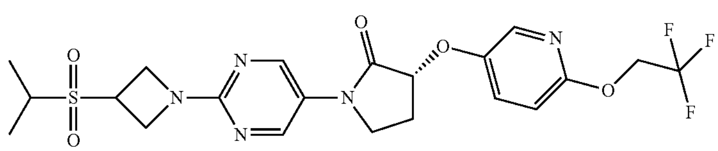 [SMILES: CC(C)S(=O)(=O)C1CN(c2ncc(N3CC[C@@H](Oc4ccc(OCC(F)(F)F)nc4)C3=O)cn2)C1] | B | 1.64 | 516.3 |
| 1-38 | 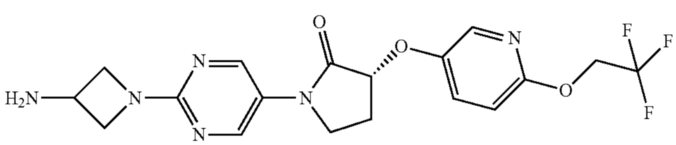 [SMILES: NC1CN(c2ncc(N3CC[C@@H](Oc4ccc(OCC(F)(F)F)nc4)C3=O)cn2)C1] | B | 1.26 | 425.2 |
| 1-39 | 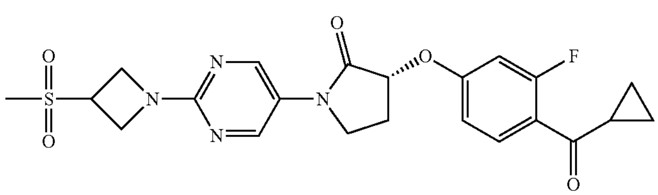 [SMILES: CS(=O)(=O)C1CN(c2ncc(N3CC[C@@H](Oc4ccc(C(=O)C5CC5)c(F)c4)C3=O)cn2)C1] | B | 1.52 | 475.3 |
| 1-40 | 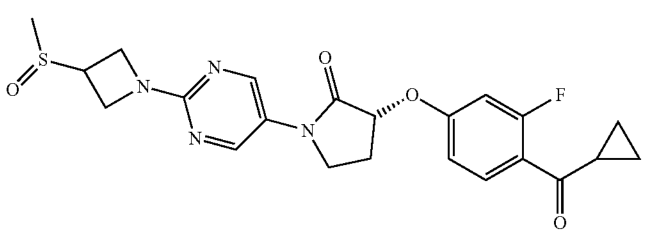 | B | 1.44 | 459.2 |

TABLE 1-continued

| Comp. | Structure | LCMS Method | Rt [min] | ESI+ m/z [amu] |
|---|---|---|---|---|
| 1-41 | 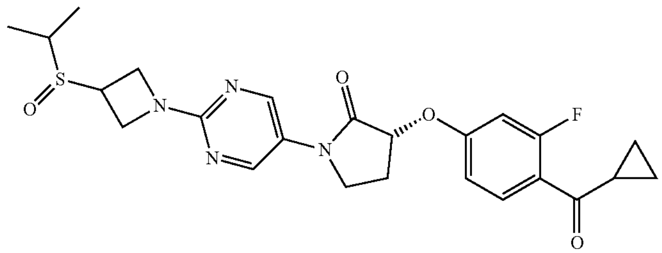 | B | 1.54 | 487.3 |
| 1-42 | STEREOISOMER 1 | B | 1.59 | 479.3 |
| 1-43 | STEREOISOMER 1 | C | 1.02 | 486.0 |
| 1-44 | STEREOISOMER 2 | B | 1.59 | 486.3 |
| 1-45 | STEREOISOMER 2 | B | 1.60 | 479.4 |
| 1-46 | STEREOISOMER 1 | B | 1.54 | 470.3 |
| 1-47 | STEREOISOMER 2 | B | 1.54 | 470.2 |
| 1-48 | 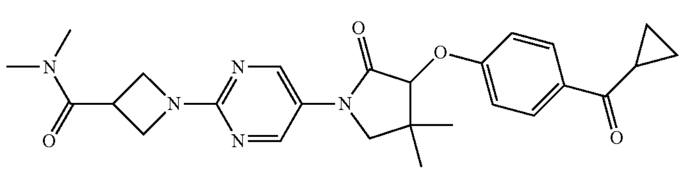 | B | 1.66 | 478.3 |

TABLE 1-continued

| Comp. | Structure | LCMS Method | Rt [min] | ESI+ m/z [amu] |
|---|---|---|---|---|
| 1-49 | 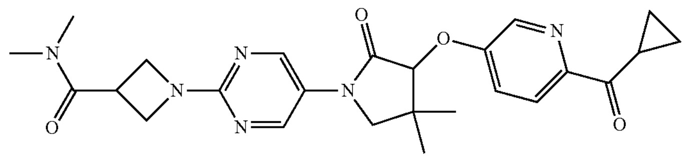 [SMILES: CN(C)C(=O)C1CN(c2ncc(N3CC(C)(C)C(Oc4ccc(C(=O)C5CC5)cc4)C3=O)cn2)C1] | B | 1.62 | 479.3 |
| 1-50 | 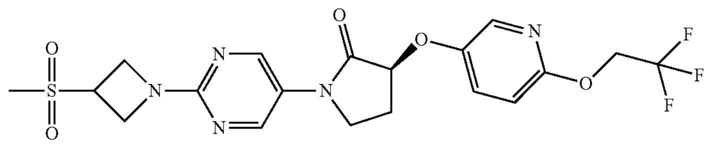 [SMILES: CS(=O)(=O)C1CN(c2ncc(N3CC[C@H](Oc4ccc(OCC(F)(F)F)nc4)C3=O)cn2)C1] | D | 1.78 | 488.1 |
| 1-51 | 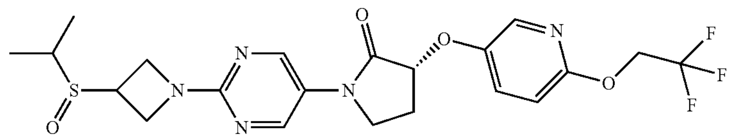 [SMILES: CC(C)S(=O)C1CN(c2ncc(N3CC[C@@H](Oc4ccc(OCC(F)(F)F)nc4)C3=O)cn2)C1] | B | 1.58 | 500.2 |
| 1-52 | 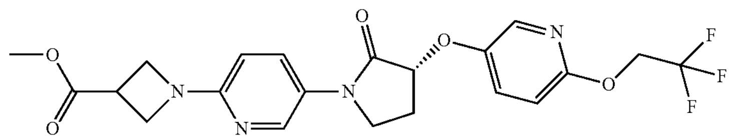 [SMILES: COC(=O)C1CN(c2ccc(N3CC[C@@H](Oc4ccc(OCC(F)(F)F)nc4)C3=O)cn2)C1] | B | 1.56 | 467.2 |
| 1-53 | 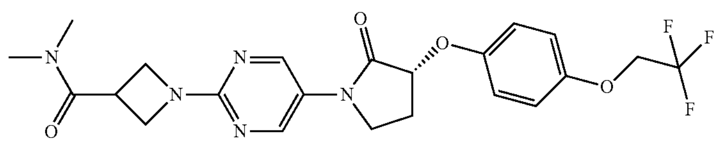 [SMILES: CN(C)C(=O)C1CN(c2ncc(N3CC[C@@H](Oc4ccc(OCC(F)(F)F)cc4)C3=O)cn2)C1] | B | 1.58 | 480.2 |
| 1-54 | 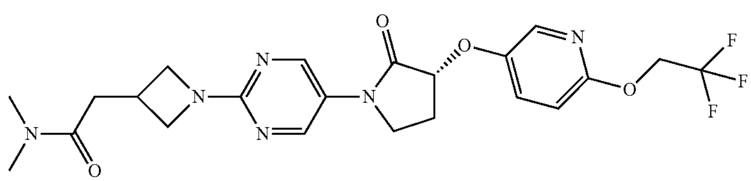 [SMILES: CN(C)C(=O)CC1CN(c2ncc(N3CC[C@@H](Oc4ccc(OCC(F)(F)F)nc4)C3=O)cn2)C1] | B | 1.58 | 495.3 |

5-Bromo-2-(3-methanesulfinyl-azetidin-1-yl)-pyrimidine (enantiomer 1 and enantiomer 2, respectively) was reacted with (R)-3-(4-cyclopropanecarbonyl-phenoxy)-pyrrolidin-2-one according to Typical Procedure 1 to provide compounds 1-20 and 1-21, respectively. 5-Bromo-2-(3-methanesulfinyl-azetidin-1-yl)-pyrimidine (enantiomer 1 and enantiomer 2, respectively) was reacted with (R)-3-[6-(2,2,2-trifluoro-ethoxy)-pyridin-3-yloxy]-pyrrolidin-2-one according to Typical Procedure 1 to provide compounds 1-24 and 1-25, respectively.

5-Bromo-2-[3-(propane-2-sulfinyl)-azetidin-1-yl]-pyrimidine (enantiomer 1 and enantiomer 2, respectively) was reacted with (R)-3-[6-(2,2,2-trifluoro-ethoxy)-pyridin-3-yloxy]-pyrrolidin-2-one according to Typical Procedure 1 to provide compounds 1-35 and 1-36, respectively.

5-Bromo-2-(3-methanesulfinyl-azetidin-1-yl)-pyrimidine (enantiomer 1) was reacted with 3-[6-(2,2,2-trifluoro-ethoxy)-pyridin-3-ylmethyl]-pyrrolidin-2-one (enantiomer 1 and enantiomer 2, respectively) according to Typical Procedure 1 to provide compounds 1-46 and 1-47, respectively.

3-[6-(2,2,2-Trifluoro-ethoxy)-pyridin-3-ylmethyl]-pyrrolidin-2-one (enantiomer 1) was used in the preparation of compounds 1-42, 1-43 and 1-46.

3-[6-(2,2,2-Trifluoro-ethoxy)-pyridin-3-ylmethyl]-pyrrolidin-2-one (enantiomer 2) was used in the preparation of compounds 1-44, 1-45 and 1-47.

Occasionally, (minor) partial racemization/epimerization of the pyrrolidinone (3R)-stereocenter was observed under the reaction conditions of Typical Procedure 1. Thus, using chiral HPLC in the purification step, compounds with (3S)-configuration were obtained as additional reaction products (compounds 1-11, 1-13, 1-27 and 1-50, respectively). Alternatively, pyrrolidinone intermediates with (3S)-configuration, obtained by substituting (R)-3-hydroxy-pyrrolidin-2-one for (S)-3-hydroxy-pyrrolidin-2-one in the procedures given below, may be reacted according Typical Procedure 1.

Occasionally, for target compounds containing ester groups, carboxylic acids were obtained as (additional) products from the reaction mixture due to (partial) ester hydrolysis under the reaction conditions of Typical Procedure 1. The carboxylic acids obtained can be converted to methyl esters (e.g. Compound 1-07) by dissolving the respective acid in DCM (5 mL/mmol) and methanol (0.5 mL/mmol) and addition of TMSCHN$_2$ (1.5 equiv.). After the gas evolution has ceased, the reaction mixture is evaporated to provide the desired methyl ester.

Alternative Preparation of Compound 1-06

To a mixture of 1-(5-bromo-pyridin-2-yl)-azetidine-3-carboxylic acid dimethylamide (103 mg), (R)-3-(6-cyclopropylmethoxy-pyridin-3-yloxy)-pyrrolidin-2-one (90 mg) and 1,4-dioxane (3 mL) was added N,N'-dimethyl-ethane-1,2-diamine (224 mg) and cesium carbonate (295 mg). The mixture was purged for 5 minutes with a flow of argon and CuI (4.8 mg) was added. The mixture was heated at 80° C. for 75 minutes. After cooling to RT, insoluble material was removed by filtration and the filtrate concentrated. The residue was purified by preparative HPLC to provide Compound 1-06. 1H NMR (DMSO-d6, 400 MHz), δ ppm: 8.29-8.33 (m, 1H), 8.06 (br d, J=9.0 Hz, 1H), 7.94 (d, J=2.7 Hz, 1H), 7.52 (dd, J=8.9, 2.6 Hz, 1H), 6.79 (d, J=8.9 Hz, 1H), 6.71 (br d, J=9.0 Hz, 1H), 5.15 (br t, J=8.0 Hz, 3H), 4.64 (br s, 5H), 4.22-4.46 (m, 4H), 4.15 (br t, J=7.2 Hz, 3H), 4.03 (d, J=7.1 Hz, 2H), 3.70-3.96 (m, 4H), 2.90 (s, 3H), 2.86 (s, 3H), 2.62-2.76 (m, 1H), 2.01-2.23 (m, 1H), 1.16-1.27 (m, 1H), 0.48-0.56 (m, 2H), 0.26-0.34 (m, 2H).

Alternative Preparation of Compound 1-10

To a mixture of 1-[5-((S)-3-hydroxy-2-oxo-pyrrolidin-1-yl)-pyridin-2-yl]-azetidine-3-carboxylic acid dimethylamide (1.1 g), 6-(2,2,2-trifluoro-ethoxy)-pyridin-3-ol (698 mg) and dichloromethane (3.0 mL) was added triphenylphosphine (polymer-bound, 2.15 mmol/g, 3.5 g). After five minutes, DIAD (710 μL) was added and the mixture was shaken and then left at room temperature for one hour. A further amount of DIAD (355 μL) was added. After one hour, insoluble material was removed by filtration and the filtrate concentrated. The residue was purified by SGC (DCM to 20% MeOH in EA) to provide Compound 1-10. 1H NMR (400 MHz, DMSO-d6) δ ppm: 8.31 (d, J=2.2 Hz, 1 H), 8.01 (d, J=2.8 Hz, 1 H), 7.87 (dd, J=9.0, 2.7 Hz, 1 H), 7.62 (dd, J=9.0, 3.1 Hz, 1 H), 6.96 (d, J=9.0 Hz, 1 H), 6.47 (d, J=8.5 Hz, 1 H), 5.21 (t, J=8.0 Hz, 1 H), 4.93 (q, J=9.1 Hz, 2 H), 4.11 (m, 2 H), 3.99 (t, J=7.1 Hz, 2 H), 3.81 (m, 3 H), 2.90 (s, 3 H), 2.85 (s, 3 H), 2.69 (m, 1 H), 2.12 (dq, J=12.5, 8.4 Hz, 1 H).

Alternative Preparation of Compound 1-12

To a mixture of 1-(5-bromo-pyrimidin-2-yl)-azetidine-3-carboxylic acid dimethylamide (1.50 g), (R)-3-[6-(2,2,2-trifluoro-ethoxy)-pyridin-3-yloxy]-pyrrolidin-2-one (1.60 g) and 1,4-dioxane (10 mL) was added N,N'-dimethyl-ethane-1,2-diamine (5.0 mL). The mixture was purged for 4 minutes with a flow of argon and cesium carbonate (2.5 g) was added. The mixture was purged for 2 minutes with a flow of argon and CuI (1.0 g) was added. The mixture was heated at 80° C. for two hours. After cooling to RT, the mixture was diluted with ACN/DCM (2:1, 100 mL). Insoluble material was removed by filtration and the filtrate concentrated. The residue was purified by SGC (DCM to 20% MeOH in EA) to provide Compound 1-12 after recrystallization from ethanol. 1H NMR (400 MHz, DMSO-d6) δ ppm: 8.65 (s, 2 H), 8.01 (d, J=2.9 Hz, 1 H), 7.62 (dd, J=9.0, 3.1 Hz, 1 H), 6.96 (d, J=8.9 Hz, 1 H), 5.22 (t, J=8.1 Hz, 1 H), 4.93 (q, J=9.1 Hz, 2 H), 4.21 (t, J=8.6 Hz, 2 H), 4.10 (dd, J=8.6, 6.2 Hz, 2 H), 3.81 (m, 3 H), 2.90 (s, 3 H), 2.85 (s, 3 H), 2.71 (m, 1 H), 2.14 (m, 1 H).

Alternative Preparation of Compound 1-16

To a mixture of 5-bromo-2-(3-methanesulfonyl-azetidin-1-yl)-pyrimidine (1.20 g), (R)-3-[6-(2,2,2-trifluoro-ethoxy)-pyridin-3-yloxy]-pyrrolidin-2-one (1.00 g) and 1,4-dioxane (10 mL) was added N,N'-dimethyl-ethane-1,2-diamine (5.0 mL). The mixture was purged for 2 minutes with a flow of argon and cesium carbonate (2.0 g) was added. The mixture was purged for 0.5 minutes with a flow of argon and CuI (500 mg) was added. The mixture was heated at 80° C. for 30 minutes. After cooling to RT, the mixture was diluted with DCM (25 mL). Insoluble material was removed by filtration and the filtrate concentrated. The residue was purified by SGC (DCM to 20% MeOH in EA) to provide Compound 1-16. 1H NMR (400 MHz, DMSO-d6) δ ppm: 8.72 (s, 2 H), 8.02 (d, J=2.9 Hz, 1 H), 7.63 (dd, J=8.9, 3.1 Hz, 1 H), 6.97 (d, J=9.1 Hz, 1 H), 5.23 (t, J=8.1 Hz, 1 H), 4.93 (q, J=9.13 Hz, 2 H), 4.37 (m, 3 H), 4.24 (m, 2 H), 3.82 (m, 2 H), 3.06 (s, 3 H), 2.72 (m, 1 H), 2.15 (m, 1 H).

Alternative Preparation of Compound 1-17

To a mixture of 5-bromo-2-(3-methanesulfonyl-azetidin-1-yl)-pyrimidine (1.01 g), (R)-3-(4-cyclopropanecarbonyl-phenoxy)-pyrrolidin-2-one (0.91 g) and 1,4-dioxane (10 mL) was added N,N'-dimethyl-ethane-1,2-diamine (5.0 mL). The mixture was purged for four minutes with a flow of argon and cesium carbonate (1.69 g) was added. The mixture was purged for one minute with a flow of argon and CuI (670 mg) was added. The mixture was heated at 80° C. for two hours. After cooling to RT, the mixture was diluted with ACN/DCM (1:1, 300 mL). Insoluble material was removed by filtration and washed with DCM (100 mL). The combined organic solutions were concentrated. The residue was suspended in hydrochloric acid (0.1 M, 100 mL) and the mixture extracted with EA/DCM (9:1, 100 mL×3). The combined organic layers were washed twice with brine, dried over Na₂SO₄ and concentrated. The residue was suspended with ethanol (125 mL). Filtration provided Compound 1-17. 1H NMR (400 MHz, DMSO-d6) δ ppm: 8.73 (s, 2 H), 8.05 (m (para), J=8.9 Hz, 2 H), 7.19 (m (para), J=8.8 Hz, 2 H), 5.41 (t, J=8.1 Hz, 1 H), 4.37 (m, 3 H), 4.24 (m, 2 H), 3.85 (m, 2 H), 3.06 (s, 3 H), 2.83 (m, 2 H), 2.15 (m, 1 H), 1.00 (m, 4 H).

Alternative Preparation of Compound 1-37

To a mixture of 5-bromo-2-[3-(propane-2-sulfonyl)-azetidin-1-yl]-pyrimidine (93 mg), (R)-3-[6-(2,2,2-trifluoro-ethoxy)-pyridin-3-yloxy]-pyrrolidin-2-one (80 mg) and 1,4-dioxane (1.0 mL) was added N,N'-dimethyl-ethane-1,2-diamine (0.5 mL). The mixture was purged for two minutes with a flow of argon and cesium carbonate (180 mg) was added. The mixture was purged for 30 seconds with a flow of argon and CuI (50 mg) was added. The mixture was heated at 80° C. for 30 minutes. After cooling to RT, the mixture was diluted with MeOH/water (9:1, 0.5 mL). Insoluble material was removed by filtration.

The filtrate was subjected to preparative HPLC to provide compound 1-37. 1H NMR (400 MHz, DMSO-d6) δ ppm: 8.72 (s, 2 H), 8.02 (d, J=3.1 Hz, 1 H), 7.63 (dd, J=9.0, 3.1 Hz, 1 H), 6.97 (d, J=8.9 Hz, 1 H), 5.23 (t, J=8.1 Hz, 1 H), 4.93 (q, J=9.2 Hz, 2 H), 4.57 (m, 1 H), 4.36 (t, J=8.9 Hz, 2 H), 4.22 (dd, J=9.7, 5.8 Hz, 2 H), 3.79 (m, 2 H), 3.35 (m, 1H), 2.72 (m, 1 H), 2.15 (m, 1 H), 1.24 (d, J=6.9 Hz, 6 H).

Alternative Preparation of Compound 1-42

To a mixture of 1-(5-bromo-pyrimidin-2-yl)-azetidine-3-carboxylic acid dimethylamide (80 mg), 3-[6-(2,2,2-trifluoro-ethoxy)-pyridin-3-ylmethyl]-pyrrolidin-2-one (enantiomer 1, 70 mg) and 1,4-dioxane (1.0 mL) was added N,N'-dimethyl-ethane-1,2-diamine (0.5 mL).

The mixture was purged for two minutes with a flow of argon and cesium carbonate (130 mg) was added. The mixture was purged for 30 seconds with a flow of argon and CuI (30 mg) was added. The mixture was heated at 80° C. for one hour. After cooling to RT, the mixture was diluted with MeOH/water (9:1, 1 mL). Insoluble material was removed by filtration. The filtrate was subjected to preparative HPLC to provide compound 1-42. 1H NMR (DMSO-d6, 400 MHz), δ ppm: 8.60 (s, 2H), 8.09 (d, J=2.1 Hz, 1H), 7.72 (dd, J=8.5, 2.4 Hz, 1H), 6.93 (d, J=8.4 Hz, 1H), 4.96 (q, J=9.1 Hz, 2H), 4.14-4.27 (m, 2H), 4.09 (dd, J=8.4, 6.2 Hz, 4H), 3.74-3.94 (m, 16H), 3.49-3.74 (m, 4H), 3.05 (dd, J=13.8, 4.5 Hz, 1H), 2.84-2.93 (m, 7H), 2.52-2.73 (m, 1H), 2.05-2.14 (m, 1H), 1.77 (dq, J=12.4, 8.9 Hz, 1H).

Alternative Preparation of Compound 1-43

To a mixture of 5-bromo-2-(3-methanesulfonyl-azetidin-1-yl)-pyrimidine (80 mg), 3-[6-(2,2,2-trifluoro-ethoxy)-pyridin-3-ylmethyl]-pyrrolidin-2-one (enantiomer 1, 70 mg) and 1,4-dioxane (1.0 mL) was added N,N'-dimethyl-ethane-1,2-diamine (0.5 mL). The mixture was purged for two minutes with a flow of argon and cesium carbonate (130 mg) was added. The mixture was purged for 30 seconds with a flow of argon and CuI (30 mg) was added. The mixture was heated at 80° C. for one hour. After cooling to RT, the mixture was diluted with MeOH/water (9:1, 1 mL). Insoluble material was removed by filtration. The filtrate was subjected to preparative HPLC to provide Compound 1-43. 1H NMR (DMSO-d6, 400 MHz), δ ppm: 8.66 (s, 2H), 8.09 (d, J=2.1 Hz, 1H), 7.72 (dd, J=8.5, 2.4 Hz, 1H), 6.93 (d, J=8.4 Hz, 1H), 4.96 (q, J=9.2 Hz, 2H), 4.30-4.44 (m, 3H), 4.19-4.24 (m, 2H), 3.59-3.81 (m, 4H), 3.41 (br s, 1H), 3.23 (s, 1H), 3.02-3.09 (m, 4H), 2.91 (qd, J=9.0, 4.7 Hz, 1H), 2.70 (dd, J=13.8, 9.0 Hz, 1H), 2.06-2.14 (m, 1H), 1.78 (dq, J=12.5, 8.9 Hz, 1H).

Preparation of 3-Substituted Pyrrolidin-2-ones (R)-3-[6-(4-Fluoro-phenoxy)-pyridin-3-yloxy]-pyrrolidin-2-one (Typical Procedure 3)

A mixture of THF (200 mL) and DCM (100 mL) under argon was added triphenylphosphine (polymer bound, 1.8 mmol/g, 20 g). Diisopropyl azodicarboxylate (8.87 g) was added. After 5 minutes, (S)-3-hydroxy-pyrrolidin-2-one (3.1 g) and 6-(4-fluoro-phenoxy)-pyridin-3-ol (6.0 g) were added. After 30 minutes, the mixture was filtered and the filtrate concentrated. The residue was purified by chromatography (SiO₂; DCM/MeOH 15:1) to provide (R)-3-[6-(4-fluoro-phenoxy)-pyridin-3-yloxy]-pyrrolidin-2-one. MS ESI⁺: m/z=289 [M+H]⁺.

6-(4-Fluoro-phenoxy)-pyridin-3-ol

A mixture of 6-bromo-pyridin-3-ol (8.0 g), 4-fluorophenol (15.5 g) and cesium carbonate (30 g) was heated to 170° C. for 6 hours. After the mixture reached room temperature, it was distributed between water and MTBE. The organic phase was dried (Na₂SO₄) and concentrated. The residue was purified by chromatography (SiO₂, EA/heptane 1:1.5) to provide 6-(4-fluoro-phenoxy)-pyridin-3-ol. MS ESI⁺: m/z=206 [M+H]⁺.

(R)-3-[6-(2-Cyclopropyl-methoxy)-pyridin-3-yloxy]-pyrrolidin-2-one

A mixture of (S)-3-hydroxy-pyrrolidin-2-one (3.00 g), 6-(2-cyclopropyl-methoxy)-pyridin-3-ol (4.90 g), triphenylphosphine (polymer, 8.56 g), DCM (30 mL) and THF (50 mL) was added DIAD (6.60 g) keeping the reaction temperature below 30° C. After 12 hours, the mixture was filtered and the filtrate was evaporated. The residue was purified by SGC (eluent: EA/MeOH 9:1) to provide (R)-3-[6-(2-cyclopropyl-methoxy)-pyridin-3-yloxy]-pyrrolidin-2-one. MS ESI⁺: m/z=249 [M+H]⁺.

6-Cyclopropylmethoxy-pyridin-3-ol

Typical Procedure 4: A mixture of 5-bromo-2-cyclopropylmethoxy-pyridine (8.00 g), bis(pinacolato)diboron (8.91 g) and 1,4-dioxane (53 mL) was purged with argon. Potassium acetate (3.44 g) and Pd(dppf)Cl₂ (2.57 g) were added and the mixture heated to 100° C. for 1 hour by microwave irradiation. The mixture was filtered and the filtrate diluted with EA, washed with water, dried (Na₂SO₄) and concentrated. The residue was purified by SGC (eluent: EA/heptane 1:6) to provide the crude boronate. MS ESI⁺: m/z=276 [M+H]⁺. Typical Procedure 5: The boronate was dissolved in THF (60 mL). Aqueous NaOH (5 M) was added at 0° C. Hydrogen peroxide (30% in water, 30 mL) was added slowly. The mixture was allowed to warm to RT and stirred for 4 hours. The mixture was extracted with MTBE. The aqueous phase was adjusted to pH 3-4 by addition of diluted HCl and extracted with EA. The organic phase was dried (Na₂SO₄) and concentrated to provide 6-cyclopropyl-methoxy-pyridin-3-ol. MS ESI⁺: m/z=166 [M+H]⁺.

5-Bromo-2-cyclopropylmethoxy-pyridine

Typical Procedure 6: To a mixture of 2-cyclopropyl-methanol (6.15 g) and DMF (12 mL) was added NaH (60% in mineral oil, 1.5 g) at 0° C. After stirring for 4 hours at RT, the mixture was diluted with DMF (5 mL) and 5-bromo-2-fluoro-pyridine (6.00 g) was slowly added keeping the reaction temperature below 30° C. After 30 minutes at RT, the mixture was heated to 130° C. for 1 hour by microwave irradiation. After cooling to RT, the mixture was diluted with EA and washed with water (3 times). The organic phase was dried (Na₂SO₄) and concentrated. The residue was purified by SGC to provide 5-bromo-2-cyclopropylmethoxy-pyridine. MS ESI⁺: m/z=228 [M+H]⁺.

(R)-3-[6-(2,2,2-Trifluoro-ethoxy)-pyridin-3-yloxy]-pyrrolidin-2-one

To a mixture of 6-(2,2,2-trifluoroethoxy)pyridin-3-ol (40 g), (S)-3-hydroxy-pyrrolidin-2-one (25.1 g) and PPh₃ (70.6 g) in THF (600 mL) was added DIAD (50.2 g) dropwise at RT under nitrogen. The mixture was stirred at RT overnight. The solvent was removed, and the residue was purified by silica gel chromatography (DCM:MeOH=30:1) to remove most of the triphenylphosphine oxide side product. The product containing fractions were concentrated and redissolved in EA/PE (1:3, 200 mL). The solution was cooled (0° C.) in a refrigerator overnight. The white solid formed was filtered and washed with PE to provide (R)-3-[6-(2,2,2-trifluoro-ethoxy)-pyridin-3-yloxy]-pyrrolidin-2-one. MS ESI⁺: m/z=277 [M+H]⁺.

6-(2,2,2-Trifluoroethoxy)pyridin-3-ol

To a mixture of 5-bromo-2-(2,2,2-trifluoroethoxy)pyridine (60 g), bis(pinacolato)diboron (77.4 g), KOAc (45.9 g)

and 1,4-dioxane (800 mL) was added Pd(dppf)Cl$_2$ (9.56 g). The mixture was stirred at 95° C. under nitrogen overnight. Water (500 mL) was added to the mixture, followed by extraction with ethyl acetate (400 mL×3). The organic phase was washed with brine and dried (Na$_2$SO$_4$). Filtration and evaporation of the solvent provided the crude boronate which was used directly in next step without further purification.

To a mixture of the crude boronate (71 g) and THF/H$_2$O (500 mL/500 mL) was added NaBO$_3$*4 H$_2$O (72.2 g) at 0° C. slowly. The reaction mixture was stirred at room temperature for four hours. Saturated aqueous NH$_4$Cl (400 mL) was added to the mixture, followed by extraction with ethyl acetate (600 mL×3). The organic phase was washed with brine and dried (Na$_2$SO$_4$). Filtration and evaporation of the solvent provided a residue which was purified by column chromatography on silica gel eluting with PE:EA=20:1 to provide 6-(2,2,2-trifluoroethoxy)pyridin-3-ol as a white solid. MS ESI$^+$: m/z=194 [M+H]$^+$.

5-Bromo-2-(2,2,2-trifluoroethoxy)pyridine

To a solution of 2,2,2-trifluoroethanol (125 g) and 5-bromo-2-fluoro-pyridine (200 g) in dry MTBE (2000 mL), was added t-BuOK (192 g) at 0° C. slowly. The reaction mixture was stirred at room temperature for six hours. Water (800 mL) was added to the mixture, followed by extraction with ethyl acetate (600 mL×3). The combined organic phases were washed with brine and dried over Na$_2$SO$_4$. After filtration and evaporation of the solvent, the resulting residue was purified by column chromatography on silica gel eluting with PE:EA=50:1 to provide 5-bromo-2-(2,2,2-trifluoroethoxy) pyridine as a white solid. MS ESI$^+$: m/z=256 [M+H]$^+$.

(R)-3-(4-(Cyclopropanecarbonyl)phenoxy)pyrrolidin-2-one

Following Typical Procedure 3, (S)-3-hydroxypyrrolidin-2-one was reacted with cyclopropyl-(4-hydroxy-phenyl)-methanone to provide (R)-3-(4-(cyclopropanecarbonyl)phenoxy)pyrrolidin-2-one. MS ESI$^+$: m/z=246 [M+H]$^+$.

Cyclopropyl-(4-hydroxy-phenyl)-methanone

A mixture of t-BuOK (30 g) and dry THF (60 mL) was cooled to −5° C. A solution of 4-chloro-1-(4-hydroxy-phenyl)-butan-1-one (24 g) in dry THF (80 mL) was added at −5 to 0° C. The mixture was stirred at 0° C. for one hour and added to a stirred solution of phosphoric acid (85%, 18.1 g) in water (100 mL), then warmed slowly to room temperature and stirred for 2 h. The mixture was extracted with EA (100 mL×2), the combined organic phase was washed with brine (50 mL). The combined aqueous layers were re-extracted with EA (80 mL). The combined organic layers were concentrated, and the residue was purified by SGC (PE:EA=4:1) to provide cyclopropyl-(4-hydroxy-phenyl)-methanone. MS ESI$^+$: m/z=163 [M+H]$^+$.

4,4-Dimethyl-3-[4-(2,2,2-trifluoro-ethoxy)-phenoxy]-pyrrolidin-2-one

A solution of 1-(2,4-dimethoxybenzyl)-4,4-dimethyl-3-(4-(2,2,2-trifluoroethoxy)phenoxy) pyrrolidin-2-one (180 mg) in TFA (5 mL) was heated at 60° C. for six hours. The mixture was concentrated and the residue was purified by preparative HPLC to provide 4,4-dimethyl-3-[4-(2,2,2-trifluoro-ethoxy)-phenoxy]-pyrrolidin-2-one as a white solid. MS ESI$^+$: m/z=304 [M+H]$^+$.

1-(2,4-Dimethoxybenzyl)-4,4-dimethyl-3-(4-(2,2,2-trifluoroethoxy)phenoxy)pyrrolidin-2-one To a solution of 4-(2,4-dimethoxybenzylamino)-2,2-dimethyl-4-oxo-3-(4-(2,2,2-trifluoroethoxy)phenoxy)butyl methanesulfonate (370 mg) in THF (10 mL) was added NaH (53 mg) at 0° C. After heating at 60° C. for four hours, the mixture was diluted with EA (50 mL) and H$_2$O (20 mL). The organic phase was washed with H$_2$O and brine, dried over Na$_2$SO$_4$, filtered and concentrated. The residue was purified by SGC (PE:EA=1:1) to provide 1-(2,4-dimethoxybenzyl)-4,4-dimethyl-3-(4-(2,2,2-trifluoroethoxy)phenoxy) pyrrolidin-2-one. MS ESI$^+$: m/z=454 [M+H]$^+$.

4-(2,4-Dimethoxybenzylamino)-2,2-dimethyl-4-oxo-3-(4-(2,2,2-trifluoroethoxy)phenoxy)butyl methanesulfonate To a mixture of N-(2,4-dimethoxybenzyl)-4-hydroxy-3,3-dimethyl-2-(4-(2,2,2-trifluoroethoxy)phenoxy)butanamide (310 mg) and Et$_3$N (134 mg) in DCM (10 mL) was added Ms-Cl (113 mg) at 0° C. After stirring for one hour at 0° C., the mixture was diluted with DCM (20 mL) and H$_2$O (10 mL). The organic phase was washed with H$_2$O and brine, dried over Na$_2$SO$_4$, filtered and concentrated to provide 4-(2,4-dimethoxybenzylamino)-2,2-dimethyl-4-oxo-3-(4-(2,2,2-trifluoroethoxy)phenoxy)butyl methanesulfonate. MS ESI$^+$: m/z=550 [M+H]$^+$.

N-(2,4-Dimethoxybenzyl)-4-hydroxy-3,3-dimethyl-2-(4-(2,2,2-trifluoroethoxy)phenoxy)butanamide A mixture of 4,4-dimethyl-3-(4-(2,2,2-trifluoroethoxy)phenoxy)dihydrofuran-2(3H)-one (220 mg) and (2,4-dimethoxyphenyl)methanamine (241 mg) in methanol (10 mL) was heated at reflux for 16 hours. The mixture was concentrated and the residue was purified by SGC (PE:EA=1:1) to provide N-(2,4-dimethoxybenzyl)-4-hydroxy-3,3-dimethyl-2-(4-(2,2,2-trifluoroethoxy)phenoxy)butanamide. MS ESI$^+$: m/z=472 [M+H]$^+$.

4,4-Dimethyl-3-(4-(2,2,2-trifluoroethoxy)phenoxy) dihydrofuran-2(3H)-one

To a mixture of 3-(4-hydroxyphenoxy)-4,4-dimethyldihydrofuran-2(3H)-one (1.6 g) and K$_2$CO$_3$ (3.0 g) in DMF (20 mL) was added slowly 2,2,2-trifluoroethyl trifluoromethanesulfonate (3.3 g). The mixture was stirred at RT for four hours. The mixture was diluted with water (100 mL), extracted with ethyl acetate (30 mL×2), washed with brine (50 mL) and dried over anhydrous Na$_2$SO$_4$. The crude product was purified by SGC (PE/EA=5:1) to provide 4,4-dimethyl-3-(4-(2,2,2-trifluoroethoxy)phenoxy)dihydrofuran-2(3H)-one. MS ESI$^+$: m/z=305 [M+H]$^+$.

3-(4-Hydroxyphenoxy)-4,4-dimethyldihydrofuran-2(3H)-one

A mixture of 3-(4-bromphenoxy)-4,4-dimethyldihydrofuran-2(3H)-one (2.8 g), bis(pinacolato)diboron (3.0 g), Pd(dppf)Cl$_2$*CH$_2$Cl$_2$ (800 mg) and KOAc (1.4 g) in 1,4-dioxane (100 mL) was stirred at 95° C. for 6 hours under nitrogen. After cooling to RT, the mixture was diluted with EA (100 mL) and filtered. The filtrate was concentrated and the residue was dissolved in THF (40 mL) and water (20 mL). Sodium perborate tetrahydrate (3.0 g) was added slowly at 0° C. After stirring at RT overnight, the mixture was diluted with water (50 mL) and extracted with ethyl acetate (100 mL×2). The combined organic layers were washed with brine (50 mL), dried over anhydrous $Na_2SO_4$, filtered and concentrated. The crude product was purified by SGC (EA in PE, 0 to 30%) to provide 3-(4-hydroxyphenoxy)-4,4-dimethyldihydrofuran-2(3H)-one. MS ESI$^+$: m/z=223 [M+H]$^+$.

3-(4-Bromophenoxy)-4,4-dimethyldihydrofuran-2 (3H)-one

A mixture of 3-(4-aminophenoxy)-4,4-dimethyldihydrofuran-2(3H)-one (3.5 g), $CuBr_2$ (3.5 g), tert-butyl nitrite (2.4 g) and MeCN (100 mL) was stirred for 30 minutes at 0° C. The mixture was heated at 60° C. for 4 hours. The mixture was concentrated and purified by SGC (PE:EA=5:1) to provide 3-(4-bromophenoxy)-4,4-dimethyldihydrofuran-2 (3H)-one. MS ESI$^+$: m/z=285 [M+H]$^+$.

3-(4-Aminophenoxy)-4,4-dimethyldihydrofuran-2 (3H)-one

To a solution of 4,4-dimethyl-3-(4-nitrophenoxy)dihydrofuran-2(3H)-one (4.0 g) in EA (150 mL) was added Pd/C (200 mg). The mixture was stirred under hydrogen for 16 hours at RT under atmospheric pressure. The mixture was filtered and concentrated to provide 3-(4-aminophenoxy)-4, 4-dimethyldihydrofuran-2(3H)-one. MS ESI$^+$: m/z=222 [M+H]$^+$.

4,4-Dimethyl-3-(4-nitrophenoxy)dihydrofuran-2 (3H)-one

To a mixture of 1-fluoro-4-nitro-benzene (4.0 g), 3-hydroxy-4,4-dimethyl-pyrrolidin-2-one (5.5 g) and DMF (20 mL) was added NaH (1.7 g). After stirring for 16 hours at RT, the mixture was diluted with $H_2O$ (100 mL) and EA (100 mL). The organic phase was washed with $H_2O$ and brine, dried over $Na_2SO_4$, filtered and concentrated. The residue was purified by SGC (PE/EA=1:4) to provide 4,4-dimethyl-3-(4-nitrophenoxy)dihydrofuran-2(3H)-one. MS ESI$^+$: m/z=252 [M+H]$^+$.

3-[6-(2,2,2-Trifluoro-ethoxy)-pyridin-3-ylmethyl]-pyrrolidin-2-one

To a solution of 3-[1-[6-(2,2,2-trifluoro-ethoxy)-pyridin-3-yl]-meth-(E)-ylidene]-pyrrolidin-2-one (410 mg) in ethanol (20 mL) was added Pd/C (50 mg). The mixture was stirred under hydrogen for 16 hours at atmospheric pressure. The mixture was filtered and concentrated. The residue was purified by SGC (DCM/MeOH=10:1) to provide 3-[6-(2,2, 2-trifluoro-ethoxy)-pyridin-3-ylmethyl]-pyrrolidin-2-one. MS ESI$^+$: m/z=275 [M+H]$^+$. The enantiomeric mixture can be separated by chiral HPLC (analytical column: Chiralpak AS-H/53, 4.6×250 mm; mobile phase: n-heptane:EtOH 1:2; flow rate: 1.0 mL/min; column temperature: 30° C., UV wavelength: 224 nm) to provide 3-[6-(2,2,2-trifluoro-ethoxy)-pyridin-3-ylmethyl]-pyrrolidin-2-one (enantiomer 1, $R_t$=5.18 min) and 3-[6-(2,2,2-trifluoro-ethoxy)-pyridin-3-ylmethyl]-pyrrolidin-2-one (enantiomer 2, $R_t$=9.55 min).

3-[1-[6-(2,2,2-Trifluoro-ethoxy)-pyridin-3-yl]-meth-(E)-ylidene]-pyrrolidin-2-one To a suspension of NaH (2.0 g) in THF (100 mL) was added a mixture of 1-acetyl-pyrrolidin-2-one (1.6 g), 6-(2, 2,2-trifluoro-ethoxy)-pyridine-3-carbaldehyde (2.6 g) and THF (5 mL) dropwise at ice-bath temperature. After the addition was complete, the reaction mixture was stirred for 10 min at ice-bath temperature. Acetic acid (5 mL) was slowly added dropwise to destroy the excess NaH. The reaction mixture was poured into ice-water and extracted with EA (100 mL×2). The combined organic layers were dried over $Na_2SO_4$, filtered and concentrated. The residue was purified by SGC (DCM/MeOH=20:1) to provide 3-[1-[6-(2,2,2-trifluoro-ethoxy)-pyridin-3-yl]-meth-(E)-ylidene]-pyrrolidin-2-one. MS ESI$^+$: m/z=273 [M+H]$^+$.

6-(2,2,2-Trifluoro-ethoxy)-pyridine-3-carbaldehyde

To a solution of [6-(2,2,2-trifluoro-ethoxy)-pyridin-3-yl]-methanol (2.7 g) in DCM (150 mL) was added $MnO_2$ (16.9 g). After stirring for 16 hours at RT, the mixture was filtered through a pad of Celite. The filtrate was concentrated in vacuo to provide 6-(2,2,2-trifluoro-ethoxy)-pyridine-3-carbaldehyde. MS ESI$^+$: m/z=206 [M+H]$^+$.

[6-(2,2,2-Trifluoro-ethoxy)-pyridin-3-yl]-methanol

To a stirred suspension of $LiAlH_4$ (501 mg) in THF (60 mL) at 0° C. was slowly added a solution of 6-(2,2,2-trifluoro-ethoxy)-nicotinic acid methyl ester (3.1 g) in THF (20 mL). After stirring for one hour at 0° C., NaOH (10% aq., 2 mL) and $Na_2SO_4$ were added. The resulting precipitate was removed by filtration through a pad of Celite and the filtrate was concentrated in vacuo to provide [6-(2,2,2-trifluoro-ethoxy)-pyridin-3-yl]-methanol. MS ESI$^+$: m/z=208 [M+H]$^+$.

6-(2,2,2-Trifluoro-ethoxy)-nicotinic acid methyl ester

To a stirred solution of 2,2,2-trifluoroethanol (4.2 g) in THF (100 mL) was added sodium hydride (60% dispersion in oil, 1680 mg). The reaction mixture was stirred at RT for 30 minutes prior to the addition of 6-chloronicotinic acid methyl ester (5.1 g) in THF (5 mL). The reaction mixture was heated at 70° C. for 1.5 hours, then partitioned between EtOAc (50 mL) and saturated ammonium chloride solution (50 mL). The aqueous layer was extracted with EtOAc (50 mL). The combined organic layers were dried (sodium sulphate), filtered and concentrated in vacuo. The resulting white solid was purified by SGC (PE/EA=5:1) to provide 6-(2,2,2-trifluoro-ethoxy)-nicotinic acid methyl ester. MS ESI$^+$: m/z=236 [M+H]$^+$.

3-(4-Cyclopropanecarbonyl-benzyl)-pyrrolidin-2-one

To a solution of 1-trimethylsilanyl-pyrrolidin-2-one (315 mg) in THF (10 mL) was added LiHMDS (2 mL, 1 M in THF) under a nitrogen atmosphere at −78° C. The reaction mixture was stirred at the same temperature for a further 10 minutes. Then, (4-bromomethyl-phenyl)-cyclopropyl-methanone (240 mg) was added, and the mixture was allowed to warm to RT and stirred for 16 hours. The reaction mixture was quenched with water and extracted with ethyl acetate. The organic layer was dried over $MgSO_4$. After filtration and removal of the solvent, the residue was purified by SGC (DCM/MeOH=20:1) to provide 3-(4-cyclopropanecarbonyl-benzyl)-pyrrolidin-2-one. MS ESI+: m/z=244 [M+H]+.

(4-Bromomethyl-phenyl)-cyclopropyl-methanone

To a mixture of cyclopropyl(p-tolyl)methanone (8.5 g) and chlorobenzene (40 mL) was added NBS (13.94 g) and AIBN (867 mg). The reaction mixture was stirred at 85° C. for 3 hours under argon. After cooling to RT, the reaction mixture was filtered and concentrated. The residue was dissolved in THF (30 mL). DIPEA (21.87 g) and diethyl phosphonate (20.36 g) were added. After stirring at 0° C. overnight, the solvent was removed and water (50 mL) was added. The mixture was extracted with EA (100 mL×3). The combined organic layers were dried over $Na_2SO_4$ and concentrated in vacuo. The crude product was recrystallized from PE to provide (4-bromomethyl-phenyl)-cyclopropyl-methanone. MS ESI+: m/z=241 [M+H]+.

Cyclopropyl(p-tolyl)methanone

To a mixture of cyclopropanecarbonyl chloride (10 g) and toluene (50 mL) was added $AlCl_3$ (14.05 g) slowly under argon at 0° C. After stirring at 0° C. for 1.5 hours, the mixture was poured into ice water. The mixture was extracted with EA (10 mL×3). The combined organic layers were dried over $Na_2SO_4$, concentrated in vacuo and the residue recrystallized from PE to provide cyclopropyl(p-tolyl)methanone. MS ESI+: m/z=161 [M+H]+.

(R)-3-(6-(Cyclopropanecarbonyl)pyridin-3-yloxy) pyrrolidin-2-one

A solution of cyclopropyl(5-hydroxypyridin-2-yl)methanone (4.0 g) in DCM (5 mL) was added (S)-3-hydroxypyrrolidin-2-one (2.97 g) and $PPh_3$ (9.13 g) at RT. After stirring for 30 minutes, DIAD (7.42 g) was added. The mixture was stirred at RT overnight. The reaction mixture was quenched with water (20 mL) and extracted by DCM (30 mL×3). The combined organic layers were washed with water and brine, dried over $Na_2SO_4$, filtered and concentrated. The residue was purified by silica gel chromatography (DCM/MeOH=10:1), and further purified by preparative HPLC to provide (R)-3-(6-(cyclopropanecarbonyl) pyridin-3-yloxy)pyrrolidin-2-one. MS ESI+: m/z=247 [M+H]+.

Cyclopropyl(5-hydroxypyridin-2-yl)methanone

To a solution of cyclopropyl(5-(triisopropylsilyloxy)pyridin-2-yl)methanone (2.4 g) in DCM (15 mL) was added TBAF (4.72 g). After stirring at RT for 2 hours, the reaction mixture was concentrated. The residue was purified by silica gel chromatography (DCM/MeOH=10:1) to provide cyclopropyl(5-hydroxypyridin-2-yl)methanone. MS ESI+: m/z=164 [M+H]+.

Cyclopropyl(5-(triisopropylsilyloxy)pyridin-2-yl) methanone

To a mixture of 5-(triisopropylsilyloxy)picolinonitrile (3.5 g) and THF (10 mL) was added cyclopropylmagnesium bromide (25.4 mL, 1 M) slowly under argon at 0° C. After stirring at 0° C. for 1.5 hours, the reaction mixture was diluted with $H_2O$ (50 mL) and extracted with EA (50 mL×3). The combined organic layers were dried over $Na_2SO_4$ and concentrated in vacuo to provide cyclopropyl(5-(triisopropylsilyloxy)pyridin-2-yl)methanone. MS ESI+: m/z=320 [M+H]+.

5-(Triisopropylsilyloxy)picolinonitrile

A solution of 5-hydroxy-pyridine-2-carbonitrile (44.6 g) in DCM (300 mL) was added TIPS-Cl (40.3 g) and $Et_3N$ (23.4 g) at RT. The mixture was stirred at this temperature overnight. The solvent was distilled off under reduced pressure to provide 5-(triisopropylsilyloxy)picolinonitrile. MS ESI+: m/z=277 [M+H]+.

(R)-3-(4-(Cyclopropanecarbonyl)-3-fluorophenoxy) pyrrolidin-2-one

Following Typical Procedure 3, cyclopropyl(2-fluoro-4-hydroxyphenyl)methanone and (S)-3-hydroxypyrrolidin-2-one were reacted to provide (R)-3-(4-(cyclopropanecarbonyl)-3-fluorophenoxy)pyrrolidin-2-one. MS ESI+: m/z=264 [M+H]+.

Cyclopropyl(2-fluoro-4-hydroxyphenyl)methanone

To a solution of 4-((tert-butyldimethylsilyl)oxy)-2-fluorobenzonitrile (2.0 g) in THF (1 mL) was added cyclopropylmagnesium bromide (32 mL, 0.5 M in THF) slowly under argon at 0° C. The mixture was heated at reflux for 16 hours. After cooling to RT, a solution of NaOH in MeOH/water was added. After 20 minutes, the mixture was acidified and extracted with EA (200 mL×2). The combined organic layers were dried over $Na_2SO_4$ and concentrated in vacuo to provide cyclopropyl(2-fluoro-4-hydroxyphenyl) methanone. MS ESI+: m/z=181 [M+H]+.

4-((Tert-butyldimethylsilyl)oxy)-2-fluorobenzonitrile

To a mixture of 2-fluoro-4-hydroxybenzonitrile (5.0 g), imidazole (5.0 g) and DMF (50 mL) was added tert-butylchlorodimethylsilane (8.24 g) in DMF (20 mL) at 0° C. within 13 minutes. The mixture was extracted with PE (200 mL×2). The extracts were concentrated in vacuo to provide 4-((tert-butyldimethylsilyl)oxy)-2-fluorobenzonitrile. MS ESI+: m/z=252 [M+H]+.

3-(4-Cyclopropanecarbonyl-phenoxy)-4,4-dimethyl-pyrrolidin-2-one

To a solution of 3-(4-cyclopropanecarbonyl-phenoxy)-1-(4-methoxy-benzyl)-4,4-dimethyl-pyrrolidin-2-one (500 mg) in MeCN/$H_2O$ (50 mL/50 mL) was added CAN (2.0 g) at RT. The mixture was stirred for 4 hours at RT. An aqueous saturated solution of $Na_2CO_3$ (50 mL) was added, and the mixture extracted with EA (50 mL×3). The combined organic layers were dried over $Na_2SO_4$ and concentrated under vacuum. The residue was purified by silica gel chromatography (20 to 50% EA in PE) to provide 3-(4-cyclopropanecarbonyl-phenoxy)-4,4-dimethyl-pyrrolidin-2-one. MS ESI+: m/z=274 [M+H]+.

3-(4-Cyclopropanecarbonyl-phenoxy)-1-(4-methoxy-benzyl)-4,4-dimethyl-pyrrolidin-2-one To a solution of 4-[1-(4-methoxy-benzyl)-4,4-dimethyl-2-oxo-pyrrolidin-3-yloxy]-benzonitrile (240 mg) in THF (10 mL) was added bromo(cyclopropyl)magnesium (10 mL, 1 M). The mixture was stirred overnight at RT. The mixture was quenched with HCl (0.5 M, 20 mL), and extracted with EA (20 mL×3). The organic layer was washed with brine, dried over Na$_2$SO$_4$ and concentrated under vacuum. The residue was purified by preparative HPLC to provide 3-(4-cyclopropanecarbonyl-phenoxy)-1-(4-methoxy-benzyl)-4,4-dimethyl-pyrrolidin-2-one. MS ESI$^+$: m/z=394 [M+H]$^+$.

4-[1-(4-Methoxy-benzyl)-4,4-dimethyl-2-oxo-pyrrolidin-3-yloxy]-benzonitrile

To a solution of 3-hydroxy-1-(4-methoxy-benzyl)-4,4-dimethyl-pyrrolidin-2-one (50 mg) and 4-fluoro-benzonitrile (29.2 mg) in MeCN (5 mL) was added Cs$_2$CO$_3$ (200 mg) at RT. The mixture was stirred overnight at 60° C. After cooling to RT, the mixture was filtered. The filtrate was concentrated under vacuum. The residue was purified by preparative TLC to provide 4-[1-(4-methoxy-benzyl)-4,4-dimethyl-2-oxo-pyrrolidin-3-yloxy]-benzonitrile. MS ESI$^+$: m/z=351 [M+H]$^+$.

3-(6-Cyclopropanecarbonyl-pyridin-3-yloxy)-4,4-dimethyl-pyrrolidin-2-one

To a solution of 3-(6-cyclopropanecarbonyl-pyridin-3-yloxy)-1-(4-methoxy-benzyl)-4,4-dimethyl-pyrrolidin-2-one (200 mg) in MeCN/H$_2$O (20 mL/20 mL) was added CAN (1.0 g) at RT. The mixture was stirred for 4 hours at RT. An aqueous saturated solution of Na$_2$CO$_3$ (20 mL) was added and the mixture extracted with EA (50 mL×3). The combined organic layers were dried over Na$_2$SO$_4$ and concentrated under vacuum. The residue was purified by silica gel chromatography (20 to 50% EA in PE) to provide 3-(6-cyclopropanecarbonyl-pyridin-3-yloxy)-4,4-dimethyl-pyrrolidin-2-one. MS ESI$^+$: m/z=275 [M+H]$^+$.

3-(6-Cyclopropanecarbonyl-pyridin-3-yloxy)-1-(4-methoxy-benzyl)-4,4-dimethyl-pyrrolidin-2-one To a solution of 5-[1-(4-methoxy-benzyl)-4,4-dimethyl-2-oxo-pyrrolidin-3-yloxy]-pyridine-2-carbonitrile (300 mg) in THF (10 mL) was added bromo(cyclopropyl)magnesium (5 mL, 1 M). The mixture was stirred overnight at RT. The mixture was quenched with HCl (0.5 M, 20 mL), and extracted with EA (20 mL×3). The organic layer was washed with brine, dried over Na$_2$SO$_4$ and concentrated under vacuum. The residue was purified by silica gel chromatography (10 to 20% EA in PE) to provide 3-(6-cyclopropanecarbonyl-pyridin-3-yloxy)-1-(4-methoxy-benzyl)-4,4-dimethyl-pyrrolidin-2-one. MS ESI$^+$: m/z=395 [M+H]$^+$.

5-[1-(4-Methoxy-benzyl)-4,4-dimethyl-2-oxo-pyrrolidin-3-yloxy]-pyridine-2-carbonitrile To a solution of 3-hydroxy-1-(4-methoxy-benzyl)-4,4-dimethyl-pyrrolidin-2-one (50 mg) and 5-fluoropyridine-2-carbonitrile (29.3 mg) in MeCN (5 mL) was added Cs$_2$CO$_3$ (0.2 g) at RT. The mixture was stirred overnight at 60° C. The mixture was filtered. The filtrate was concentrated under vacuum. The residue was purified by preparative TLC to provide 5-[1-(4-methoxy-benzyl)-4,4-dimethyl-2-oxo-pyrrolidin-3-yloxy]-pyridine-2-carbonitrile. MS ESI$^+$: m/z=352 [M+H]$^+$.

Preparation of Aryl Bromides

5-Bromo-2-(3-hydroxyazetidine-1-yl)nicotinonitrile (Typical Procedure 2)

A mixture of 5-bromo-2-chloro-nicotinonitrile (1.9 g), azetidin-3-ol (965 mg), K$_2$CO$_3$ (6.1 g) and DMF (20 mL) was stirred at RT under nitrogen atmosphere overnight. The mixture was diluted with EA (200 mL). The diluted mixture was washed with H$_2$O (50 mL×3), brine (50 mL×2) and the organic layer dried over Na$_2$SO$_4$. After filtration and evaporation of the solvent, the residue was purified by SGC (PE/EA=6:1) to provide 5-bromo-2-(3-hydroxyazetidine-1-yl)nicotinonitrile. MS ESI$^+$: m/z=256 [M+H]$^+$.

Using essentially the Typical Procedure 2, the following compounds were obtained:
1-(5-Bromo-3-fluoro-pyridin-2-yl)-azetidin-3-ol from 5-bromo-2,3-difluoro-pyridine and azetidin-3-ol;
1-(5-bromo-3-fluoro-pyridin-2-yl)-azetidine-3-carboxylic acid dimethylamide from 5-bromo-2,3-difluoro-pyridine and azetidine-3-carboxylic acid dimethylamide (hydrochloride); and
1-(5-bromo-3-cyano-pyridin-2-yl)-azetidine-3-carboxylic acid dimethylamide from 5-bromo-2-chloro-nicotinonitrile and azetidine-3-carboxylic acid dimethylamide (hydrochloride).

1-(5-Bromo-pyridin-2-yl)-azetidine-3-carboxylic acid dimethylamide

A mixture of 1-(5-bromo-pyridin-2-yl)-azetidine-3-carboxylic acid (1.23 g), HATU (2.73 g), DIPEA (1.85 g) and DMF (50 mL) was stirred at RT for 20 minutes, then dimethylamine hydrochloride (780 mg) was added. The solution was stirred at RT for 4 hours. The reaction mixture was diluted with EA (200 mL), and washed with water (100 mL×2) and brine (100 mL). The organic layer was dried over anhydrous Na$_2$SO$_4$, filtered and concentrated to get the crude product, which was purified by column chromatography on silica gel eluting with DCM/MeOH (50:1) to provide 1-(5-bromo-pyridin-2-yl)-azetidine-3-carboxylic acid dimethylamide. MS ESI$^+$: m/z=284 [M+H]$^+$.

1-(5-Bromo-pyridin-2-yl)-azetidine-3-carboxylic acid

A solution of 1-(5-bromo-pyridin-2-yl)-azetidine-3-carboxylic acid methyl ester (1.5 g) in THF (35 mL) and H$_2$O (15 mL) was added LiOH.H$_2$O (4.65 g) and the resultant mixture was stirred at RT for two hours. The reaction mixture was acidified with HCl (1 M), diluted with EA (200 mL), and washed with water (100 mL×3) and brine (100 mL). The organic layer was dried over anhydrous Na$_2$SO$_4$, filtered and concentrated to provide 1-(5-bromo-pyridin-2-yl)-azetidine-3-carboxylic acid. MS ESI$^+$: m/z=257 [M+H]$^+$.

1-(5-Bromo-pyridin-2-yl)-azetidine-3-carboxylic acid methyl ester

A mixture of 5-bromo-2-fluoropyridine (3.72 g), methyl azetidine-3-carboxylate hydrochloride (4.8 g), K$_2$CO$_3$ (11.65 g) and DMF (50 mL) was heated under stirring to 70° C. for 5 hours. After cooling to RT, the mixture was poured into HCl (2 N, 30 mL) and the aqueous phase was extracted with EtOAc (200 mL×3). The combined organic phases were washed with NaHCO$_3$ solution (50 mL×3) and water. The organic layer was dried over anhydrous Na$_2$SO$_4$, filtered and concentrated to get a crude product, which was purified by column chromatography on silica gel eluting with PE/EA (10:1) to provide 1-(5-bromo-pyridin-2-yl)-azetidine-3-carboxylic acid methyl ester. MS ESI$^+$: m/z=271 [M+H]$^+$.

1-(5-Bromo-pyrimidin-2-yl)-azetidine-3-carboxylic acid dimethylamide

A mixture of 1-(5-bromo-pyrimidin-2-yl)-azetidine-3-carboxylic acid methyl ester (7.0 g), liquid dimethylamine (12 mL) and methanol (7 mL) was heated to 65° C. in a sealed vial overnight. After cooling to RT, the mixture was concentrated in vacuo and the residue was washed with EA (40 mL) to provide 1-(5-bromo-pyrimidin-2-yl)-azetidine-3-carboxylic acid dimethylamide. MS ESI$^+$: m/z=287 [M+H]$^+$.

1-(5-Bromo-pyrimidin-2-yl)-azetidine-3-carboxylic acid methyl ester

A mixture of 5-bromo-2-chloro-pyrimidine (50.0 g), azetidine-3-carboxylic acid methyl ester (hydrochloride, 50.94 g), potassium carbonate (107.18 g) and DMSO (250 mL) was stirred at 95° C. overnight. The mixture was diluted with water (2500 mL) and extracted with EtOAc (400 mL×3). The combined organic layers were washed with brine (800 mL), dried (Na$_2$SO$_4$), filtrated and concentrated in vacuo. The solid obtained, was washed with EA (80 mL) to provide 1-(5-bromo-pyrimidin-2-yl)-azetidine-3-carboxylic acid methyl ester. MS ESI$^+$: m/z=274 [M+H]$^+$.

5-Bromo-2-(3-(methylsulfinyl)azetidin-1-yl)pyrimidine

Hydrogen peroxide (30% aq., 1.4 g) was added to a solution of 5-bromo-2-(3-methylsulfanyl-azetidin-1-yl)-pyrimidine (2.1 g) in AcOH (40 mL). The reaction mixture was stirred at RT for 16 hours. A solution of Na$_2$S$_2$O$_3$ (200 mg) in H$_2$O (2 mL) was added. After stirring for 10 minutes, the mixture was diluted with H$_2$O (200 mL) and extracted with DCM (50 mL×3). The combined organic layers were washed with H$_2$O, saturated NaHCO$_3$ solution and brine, dried over Na$_2$SO$_4$, filtered and concentrated. The residue was purified by SGC (DCM/MeOH=15:1) to provide 5-bromo-2-(3-(methylsulfinyl)azetidin-1-yl)pyrimidine as a mixture of enantiomers. MS ESI$^+$: m/z=276 [M+H]$^+$. The enantiomers were separated by chiral preparative SFC (instrument: SFC-200 (Thar, Waters), column: SC 20*250 mm (5 μm, Decial), column temperature: 35° C., mobile phase: CO$_2$/methanol (0.1% NH$_4$OH)=75:25, flow rate: 120 g/min, back pressure: 100 bar, UV detection wavelength: 214 nm, cycle time: 1.5 min, sample solution: 1600 mg dissolved in 180 mL methanol, injection volume: 1.8 mL) to provide 5-bromo-2-(3-(methylsulfinyl)azetidin-1-yl)pyrimidine (enantiomer 1, R$_t$=1.98 min) and 5-bromo-2-(3-(methylsulfinyl)azetidin-1-yl)pyrimidine (enantiomer 2, R$_t$=2.34 min).

5-Bromo-2-(3-methylsulfanyl-azetidin-1-yl)-pyrimidine

Sodium methanethiolate (610 mg) was added to a solution of 1-(5-bromopyrimidin-2-yl)azetidin-3-yl methanesulfonate (1.4 g) in DMF (20 mL). The mixture was stirred at 80° C. for 2 hours. After cooling to RT, the mixture was diluted with EA (100 mL) and H$_2$O (100 mL). The organic phase was washed with H$_2$O and brine, dried over Na$_2$SO$_4$, filtered and concentrated. The residue was purified by SGC (PE/EA=1:4) to provide 5-bromo-2-(3-methylsulfanyl-azetidin-1-yl)-pyrimidine. MS ESI$^+$: m/z=260 [M+H]$^+$.

1-(5-Bromopyrimidin-2-yl)azetidin-3-yl methanesulfonate

To a mixture of 1-(5-bromopyrimidin-2-yl)azetidin-3-ol (1.0 g), Et$_3$N (880 mg) and DCM (30 mL) was added Ms-Cl (74.7 mg) at 0° C. After stirring at 0° C. for one hour, the mixture was diluted with DCM (50 mL) and saturated NaHCO$_3$ solution (20 mL). The organic phase was washed with H$_2$O and brine, dried over Na$_2$SO$_4$, filtered and concentrated to provide 1-(5-bromopyrimidin-2-yl)azetidin-3-yl methanesulfonate. MS ESI$^+$: m/z=308 [M+H]$^+$.

1-(5-Bromopyrimidin-2-yl)azetidin-3-ol

A mixture of 5-bromo-2-chloro-pyrimidine (3.0 g), azetidin-3-ol (1.7 g), DIPEA (5.0 g) and DMSO (10 mL) was heated at 80° C. for 16 hours. The mixture was diluted with H$_2$O (100 mL) and EA (200 mL). The organic phase was washed with H$_2$O and brine, dried over Na$_2$SO$_4$, filtered and concentrated. The residue was washed with PE/EA (4:1, 30 mL) and filtered to provide 1-(5-bromopyrimidin-2-yl)azetidin-3-ol. MS ESI$^+$: m/z=230 [M+H]$^+$.

5-Bromo-2-(3-methanesulfonyl-azetidin-1-yl)-pyrimidine

To a mixture of 5-bromo-2-(3-methylsulfanyl-azetidin-1-yl)-pyrimidine (500 mg) and DCM (5 mL) was added MCPBA (665 mg) in small portions. After stirring at RT for 16 hours, the mixture was diluted with EA (50 mL), washed with saturated Na$_2$CO$_3$ solution, water and brine. The organic layer was dried over Na$_2$SO$_4$, filtered and concentrated.

The residue was purified by preparative HPLC to provide 5-bromo-2-(3-methanesulfonyl-azetidin-1-yl)-pyrimidine. MS ESI$^+$: m/z=292 [M+H]$^+$.

2-(5-Bromo-pyrimidin-2-yl)-2,6-diaza-spiro[3.4]octan-5-one

A solution of 2,6-diaza-spiro[3.4]octan-5-one (1.2 g), 5-bromo-2-chloropyrimidine (1.16 g) and DIPEA (2 mL) in DMSO (15 mL) was stirred overnight at 60° C. The mixture was cooled to RT, poured into water (80 mL) and extracted with EA (100 mL×2). The combined organic layers were washed with water (100 mL×3), dried over Na$_2$SO$_4$ and concentrated under vacuum. The residue was crystallized from EA (10 mL) to provide 2-(5-bromo-pyrimidin-2-yl)-2,6-diaza-spiro[3.4]octan-5-one. MS ESI$^+$: m/z=283 [M+H]$^+$.

2,6-Diaza-spiro[3.4]octan-5-one

To a solution of 5-oxo-2,6-diaza-spiro[3.4]octane-2-carboxylic acid tert-butyl ester (2.0 g) in DCM (15 mL) was added TFA (15 mL). The mixture was concentrated under vacuum to provide 2,6-diaza-spiro[3.4]octan-5-one. MS ESI$^+$: m/z=127 [M+H]$^+$.

5-Oxo-2,6-diaza-spiro[3.4]octane-2-carboxylic acid tert-butyl ester

To a solution of 3-(2-hydroxyimino-ethyl)-azetidine-1,3-dicarboxylic acid 1-tert-butyl ester 3-methyl ester (1.3 g) in MeOH (10 mL) was added Raney Ni (100 mg). The mixture was stirred under hydrogen overnight at RT. The solid was filtered. The filtrate was concentrated under vacuum. The residue was dissolved in EA (50 mL), washed with HCl (0.5

N, 50 mL) and brine (50 mL), then dried over Na$_2$SO$_4$, filtered and concentrated. The residue was crystallized from EtOAc (5 mL) to provide 5-oxo-2,6-diaza-spiro[3.4]octane-2-carboxylic acid tert-butyl ester. MS ESI$^+$: m/z=171 [M+H–tBu]$^+$.

3-(2-Hydroxyimino-ethyl)-azetidine-1,3-dicarboxylic acid 1-tert-butyl ester 3-methyl ester A solution of 3-(2-oxo-ethyl)-azetidine-1,3-dicarboxylic acid 1-tert-butyl ester 3-methyl ester (3.0 g) and NH$_2$OH (1.2 g) in MeOH (30 mL) was stirred overnight at RT. The mixture was concentrated to remove the solvent and dissolved in EA (50 mL). The mixture was washed with HCl (0.2 N, 10 mL×3) and brine, dried over Na$_2$SO$_4$, and the concentrated filtrate was purified by SGC (PE/EA 4:1 to 1:1) to provide 3-(2-hydroxyimino-ethyl)-azetidine-1,3-dicarboxylic acid 1-tert-butyl ester 3-methyl ester. MS ESI$^+$: m/z=273 [M+H]$^+$.

3-(2-Oxo-ethyl)-azetidine-1,3-dicarboxylic acid 1-tert-butyl ester 3-methyl ester A mixture of 3-allyl-azetidine-1,3-dicarboxylic acid 1-tert-butyl ester 3-methyl ester (3.0 g), NaIO$_4$ (6.3 g) and OsO$_4$ (300 mg) in THF/H$_2$O (50 mL/50 mL) was stirred overnight at RT. The mixture was concentrated under vacuum. The residue was dissolved in EA (50 mL) and water (50 mL). The organic layer was separated, dried over Na$_2$SO$_4$, concentrated under vacuum to provide 3-(2-oxo-ethyl)-azetidine-1,3-dicarboxylic acid 1-tert-butyl ester 3-methyl ester.

3-Allyl-azetidine-1,3-dicarboxylic acid 1-tert-butyl ester 3-methyl ester

To a solution of azetidine-1,3-dicarboxylic acid 1-tert-butyl ester 3-methyl ester (3.6 g) in THF (40 mL) at −78° C. was added dropwise a solution of LiHMDS (1 M, 20 mL). After 10 minutes at −78° C., allyl bromide (2.2 mL) was added. The mixture was stirred at 20° C. for 17 hours and then concentrated under vacuum. The residue was partioned between water (40 mL) and ethyl acetate (3×40 mL). The combined organic layers were dried (MgSO$_4$), and the concentrated filtrate was purified by SGC (PE/EA 90:10 to 80:20) to provide 3-allyl-azetidine-1,3-dicarboxylic acid 1-tert-butyl ester 3-methyl ester.

2-(5-Bromo-pyrimidin-2-yl)-6-methyl-2,6-diaza-spiro[3.4]octan-5-one

A solution of 6-methyl-2,6-diaza-spiro[3.4]octan-5-one (1.3 g), 5-bromo-2-chloropyrimidine (1.16 g) and DIPEA (2 mL) in DMSO (15 mL) was stirred overnight at 60° C. The mixture was cooled to RT, poured into water (80 mL) and extracted with EA (100 mL×2). The organic layer was washed with water (100 mL×3), dried over Na$_2$SO$_4$ and concentrated under vacuum. The residue was crystallized from EA (10 mL) to provide 2-(5-bromo-pyrimidin-2-yl)-6-methyl-2,6-diaza-spiro[3.4]octan-5-one. MS ESI$^+$: m/z=297 [M+H]$^+$.

6-Methyl-2,6-diaza-spiro[3.4]octan-5-one

To a solution of 6-methyl-5-oxo-2,6-diaza-spiro[3.4]octane-2-carboxylic acid tert-butyl ester (1.7 g) in DCM (15 mL) was added TFA (15 mL). The mixture was concentrated under vacuum to provide 6-methyl-2,6-diaza-spiro[3.4]octan-5-one. MS ESI$^+$: m/z=141 [M+H]$^+$.

6-Methyl-5-oxo-2,6-diaza-spiro[3.4]octane-2-carboxylic acid tert-butyl ester To a solution of 5-oxo-2,6-diaza-spiro[3.4]octane-2-carboxylic acid tert-butyl ester (1.6 g) in DMF (20 mL) was added NaH (340 mg) at ice-bath temperature. The mixture was stirred for 30 minutes. Methyl iodide (2.2 g) was added. The mixture was stirred for one hour at RT, poured into water (100 mL) and extracted with EA (50 mL×3). The combined organic layers were washed with water (100 mL×3), brine (50 mL), dried over Na$_2$SO$_4$ and concentrated under vacuum to provide 6-methyl-5-oxo-2,6-diaza-spiro[3.4]octane-2-carboxylic acid tert-butyl ester. MS ESI$^+$: m/z=185 [M+H–tBu]+.

5-Bromo-2-(3-isopropylsulfanyl-azetidin-1-yl)-pyrimidine

A mixture of methanesulfonic acid 1-(5-bromo-pyrimidin-2-yl)-azetidin-3-yl ester (3.0 g), propane-2-thiol (1.9 g) and K$_2$CO$_3$ (4.0 g) in DMF (40 mL) was heated at 80° C. for 16 hours in a sealed tube. The reaction mixture was then quenched with water and extracted with ethyl acetate (100 mL×2). The organic layer was then dried over MgSO$_4$. After removal of the solvent, the residue was purified by SGC (PE/EA=20:1) to provide 5-bromo-2-(3-isopropylsulfanyl-azetidin-1-yl)-pyrimidine. MS ESI$^+$: m/z=288 [M+H]$^+$.

5-Bromo-2-[3-(propane-2-sulfinyl)-azetidin-1-yl]-pyrimidine

To a solution of 5-bromo-2-(3-isopropylsulfanyl-azetidin-1-yl)-pyrimidine (6.8 g) in HOAc (50 mL) was added H$_2$O$_2$ (30%, 4.0 g) dropwise. After stirring for 16 hours, the reaction mixture was quenched with saturated Na$_2$S$_2$O$_3$ solution (20 mL) and extracted with DCM (100 mL×3). The organic layer was washed with saturated NaHCO$_3$ solution and dried over MgSO$_4$. After removal of the solvent, the residue was triturated with PE/EA (1:1) and the precipitate filtrated to provide 5-bromo-2-[3-(propane-2-sulfinyl)-azetidin-1-yl]-pyrimidine as a mixture of enantiomers. MS ESI$^+$: m/z=304 [M+H]$^+$. The enantiomers were separated by chiral preparative SFC (instrument: SFC-200 (Thar, Waters), column: SC 20*250 mm (5 µm, Decial), column temperature: 35° C., mobile phase: CO$_2$/methanol (0.1% NH$_4$OH)=75:25, flow rate: 120 g/min, back pressure: 100 bar, UV detection wavelength: 214 nm, cycle time: 1.5 min, sample solution: 1600 mg dissolved in 180 mL methanol, injection volume: 1.8 mL) to provide 5-bromo-2-[3-(propane-2-sulfinyl)-azetidin-1-yl]-pyrimidine (enantiomer 1, R$_f$=2.38 min) and 5-bromo-2-[3-(propane-2-sulfinyl)-azetidin-1-yl]-pyrimidine (enantiomer 2, R$_f$=2.96 min).

5-Bromo-2-[3-(propane-2-sulfonyl)-azetidin-1-yl]-pyrimidine

To a solution of 5-bromo-2-(3-isopropylsulfanyl-azetidin-1-yl)-pyrimidine (600 mg) in DCM (20 mL) was added MCPBA (1346 mg). The mixture was stirred for 2 hours at RT. Saturated Na$_2$S$_2$O$_3$ solution (10 mL) was added. After stirring for 10 minutes, the mixture was diluted with DCM (20 mL). The organic phase was washed with saturated NaHCO$_3$ solution (20 mL×3), H$_2$O, dried over Na$_2$SO$_4$, filtered and concentrated. The residue was purified by SGC (PE/EA=1:3) to provide 5-bromo-2-[3-(propane-2-sulfonyl)-azetidin-1-yl]-pyrimidine. MS ESI+: m/z=320 [M+H]+.

[1-(5-Bromo-pyrimidin-2-yl)-azetidin-3-yl]-acetic acid methyl ester

To a mixture of azetidin-3-yl-acetic acid methyl ester (hydrochloride, 759 mg) and 5-bromo-2-chloro-pyrimidine (1.07 g) in DMSO (10 mL) was added DIPEA (1.78 g) slowly at RT. The reaction mixture was stirred at 60° C. for 4 hours. After cooling to room temperature, water (30 mL) was added. The mixture was extracted with EA (30 mL×3). The combined organic layers were dried over $Na_2SO_4$, filtered and concentrated in vacuo. The residue was purified by silica gel chromatography (EtOAc/n-hexane=1:5) to provide [1-(5-bromo-pyrimidin-2-yl)-azetidin-3-yl]-acetic acid methyl ester. MS ESI+: m/z=288 [M+H]+.

2-[1-(5-Bromo-pyrimidin-2-yl)-azetidin-3-yl]-N,N-dimethyl-acetamide

To a solution of [1-(5-bromo-pyrimidin-2-yl)-azetidin-3-yl]-acetic acid methyl ester (1.1 g) in MeOH (10 mL) was added dimethylamine (0.91 g) in a sealable vial under argon at RT. The mixture was stirred at 75° C. for 2 hours. After cooling to RT, the mixture was concentrated in vacuo and the residue washed with EA to provide 2-[1-(5-bromo-pyrimidin-2-yl)-azetidin-3-yl]-N,N-dimethyl-acetamide. MS ESI+: m/z=299 [M+H]+.

1-[1-(5-Bromo-pyrimidin-2-yl)-azetidin-3-yl]-pyrrolidin-2-one

A solution of N-[1-(5-bromo-pyrimidin-2-yl)-azetidin-3-yl]-4-chloro-butyramide (0.2 g) in THF (20 mL) was cooled to 0° C. NaOH (50 mg) was added and the mixture was slowly warmed to 25° C. and stirred for 2 hours. The mixture was diluted with water and extracted with DCM (3×20 mL). The combined organic layers were dried, concentrated and purified by silica gel chromatography (0 to 10% MeOH in DCM) to provide 1-[1-(5-bromo-pyrimidin-2-yl)-azetidin-3-yl]-pyrrolidin-2-one. MS ESI+: m/z=299 [M+H]+.

N-[1-(5-Bromo-pyrimidin-2-yl)-azetidin-3-yl]-4-chloro-butyramide

To a solution of 1-(5-bromo-pyrimidin-2-yl)-azetidin-3-ylamine (300 mg) and TEA (0.53 mL) in DCM (10 mL) was added 4-chlorobutanoyl chloride (203 mg) at 0° C. The resulting mixture was stirred for 16 hours, quenched with $H_2O$ and extracted with DCM. The combined organic extracts were washed with brine then dried ($Na_2SO_4$) and concentrated in vacuo to provide N-[1-(5-bromo-pyrimidin-2-yl)-azetidin-3-yl]-4-chloro-butyramide. MS ESI+: m/z=334 [M+H]+.

1-(5-Bromo-pyrimidin-2-yl)-azetidin-3-ylamine

To a solution of [1-(5-bromo-pyrimidin-2-yl)-azetidin-3-yl]-carbamic acid tert-butyl ester (600 mg) in DCM (15 mL) was added TFA (10 mL). The mixture was stirred for one hour at RT. The mixture was concentrated to dryness under vacuum. The residue was dissolved in water (10 mL), neutralized with an aqueous solution of $Na_2CO_3$ (final pH=9). The aqueous layer was extracted with EA (10 mL×2). Water was removed by freeze drying. The residue was suspended with DCM (50 mL). The suspension was filtered to remove the salt and the filtrate was concentrated to provide 1-(5-bromo-pyrimidin-2-yl)-azetidin-3-ylamine. MS ESI+: m/z=230 [M+H]+.

[1-(5-Bromo-pyrimidin-2-yl)-azetidin-3-yl]-carbamic acid tert-butyl ester

A solution of azetidin-3-yl-carbamic acid tert-butyl ester (4.5 g), 5-bromo-2-chloro-pyrimidine (5.5 g) and DIPEA (7.5 mL) in DMSO (50 mL) was stirred overnight at 80° C. The mixture was cooled to RT, poured into water (300 mL) and extracted with EA (400 mL×2). The organic layer was washed with water (600 mL×3), dried over $Na_2SO_4$ and concentrated under vacuum. The residue was crystallized from EA (50 mL) to provide [1-(5-bromo-pyrimidin-2-yl)-azetidin-3-yl]-carbamic acid tert-butyl ester. MS ESI+: m/z=329 [M+H]+.

Preparation of Compounds of Table 2

Compound 2-01

A mixture of 1-[5-((S)-3-hydroxy-2-oxo-pyrrolidin-1-yl)-pyrimidin-2-yl]-azetidine-3-carboxylic acid dimethylamide (60 mg), cyclopropyl-(4-hydroxy-phenyl)-methanone (35 mg), triphenyl-phosphine (polymer-bound, 2.4 mmol/g, 82 mg), and DCM (3 mL) was kept at RT for 15 minutes. DIAD (40 mg) was added. The mixture was allowed to stand at RT for 12 hours, diluted with MeOH and filtered. The filtrate was concentrated to provide a residue, which was purified by preparative HPLC to provide Compound 2-01. Following essentially this procedure, the Compounds 2-01 to 2-11 in Table 2 were obtained by reacting 1-[5-((S)-3-hydroxy-2-oxo-pyrrolidin-1-yl)-pyrimidin-2-yl]-azetidine-3-carboxylic acid dimethylamide with the respective substituted phenol or hydroxy-pyridine. DIAD may be substituted by DEAD. DCM may be substituted by THF, or a mixture of both solvents.

TABLE 2

| Comp. | Structure | LCMS Method | R$_t$ [min] | ESI+ m/z [amu] |
|---|---|---|---|---|
| 2-01 | 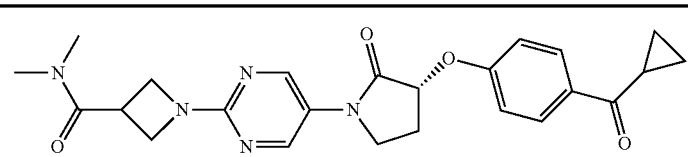 | B | 1.46 | 450.2 |

TABLE 2-continued

| Comp. | Structure | LCMS Method | R$_t$ [min] | ESI$^+$ m/z [amu] |
|---|---|---|---|---|
| 2-02 | 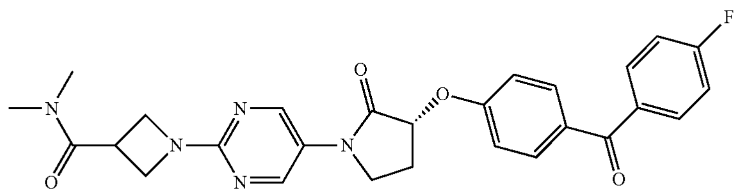 [SMILES: CN(C)C(=O)C1CN(c2ncc(N3CC[C@@H](Oc4ccc(C(=O)c5ccc(F)cc5)cc4)C3=O)cn2)C1] | B | 1.61 | 504.2 |
| 2-03 | 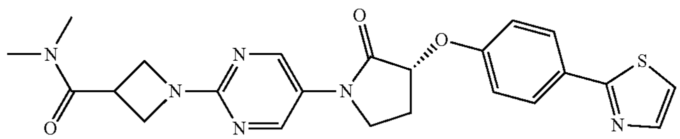 [SMILES: CN(C)C(=O)C1CN(c2ncc(N3CC[C@@H](Oc4ccc(-c5nccs5)cc4)C3=O)cn2)C1] | B | 1.46 | 465.2 |
| 2-04 | 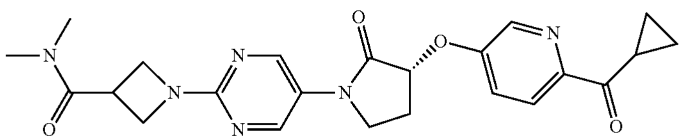 [SMILES: CN(C)C(=O)C1CN(c2ncc(N3CC[C@@H](Oc4ccc(C(=O)C5CC5)nc4)C3=O)cn2)C1] | B | 1.40 | 451.1 |
| 2-05 | 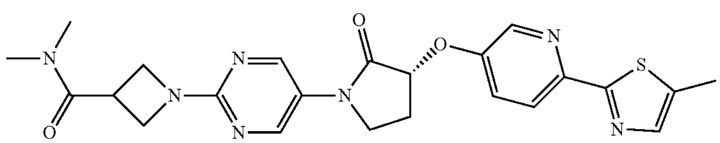 | B | 1.47 | 480.3 |
| 2-06 | 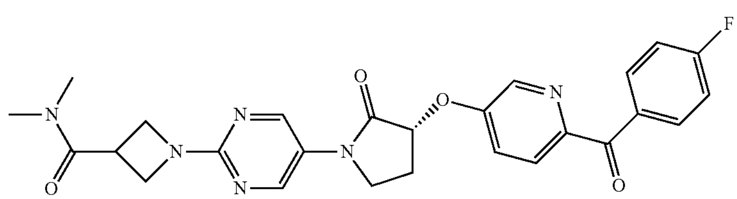 [SMILES: CN(C)C(=O)C1CN(c2ncc(N3CC[C@@H](Oc4ccc(C(=O)c5ccc(F)cc5)nc4)C3=O)cn2)C1] | B | 1.54 | 505.3 |
| 2-07 | 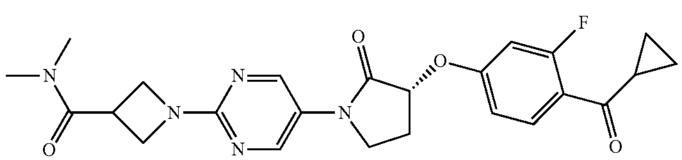 [SMILES: CN(C)C(=O)C1CN(c2ncc(N3CC[C@@H](Oc4ccc(C(=O)C5CC5)c(F)c4)C3=O)cn2)C1] | B | 1.52 | 468.3 |
| 2-08 | 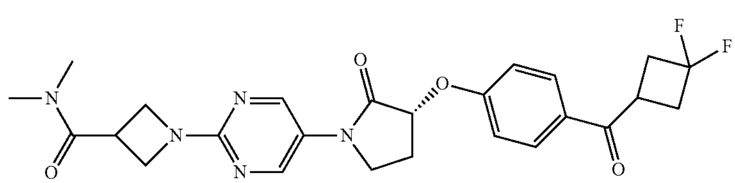 [SMILES: CN(C)C(=O)C1CN(c2ncc(N3CC[C@@H](Oc4ccc(C(=O)C5CC(F)(F)C5)cc4)C3=O)cn2)C1] | B | 1.57 | 500.3 |
| 2-09 | 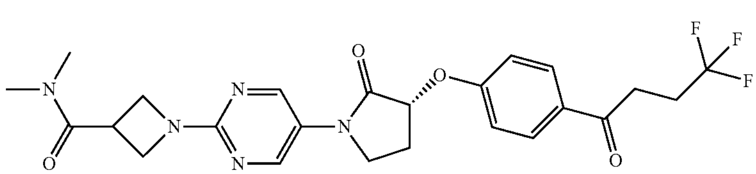 [SMILES: CN(C)C(=O)C1CN(c2ncc(N3CC[C@@H](Oc4ccc(C(=O)CCC(F)(F)F)cc4)C3=O)cn2)C1] | B | 1.60 | 506.3 |

TABLE 2-continued

| Comp. | Structure | LCMS Method | R$_t$ [min] | ESI$^+$ m/z [amu] |
|---|---|---|---|---|
| 2-10 | 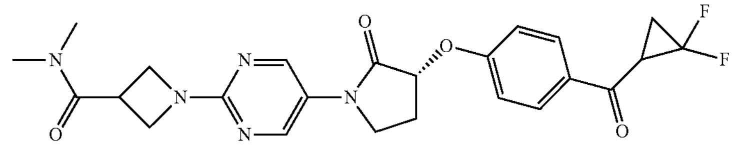 [SMILES: CN(C)C(=O)C1CN(c2ncc(N3CC[C@@H](Oc4ccc(C(=O)C5CC5(F)F)cc4)C3=O)cn2)C1] | B | 1.52 | 486.3 |
| 2-11 | 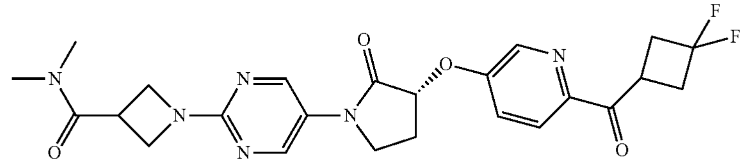 [SMILES: CN(C)C(=O)C1CN(c2ncc(N3CC[C@@H](Oc4ccc(C(=O)C5CC(F)(F)C5)nc4)C3=O)cn2)C1] | B | 1.54 | 501.3 |

Preparation of 1-[5-((S)-3-hydroxy-2-oxo-pyrrolidin-1-yl)-pyrimidin-2-yl]-azetidine-3-carboxylic acid dimethylamide Following Typical Procedure 1, 1-(5-bromo-pyrimidin-2-yl)-azetidine-3-carboxylic acid dimethylamide was reacted with (S)-3-hydroxy-pyrrolidin-2-one to provide 1-[5-((S)-3-hydroxy-2-oxo-pyrrolidin-1-yl)-pyrimidin-2-yl]-azetidine-3-carboxylic acid dimethylamide. MS ESI$^+$: m/z=306 [M+H]$^+$.

Preparation of Phenols/Hydroxy-pyridines 6-(5-Methyl-thiazol-2-yl)-pyridin-3-ol

A solution of 2-(5-(4-methoxybenzyloxy)pyridin-2-yl)-5-methylthiazole (2.0 g) in TFA (10 mL) was stirred at 80° C. for 2 hours. After the reaction was complete, the mixture was evaporated. The residue was purified by chromatography (silica gel, EA/PE 1:2 to EA) to provide 6-(5-methyl-thiazol-2-yl)-pyridin-3-ol. MS ESI$^+$: m/z=193 [M+H]$^+$.

2-(5-(4-Methoxybenzyloxy)pyridin-2-yl)-5-methylthiazole

A mixture was prepared from 2-bromo-5-(4-methoxybenzyloxy)pyridine (2.0 g), 5-methylthiazole (614 mg), Pd(P(t-Bu)$_3$)$_2$ (253 mg), Cs$_2$CO$_3$ (2.02 g) and DMF (10 mL). The system was evacuated and refilled with nitrogen three times. The mixture was stirred at 150° C. under N$_2$ atmosphere for 3 hours. After cooling, insoluble material was removed by filtration over Celite. To the resulting solution was added water (100 mL). The precipitate obtained was filtered off and washed with MeOH three times to provide 2-(5-(4-methoxybenzyloxy)pyridin-2-yl)-5-methylthiazole. MS ESI$^+$: m/z=313 [M+H]$^+$.

(4-Fluoro-phenyl)-(5-hydroxy-pyridin-2-yl)-methanone

To a solution of 2-bromo-5-triisopropylsilanyloxy-pyridine (6.5 g) in THF (30 mL) was added n-BuLi (7.9 mL, 2.5 M) at −70° C. The mixture was stirred for one hour at −78° C. A solution of 4-fluoro-N-methoxy-N-methyl-benzamide (3 g) in THF (20 mL) was added dropwise. The mixture was stirred overnight at RT. An aqueous solution of NH$_4$Cl (50 mL) and EA (50 mL) was added. The organic layer was separated, dried over Na$_2$SO$_4$ and concentrated under vacuum to provide (4-fluoro-phenyl)-(5-hydroxy-pyridin-2-yl)-methanone. MS ESI$^+$: m/z=218 [M+H]$^+$.

2-Bromo-5-triisopropylsilanyloxy-pyridine

To a solution of 6-bromo-pyridin-3-ol (25.0 g) and imidazole (11.9 g) in DMF (150 mL) under argon was slowly added chloro-triisopropyl-silane (33.9 g). After stirring for 2 hours, the mixture was partioned between MTBE (500 mL) and NaOH (10%, 300 mL). The organic layer was extracted with NaOH (10%, 300 mL×2), water (200 mL) and brine (200 mL), dried (Na$_2$SO$_4$), filtrated and concentrated to provide 2-bromo-5-triisopropylsilanyloxy-pyridine. MS ESI$^+$: m/z=330 [M+H]$^+$.

4-Fluoro-N-methoxy-N-methyl-benzamide

To a mixture containing O,N-dimethylhydroxylamine hydrochloride (6.0 g) and triethylamine (4.05 g) in DCM (50 mL) at 0° C. was added 4-fluorobenzoyl chloride (6.0 g) over 30 minutes. The ice-bath was removed and after stirring for an additional 30 minutes, the reaction mixture was poured into H$_2$O (100 mL) and extracted with EtOAc (50 mL×3). The organic extract was washed with brine and dried (MgSO$_4$). Removal of the solvent in vacuo provided 4-fluoro-N-methoxy-N-methyl-benzamide, which was used without further purification.

Similarly, (3,3-difluoro-cyclobutyl)-(5-hydroxy-pyridin-2-yl)-methanone was prepared from 2-bromo-5-triisopropylsilanyloxy-pyridine and 3,3-difluoro-cyclobutanecarboxylic acid methoxy-methyl-amide.

(3,3-Difluoro-cyclobutyl)-(4-hydroxy-phenyl)-methanone

A mixture of [4-(tert-butyl-dimethyl-silanyloxy)-phenyl]-(3,3-difluoro-cyclobutyl)-methanone (8.1 g) and TBAF*3H$_2$O (9.9 g) in THF (200 mL) was stirred at RT for 6 hours. The mixture was concentrated and purified by SGC (PE/EA=1:4) to provide (3,3-difluoro-cyclobutyl)-(4-hydroxy-phenyl)-methanone. MS ESI$^+$: m/z=213 [M+H]$^+$.

[4-(tert-Butyl-dimethyl-silanyloxy)-phenyl]-(3,3-difluoro-cyclobutyl)-methanone

To a solution of (4-bromo-phenoxy)-tert-butyl-dimethyl-silane (6.0 g) in THF (200 mL) was added a solution of t-BuLi (19.3 mL) dropwise at −78° C. The reaction mixture was stirred for 20 minutes at −78° C. and then a solution of 3,3-difluoro-cyclobutanecarboxylic acid methoxy-methyl-amide (3.7 g) in dry THF (5 mL) was added slowly. The reaction mixture was warmed to RT and stirred for 4 hours. The reaction mixture was poured into water (100 mL). The aqueous phase was extracted with EA (100 mL×2). The organic phase was washed with brine and dried over Na$_2$SO$_4$. After filtration, the solvent was removed under reduced pressure to provide [4-(tert-butyl-dimethyl-silanyloxy)-phenyl]-(3,3-difluoro-cyclobutyl)-methanone. MS ESI$^+$: m/z=327 [M+H]$^+$.

3,3-Difluoro-cyclobutanecarboxylic acid methoxy-methyl-amide

To a stirred solution of 3,3-difluoro-cyclobutanecarboxylic acid (2.5 g) in DCM (80 mL) was added CDI (6.7 g) at room temperature. The mixture was stirred for 1 hour at RT and then O,N-dimethylhydroxylamine hydrochloride (2.2 g) was added. The reaction mixture was stirred for 6 hours at RT. The reaction mixture was poured into water (100 mL) and then extracted with DCM (30 mL×3). The organic phase was washed with water (50 mL), HCl (1 N, 30 mL), saturated NaHCO$_3$ (30 mL) and dried over Na$_2$SO$_4$.

After filtration, the solvent was removed under reduced pressure to provide 3,3-difluoro-cyclobutanecarboxylic acid methoxy-methyl-amide. MS ESI$^+$: m/z=180 [M+H]$^+$.

Using generally the same synthetic steps as described for (3,3-difluoro-cyclobutyl)-(4-hydroxy-phenyl)-methanone, 4,4,4-trifluoro-1-(4-hydroxy-phenyl)-butan-1-one and (2,2-difluoro-cyclopropyl)-(4-hydroxy-phenyl)-methanone were prepared from 4,4,4-trifluoro-butyric acid and 2,2-difluoro-cyclopropanecarboxylic acid, respectively.

Preparation of Compounds of Table 3

Compound 3-01 (Typical Procedure 7)

A mixture of 1-{5-[(R)-3-(6-cyclopropylmethoxy-pyridin-3-yloxy)-2-oxo-pyrrolidin-1-yl]-pyrimidin-2-yl}-azetidine-3-carboxylic acid methyl ester (50 mg), LiOH (0.34 mL, 0.5 M in water) and THF/water (2/1 mL) was stirred for 2 hours. The reaction mixture was acidified with citric acid (final pH=5) and extracted with EA. The organic layer was dried over Na$_2$SO$_4$, and concentrated. Purification by preparative HPLC provided Compound 3-01.

Compounds 3-01 to 3-04 in Table 3 were obtained by saponification of the respective methyl ester.

TABLE 3

| Comp. | Structure | LCMS Method | R$_t$ [min] | ESI$^+$ m/z [amu] |
|---|---|---|---|---|
| 3-01 | 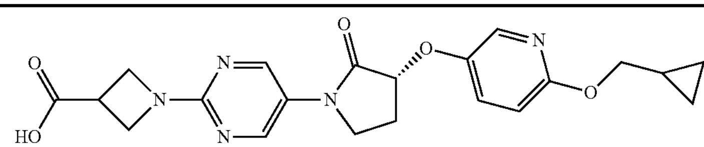 | B | 1.49 | 426.2 |
| 3-02 | 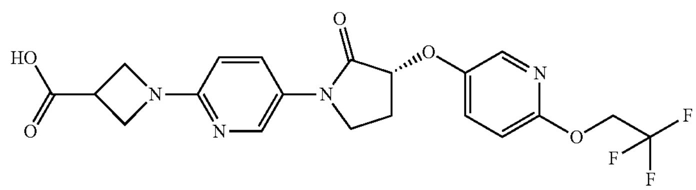 [SMILES: O=C(O)C1CN(c2ccc(N3CC[C@@H](Oc4ccc(OCC(F)(F)F)nc4)C3=O)cn2)C1] | D | 1.54 | 453.1 |
| 3-03 | 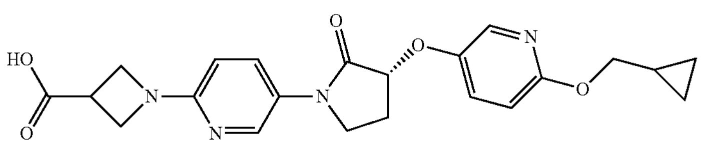 [SMILES: O=C(O)C1CN(c2ccc(N3CC[C@@H](Oc4ccc(OCC5CC5)nc4)C3=O)cn2)C1] | A | 1.39 | 425.1 |
| 3-04 | 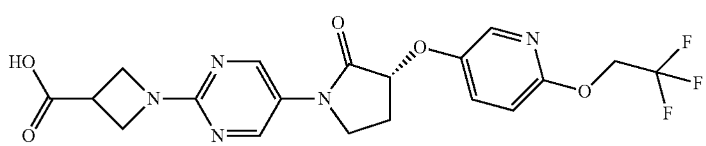 [SMILES: O=C(O)C1CN(c2ncc(N3CC[C@@H](Oc4ccc(OCC(F)(F)F)nc4)C3=O)cn2)C1] | B | 1.54 | 454.1 |

Preparation of Compounds of Table 4

Compound 4-01 (Typical Procedure 8)

To a mixture of 1-(5-{(R)-3-[6-(4-fluoro-phenoxy)-pyridin-3-yloxy]-2-oxo-pyrrolidin-1-yl}-pyrimidin-2-yl)-azetidine-3-carboxylic acid (60 mg), DIPEA (100 µL) and DMF (0.5 mL) was added EDCl (hydrochloride, 25 mg) and HOBt (17 mg). After 10 minutes methylamine (64 µL, 2 M in THF) was added. After 2 hours the mixture was separated by preparative HPLC to provide Compound 4-01.

The Compounds 4-01 to 4-27 in Table 4 were obtained by coupling of the appropriate activated carboxylic acid derivative with the respective amine.

TABLE 4

| Comp. | Structure | LCMS Method | $R_t$ [min] | ESI+ m/z [amu] |
|---|---|---|---|---|
| 4-01 | 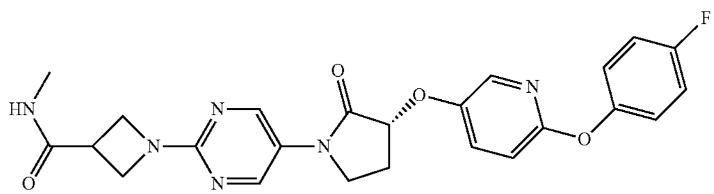 [SMILES: CNC(=O)C1CN(c2ncc(N3CC[C@@H](Oc4ccc(Oc5ccc(F)cc5)nc4)C3=O)cn2)C1] | B | 1.51 | 479.2 |
| 4-02 | 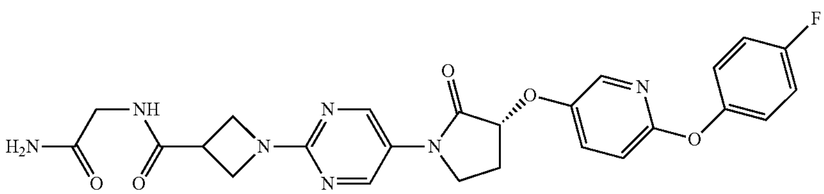 [SMILES: NC(=O)CNC(=O)C1CN(c2ncc(N3CC[C@@H](Oc4ccc(Oc5ccc(F)cc5)nc4)C3=O)cn2)C1] | B | 1.45 | 522.2 |
| 4-03 | 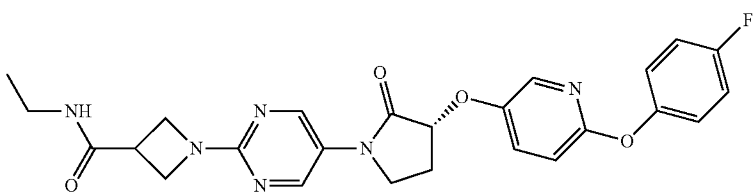 [SMILES: CCNC(=O)C1CN(c2ncc(N3CC[C@@H](Oc4ccc(Oc5ccc(F)cc5)nc4)C3=O)cn2)C1] | B | 1.55 | 493.2 |
| 4-04 | 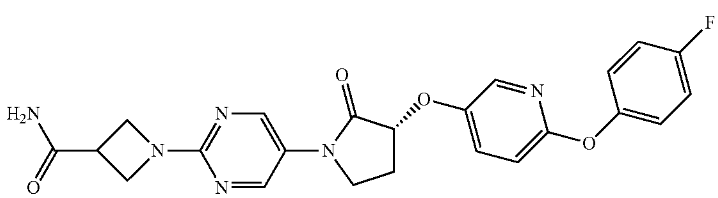 [SMILES: NC(=O)C1CN(c2ncc(N3CC[C@@H](Oc4ccc(Oc5ccc(F)cc5)nc4)C3=O)cn2)C1] | B | 1.48 | 465.2 |
| 4-05 | 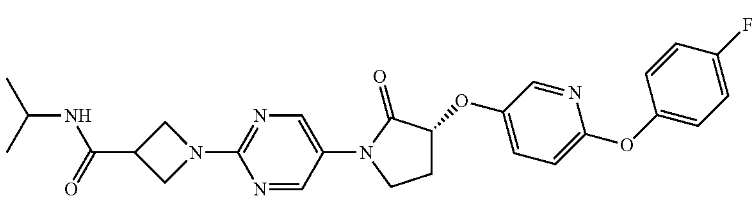 [SMILES: CC(C)NC(=O)C1CN(c2ncc(N3CC[C@@H](Oc4ccc(Oc5ccc(F)cc5)nc4)C3=O)cn2)C1] | B | 1.60 | 507.2 |
| 4-06 | 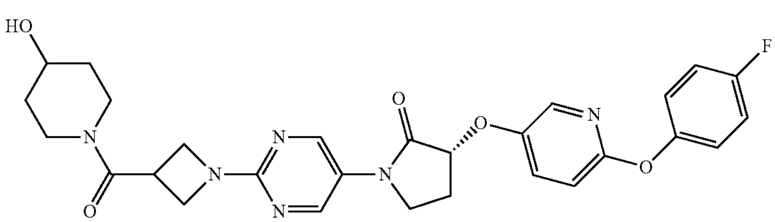 [SMILES: O=C(C1CN(c2ncc(N3CC[C@@H](Oc4ccc(Oc5ccc(F)cc5)nc4)C3=O)cn2)C1)N1CCC(O)CC1] | B | 1.52 | 549.2 |
| 4-07 | 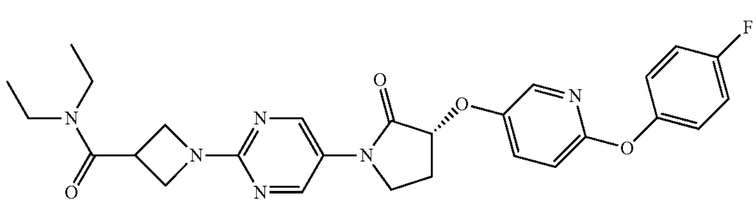 [SMILES: CCN(CC)C(=O)C1CN(c2ncc(N3CC[C@@H](Oc4ccc(Oc5ccc(F)cc5)nc4)C3=O)cn2)C1] | B | 1.67 | 521.2 |

TABLE 4-continued

| Comp. | Structure | LCMS Method | R$_t$ [min] | ESI$^+$ m/z [amu] |
|---|---|---|---|---|
| 4-08 | 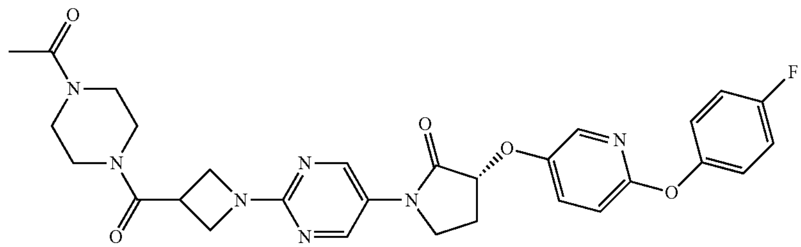 [SMILES: CC(=O)N1CCN(C(=O)C2CN(c3ncc(N4CC[C@@H](Oc5ccc(Oc6ccc(F)cc6)nc5)C4=O)cn3)C2)CC1] | B | 1.52 | 576.2 |
| 4-09 | 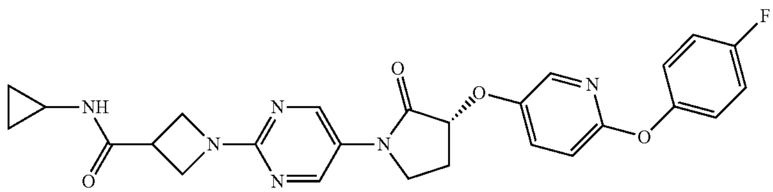 [SMILES: O=C(NC1CC1)C1CN(c2ncc(N3CC[C@@H](Oc4ccc(Oc5ccc(F)cc5)nc4)C3=O)cn2)C1] | B | 1.56 | 505.2 |
| 4-10 | 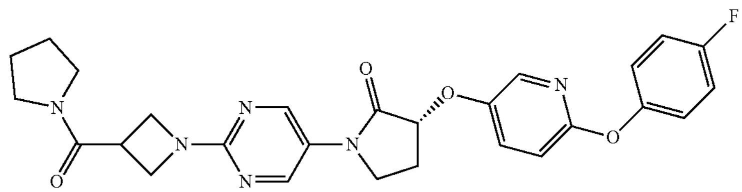 [SMILES: O=C(C1CN(c2ncc(N3CC[C@@H](Oc4ccc(Oc5ccc(F)cc5)nc4)C3=O)cn2)C1)N1CCCC1] | B | 1.61 | 519.2 |
| 4-11 | 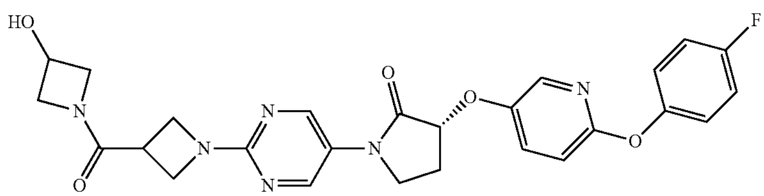 [SMILES: O=C(C1CN(c2ncc(N3CC[C@@H](Oc4ccc(Oc5ccc(F)cc5)nc4)C3=O)cn2)C1)N1CC(O)C1] | B | 1.48 | 521.2 |
| 4-12 | 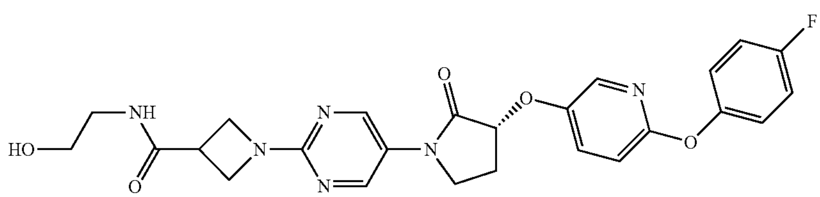 [SMILES: O=C(NCCO)C1CN(c2ncc(N3CC[C@@H](Oc4ccc(Oc5ccc(F)cc5)nc4)C3=O)cn2)C1] | B | 1.47 | 509.2 |
| 4-13 | 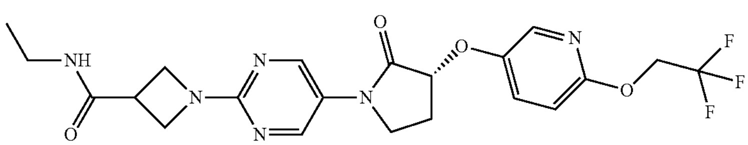 [SMILES: CCNC(=O)C1CN(c2ncc(N3CC[C@@H](Oc4ccc(OCC(F)(F)F)nc4)C3=O)cn2)C1] | B | 1.56 | 481.2 |
| 4-14 | 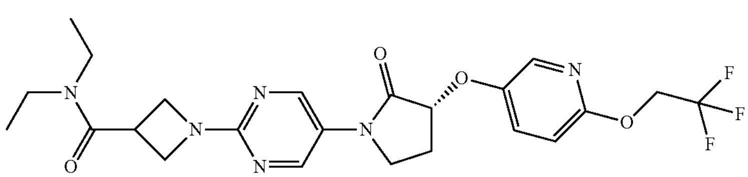 [SMILES: CCN(CC)C(=O)C1CN(c2ncc(N3CC[C@@H](Oc4ccc(OCC(F)(F)F)nc4)C3=O)cn2)C1] | B | 1.68 | 509.2 |
| 4-15 | 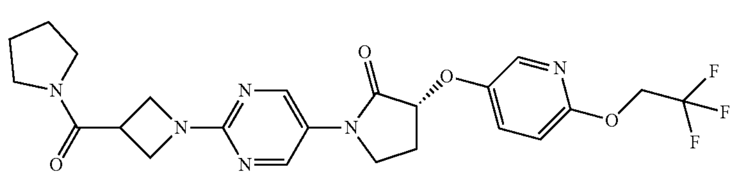 [SMILES: O=C(C1CN(c2ncc(N3CC[C@@H](Oc4ccc(OCC(F)(F)F)nc4)C3=O)cn2)C1)N1CCCC1] | B | 1.62 | 507.3 |

TABLE 4-continued

| Comp. | Structure | LCMS Method | $R_t$ [min] | ESI+ m/z [amu] |
|---|---|---|---|---|
| 4-16 | 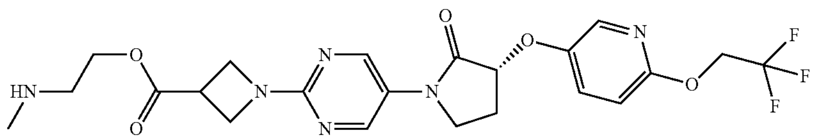 | B | 1.50 | 511.2 |
| 4-17 | 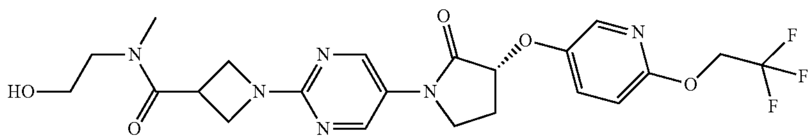 [SMILES: CN(CCO)C(=O)C1CN(c2ncc(N3CC[C@@H](Oc4ccc(OCC(F)(F)F)nc4)C3=O)cn2)C1] | B | 1.50 | 511.2 |
| 4-18 | 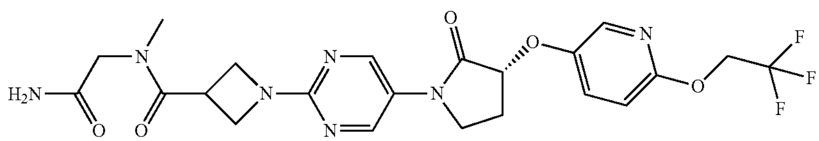 [SMILES: CN(CC(N)=O)C(=O)C1CN(c2ncc(N3CC[C@@H](Oc4ccc(OCC(F)(F)F)nc4)C3=O)cn2)C1] | B | 1.47 | 524.2 |
| 4-19 | 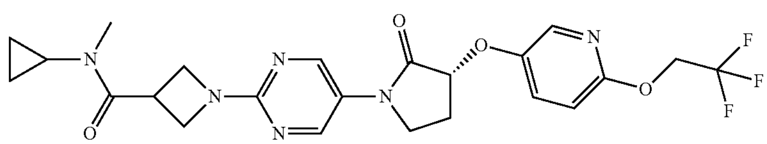 [SMILES: CN(C(=O)C1CN(c2ncc(N3CC[C@@H](Oc4ccc(OCC(F)(F)F)nc4)C3=O)cn2)C1)C1CC1] | B | 1.65 | 507.2 |
| 4-20 | 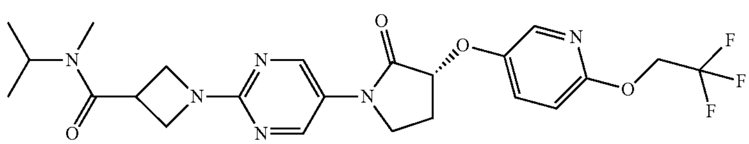 [SMILES: CC(C)N(C)C(=O)C1CN(c2ncc(N3CC[C@@H](Oc4ccc(OCC(F)(F)F)nc4)C3=O)cn2)C1] | B | 1.68 | 509.2 |
| 4-21 | 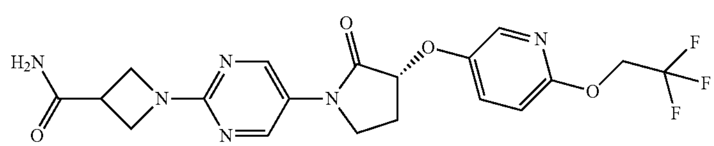 [SMILES: NC(=O)C1CN(c2ncc(N3CC[C@@H](Oc4ccc(OCC(F)(F)F)nc4)C3=O)cn2)C1] | B | 1.48 | 453.2 |
| 4-22 | 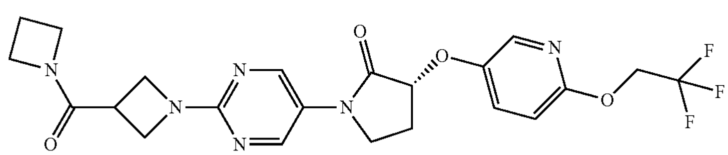 [SMILES: O=C(C1CN(c2ncc(N3CC[C@@H](Oc4ccc(OCC(F)(F)F)nc4)C3=O)cn2)C1)N1CCC1] | B | 1.57 | 493.3 |
| 4-23 | 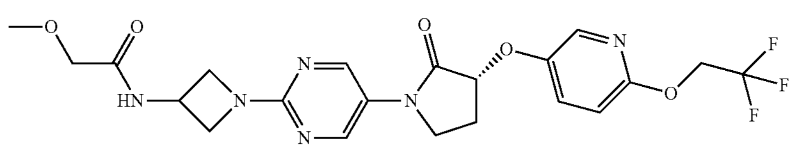 [SMILES: COCC(=O)NC1CN(c2ncc(N3CC[C@@H](Oc4ccc(OCC(F)(F)F)nc4)C3=O)cn2)C1] | B | 1.59 | 497.3 |
| 4-24 | 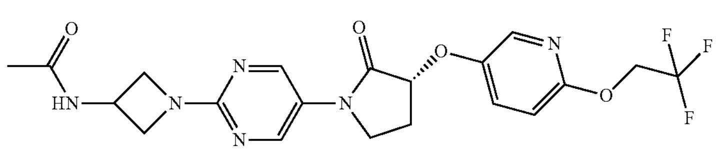 [SMILES: CC(=O)NC1CN(c2ncc(N3CC[C@@H](Oc4ccc(OCC(F)(F)F)nc4)C3=O)cn2)C1] | D | 1.70 | 467.2 |
| 4-25 | 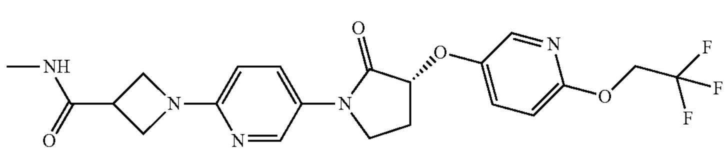 [SMILES: CNC(=O)C1CN(c2ccc(N3CC[C@@H](Oc4ccc(OCC(F)(F)F)nc4)C3=O)cn2)C1] | B | 1.37 | 466.2 |

TABLE 4-continued

| Comp. | Structure | LCMS Method | R$_t$ [min] | ESI$^+$ m/z [amu] |
|---|---|---|---|---|
| 4-26 | (structure) | B | 1.34 | 452.2 |
| 4-27 | (structure) | B | 1.56 | 487.3 |

1-(5-{(R)-3-[6-(4-Fluoro-phenoxy)-pyridin-3-yloxy]-2-oxo-pyrrolidin-1-yl}-pyrimidin-2-yl)-azetidine-3-carboxylic acid Following Typical Procedure 1, (R)-3-[6-(4-fluoro-phenoxy)-pyridin-3-yloxy]-pyrrolidin-2-one was reacted with 1-(5-bromo-pyrimidin-2-yl)-azetidine-3-carboxylic acid methyl ester to form 1-(5-{(R)-3-[6-(4-fluoro-phenoxy)-pyridin-3-yloxy]-2-oxo-pyrrolidin-1-yl}-pyrimidin-2-yl)-azetidine-3-carboxylic acid methyl ester, which was saponified under the reaction conditions to provide 1-(5-{(R)-3-[6-(4-fluoro-phenoxy)-pyridin-3-yloxy]-2-oxo-pyrrolidin-1-yl}-pyrimidin-2-yl)-azetidine-3-carboxylic acid. MS ESI$^+$: m/z=466 [M+H]$^+$.

Alternative Preparation of Compound 4-15

To a mixture of (1-(5-bromopyrimidin-2-yl)azetidin-3-yl)(pyrrolidin-1-yl)methanone (970 mg), (R)-3-((6-(2,2,2-trifluoroethoxy)pyridin-3-yl)oxy)pyrrolidin-2-one (861 mg) and 1,4-dioxane (10 mL) was added N,N'-dimethyl-ethane-1,2-diamine (5.0 mL). The mixture was purged for two minutes with a flow of argon and cesium carbonate (2.5 g) was added. The mixture was purged for 30 seconds with a flow of argon and CuI (500 mg) was added. The mixture was heated at 80° C. for one hour. After cooling to RT, the mixture was diluted with DCM (40 mL). Insoluble material was removed by filtration. The filtrate was reduced to a volume of 25 mL and subjected to SGC (DCM to 20% MeOH in EA) to provide Compound 4-15. 1H NMR (400 MHz, DMSO-d6) δ ppm: 8.65 (s, 2 H), 8.01 (d, J=2.9 Hz, 1 H), 7.62 (dd, J=9.0, 3.1 Hz, 1 H), 6.96 (d, J=8.9 Hz, 1 H), 5.22 (t, J=8.1 Hz, 1 H), 4.93 (q, J=9.1 Hz, 2 H), 4.20 (t, J=8.6 Hz, 2 H), 4.11 (dd, J=8.5, 6.2 Hz, 2 H), 3.77 (m, 3 H), 3.30 (m, 4H), 2.71 (m, 1 H), 2.14 (m, 1 H), 1.83 (m, 4 H).

(1-(5-Bromopyrimidin-2-yl)azetidin-3-yl)(pyrrolidin-1-yl)methanone

A mixture of methyl 1-(5-bromopyrimidin-2-yl)azetidine-3-carboxylate (1.0 g) and pyrrolidine (5.5 mL) was heated by microwave irradiation to 120° C. for three hours in a sealed vial. After cooling to RT, the mixture was concentrated. The residue was dissolved in EA and washed with HCl (0.1 M, 2×), NaHCO$_3$ (10% aq.) and brine. The organic layer was dried over Na$_2$SO$_4$, filtered and concentrated to provide (1-(5-bromopyrimidin-2-yl)azetidin-3-yl)(pyrrolidin-1-yl)methanone. MS ESI$^+$: m/z=311 [M+H]$^+$.

Alternative Preparation of Compound 4-22

To a mixture of azetidin-1-yl(1-(5-bromopyrimidin-2-yl)azetidin-3-yl)methanone (1.5 g), (R)-3-((6-(2,2,2-trifluoroethoxy)pyridin-3-yl)oxy)pyrrolidin-2-one (1.38 g) and 1,4-dioxane (15 mL) was added N,N'-dimethyl-ethane-1,2-diamine (7.5 mL). The mixture was purged for two minutes with a flow of argon and cesium carbonate (2.5 g) was added. The mixture was purged for 30 seconds with a flow of argon and CuI (500 mg) was added. The mixture was heated at 80° C. for 30 minutes. After cooling to RT, the mixture was diluted with DCM (40 mL). Insoluble material was removed by filtration. The filtrate was reduced to a volume of 25 mL and subjected to SGC (DCM to 20% MeOH in EA) to provide Compound 4-22. 1H NMR (400 MHz, DMSO-d6) δ ppm: 8.65 (s, 2 H), 8.01 (d, J=2.9 Hz, 1 H), 7.62 (dd, J=9.0, 3.1 Hz, 1 H), 6.96 (d, J=8.9 Hz, 1 H), 5.22 (t, J=8.1 Hz, 1 H), 4.93 (q, J=9.1 Hz, 2 H), 4.09 (m, 6 H), 3.83 (m, 4 H), 3.51 (m, 1 H), 2.71 (m, 1 H), 2.18 (m, 3 H).

Azetidin-1-yl(1-(5-bromopyrimidin-2-yl)azetidin-3-yl)methanone

A mixture of methyl 1-(5-bromopyrimidin-2-yl)azetidine-3-carboxylate (2.0 g), azetidine (1.0 mL) and THF (2 mL) was heated by microwave irradiation to 120° C. for 30 minutes in a sealed vial. The precipitate formed after cooling to RT was collected by filtration to provide azetidin-1-yl(1-(5-bromopyrimidin-2-yl)azetidin-3-yl)methanone. MS ESI$^+$: m/z=297 [M+H]$^+$.

Alternative Preparation of Compound 4-25

To a mixture of 1-(5-{(R)-2-oxo-3-[6-(2,2,2-trifluoroethoxy)-pyridin-3-yloxy]-pyrrolidin-1-yl}-pyrimidin-2-yl)-azetidine-3-carboxylic acid (100 mg), DIPEA (55 µL) and DMF (10 mL) was added EDCl (hydrochloride, 55 mg) and HOBt (44 mg) at 0° C. After 10 minutes, a mixture of methane amine (hydrochloride, 16 mg), DMF (5 mL) and DIPEA (110 µL) was added. After 2 hours at RT, the mixture was concentrated and the residue purified by SGC (heptane/ 20% MeOH in EA 1:4) to provide Compound 4-25. 1H NMR (400 MHz, DMSO-d6) δ ppm: 8.30 (d, J=2.6 Hz, 1 H), 8.00 (d, J=2.9 Hz, 1 H), 7.94 (br d, J=4.7 Hz, 1 H), 7.86 (dd, J=8.9, 2.7 Hz, 1 H), 7.62 (dd, J=9.1, 3.1 Hz, 1 H), 6.95 (d, J=9.1 Hz, 1 H), 6.44 (d, J=8.9 Hz, 1 H), 5.20 (t, J=8.1 Hz, 1 H), 4.92 (q, J=9.2 Hz, 2 H), 4.03 (t, J=8.1 Hz, 2 H), 3.92 (t, J=7.0 Hz, 2 H), 3.79 (m, 2 H), 3.48 (m, 1H), 2.60 (m, 4 H) 2.10 (m, 1 H).

Alternative Preparation of Compound 4-26

To a mixture of 1-(5-{(R)-2-oxo-3-[6-(2,2,2-trifluoro-ethoxy)-pyridin-3-yloxy]-pyrrolidin-1-yl}-pyridin-2-yl)-azetidine-3-carboxylic acid (300 mg), DIPEA (120 µL) and DMF (10 mL) was added EDCl (hydrochloride, 165 mg) and HOBt (132 mg) at 0° C. After 10 minutes, a mixture of ammonium chloride (39 mg), DMF (5 mL) and DIPEA (220 µL) was added. After 2 hours at RT, the mixture was concentrated and the residue purified by SGC (heptane/20% MeOH in EA 1:4) to provide Compound 4-26. 1H NMR (400 MHz, DMSO-d6) δ ppm: 8.31 (d, J=2.5 Hz, 1 H), 8.01 (d, J=3.1 Hz, 1 H), 7.87 (dd, J=8.9, 2.7 Hz, 1 H), 7.62 (dd, J=8.9, 3.1 Hz, 1 H), 7.46 (br s, 1 H), 6.99 (br s, 1 H), 6.96 (d, J=8.9 Hz, 1 H), 6.45 (d, J=9.1 Hz, 1 H), 5.21 (t, J=8.0 Hz, 1 H), 4.93 (q, J=9.1 Hz, 2 H), 4.04 (m, 2 H), 3.93 (m, 2 H), 3.80 (m, 2 H), 3.43 (m, 1H), 2.69 (m, 1 H), 2.11 (m, 1 H).

Preparation of Compounds of Table 5

Compounds 5-01 to 5-05 listed in Table 5 were obtained by various methods described in more detail below.

Compound 5-01

To a solution of (R)-1-[2-(3-hydroxy-azetidin-1-yl)-pyrimidin-5-yl]-3-[6-(2,2,2-trifluoro-ethoxy)-pyridin-3-yloxy]-pyrrolidin-2-one (70 mg) in DCM (1 mL) at 0° C. under argon was added trichloroacetyl isocyanate (38 mg). After stirring for 30 minutes, aluminum oxide (~200 mg) was added together with a drop of water. After one hour stirring at RT, the mixture was filtered and the filtrate concentrated. The residue was purified by preparative HPLC to provide Compound 5-01.

Compound 5-02

To a solution of (R)-1-[2-(3-hydroxy-azetidin-1-yl)-pyrimidin-5-yl]-3-[6-(2,2,2-trifluoro-ethoxy)-pyridin-3-yloxy]-pyrrolidin-2-one (90 mg) in THF (2 mL) at 0° C. under argon was added CDI (35 mg). After stirring for 30 minutes, dimethylamine (19 mg) was added. After stirring for four hours at RT, the mixture was concentrated. The residue was purified by preparative HPLC to provide Compound 5-02.

Compound 5-03

A mixture of (R)-1-[2-(3-amino-azetidin-1-yl)-pyrimidin-5-yl]-3-[6-(2,2,2-trifluoro-ethoxy)-pyridin-3-yloxy]-pyrro-

TABLE 5

| Comp. | Structure | LCMS Method | $R_t$ [min] | ESI+ m/z [amu] |
|---|---|---|---|---|
| 5-01 | 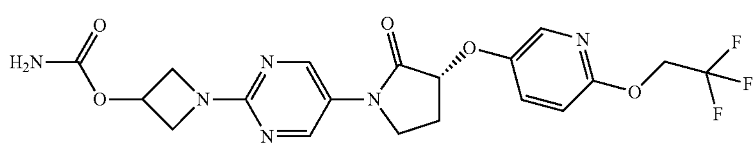 [SMILES: NC(=O)OC1CN(c2ncc(N3CC[C@@H](Oc4ccc(OCC(F)(F)F)nc4)C3=O)cn2)C1] | B | 1.54 | 469.2 |
| 5-02 | 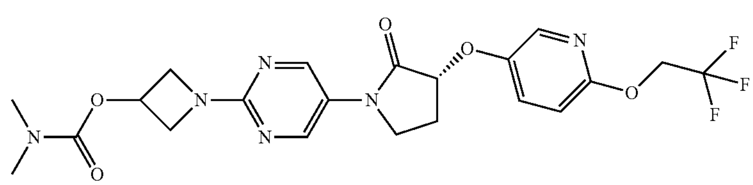 [SMILES: CN(C)C(=O)OC1CN(c2ncc(N3CC[C@@H](Oc4ccc(OCC(F)(F)F)nc4)C3=O)cn2)C1] | B | 1.67 | 497.4 |
| 5-03 | 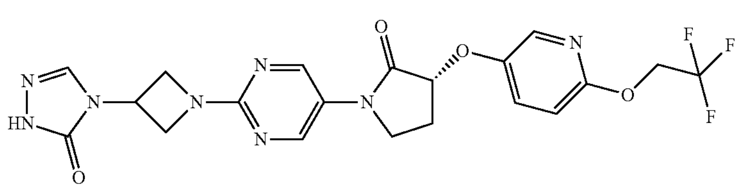 [SMILES: O=C1[C@H](Oc2ccc(OCC(F)(F)F)nc2)CCN1c1cnc(N2CC(n3cn[nH]c3=O)C2)nc1] | D | 1.66 | 493.2 |
| 5-04 | 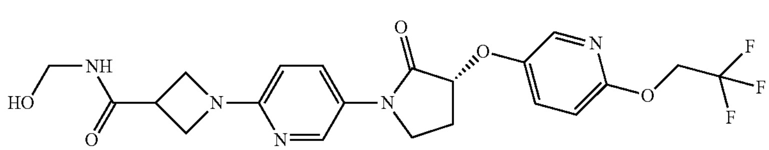 [SMILES: O=C(NCO)C1CN(c2ccc(N3CC[C@@H](Oc4ccc(OCC(F)(F)F)nc4)C3=O)cn2)C1] | B | 1.34 | 482.2 |
| 5-05 | | E | 1.00 | 496.3 | lidin-2-one (144 mg), TEA (34 mg) and DCM (1 mL) was added dropwise to a solution of triphosgene (33 mg) in DCM (1 mL) at 0° C. under argon. After stirring for 30 minutes at RT, the mixture was cooled to 0° C. and a mixture of formic acid hydrazide (31 mg) and TEA (34 mg) was added. After stirring at RT for 30 minutes, the reaction mixture was concentrated and the residue suspended in MeOH (2 mL). Solid KOH (100 mg) was added and the mixture heated for one hour at 100° C. The mixture was filtered and purified by preparative HPLC to provide Compound 5-03.

Compound 5-04

A mixture of (R)-1-(5-(2-oxo-3-((6-(2,2,2-trifluoroethoxy)pyridin-3-yl)oxy)pyrrolidin-1-yl)pyridin-2-yl)azetidine-3-carboxamide (100 mg), water (200 µL) and formaldehyde (37% aq., 17 µL) was treated with $K_2CO_3$ (3.1 mg) and DMF (0.5 mL). After stirring for 12 hours, the mixture was partioned between water and EA (10 mL×4). The combined organic layers were concentrated and the residue purified by SGC (heptane/20% MeOH in EA=1:4) to provide Compound 5-04.

Compound 5-05

A mixture of (N-methyl-1-[5-[(3R)-2-oxo-3-[[6-(2,2,2-trifluoroethoxy)-3-pyridyl]oxy]pyrrolidin-1-yl]-2-pyridyl]azetidine-3-carboxamide (130 mg), water (500 µL) and formaldehyde (37% aq., 21 µL) was treated with $K_2CO_3$ (3.9 mg) and DMF (0.5 mL). After two hours, more formaldehyde (37% aq., 21 µL), $K_2CO_3$ (3.9 mg) and DMF (0.5 mL) were added. After stirring for 12 hours, the mixture was concentrated and the residue purified by SGC (heptane/20% MeOH in EA=1:4) to provide Compound 5-05.

Pharmacological Utility

The biological activity of the compounds of the present disclosure may be demonstrated by known in vitro assays. Examples include in vitro cellular assays for recombinant and non-recombinant GPR119 as described in the following.

Functional Cellular Assays Measuring GPR119-mediated cAMP Release

Compounds of the present disclosure, which are agonists of GPR119, were characterized by functional assays measuring the cAMP response of HEK-293 cell lines stably expressing recombinant GPR119 from man, mouse or rat, or by using the hamster cell line HIT-T15 expressing GPR119 endogenously. The cAMP content was determined using a kit based on homogenous time-resolved fluorescence (HTRF) from Cisbio Corp. (cat. no. 62AM4PEC). For preparation, cells were split into T175 culture flasks and grown to near confluency in medium (DMEM/10% FCS for HEK-293 cells, and F-12K medium/10% horse serum/2.5% FCS for HIT-T15 cells, respectively). Medium was then removed and cells washed with PBS lacking calcium and magnesium ions, followed by proteinase treatment with accutase (Sigma-Aldrich, cat. no. A6964). Detached cells were washed and resuspended in assay buffer (1×HBSS; 20 mM HEPES, 0.1% BSA, 2 mM IBMX) and cellular density determined. They were then diluted to 400000 cells/mL and 25 µL-aliquots dispensed to the wells of 96-well plates. For measurement, 25 µL of test compound in assay buffer was added and incubated for 30 minutes at room temperature. After addition of HTRF reagents diluted in lysis buffer, the plates were incubated for 1 hour, followed by measuring the fluorescence ratio at 665 vs. 620 nm. Potency of the agonists was quantified by determining the concentrations that caused 50% of the maximal response/activation ($EC_{50}$). See Table 6 for exemplary data obtained using the cell line expressing human GPR119.

Compounds of the present disclosure show $EC_{50}$ values typically in the range of about 0.001 to 100 µM, preferably from about 0.001 to 10 µM, more preferably from about 0.001 to 1 µM and most preferably from about 0.001 to 0.3 µM.

TABLE 6

| Comp. | $EC_{50}$ [µM] |
| --- | --- |
| 1-01 | 0.057 |
| 1-02 | 0.206 |
| 1-03 | 0.255 |
| 1-04 | 0.070 |
| 1-05 | 0.061 |
| 1-06 | 0.170 |
| 1-07 | 0.030 |
| 1-08 | 0.092 |
| 1-09 | 0.064 |
| 1-10 | 0.044 |
| 1-11 | 0.421 |
| 1-12 | 0.050 |
| 1-13 | 0.257 |
| 1-14 | 2.070 |
| 1-15 | 0.248 |
| 1-16 | 0.058 |
| 1-17 | 0.122 |
| 1-18 | 0.343 |
| 1-19 | 0.180 |
| 1-20 | 1.970 |
| 1-21 | 0.991 |
| 1-22 | 0.872 |
| 1-23 | 0.189 |
| 1-24 | 0.335 |
| 1-25 | 0.292 |
| 1-26 | 0.448 |
| 1-27 | 2.210 |
| 1-28 | 0.290 |
| 1-29 | 0.016 |
| 1-30 | 0.334 |
| 1-31 | 0.129 |
| 1-32 | 0.195 |
| 1-33 | 0.664 |
| 1-34 | 0.369 |
| 1-35 | 0.181 |
| 1-36 | 0.158 |
| 1-37 | 0.071 |
| 1-38 | 9.840 |
| 1-39 | 0.179 |
| 1-40 | 1.820 |
| 1-41 | 0.221 |
| 1-42 | 0.157 |
| 1-43 | 0.116 |
| 1-44 | 0.138 |
| 1-45 | 0.203 |
| 1-46 | 0.411 |
| 1-47 | 1.630 |
| 1-48 | 0.752 |
| 1-49 | 1.360 |
| 1-50 | 0.321 |
| 1-51 | 0.093 |
| 1-52 | 0.012 |
| 1-53 | 0.351 |
| 1-54 | 1.660 |
| 2-01 | 0.218 |
| 2-02 | 0.137 |
| 2-03 | 0.324 |
| 2-04 | 0.926 |
| 2-05 | 0.116 |
| 2-06 | 0.145 |
| 2-07 | 0.128 |
| 2-08 | 0.223 |
| 2-09 | 0.123 |
| 2-10 | 0.213 |
| 2-11 | 0.470 |
| 3-01 | 4.920 |

TABLE 6-continued

| Comp. | EC$_{50}$ [μM] |
|---|---|
| 3-02 | 0.391 |
| 3-03 | 6.050 |
| 3-04 | 9.160 |
| 4-01 | 2.060 |
| 4-02 | 6.710 |
| 4-03 | 4.040 |
| 4-04 | 5.880 |
| 4-05 | 1.680 |
| 4-06 | 0.665 |
| 4-07 | 0.283 |
| 4-08 | 1.280 |
| 4-09 | 1.520 |
| 4-10 | 0.437 |
| 4-11 | 0.915 |
| 4-12 | 5.750 |
| 4-13 | 0.244 |
| 4-14 | 0.084 |
| 4-15 | 0.084 |
| 4-16 | 0.213 |
| 4-17 | 0.261 |
| 4-18 | 0.398 |
| 4-19 | 0.085 |
| 4-20 | 0.082 |
| 4-21 | 0.245 |
| 4-22 | 0.116 |
| 4-23 | 0.956 |
| 4-24 | 1.350 |
| 4-25 | 0.088 |
| 4-26 | 0.101 |
| 4-27 | 0.122 |
| 5-01 | 0.458 |
| 5-02 | 1.030 |
| 5-03 | 0.663 |
| 5-04 | 0.146 |
| 5-05 | 0.067 |

Based on the demonstrated ability of the compounds of the present disclosure to activate GPR119, said compounds may be useful for treatment of diseases and/or prevention of conditions which are modulated by GPR119.

Especially, the compounds of the present disclosure may be useful to treat GPR119-related diseases and/or prevent GPR119-mediated conditions in humans.

The compounds of the present disclosure are especially suitable for the treatment and/or prevention of:

1a) Disorders of fatty acid metabolism and glucose utilization disorders
1b) Disorders in which insulin resistance is involved
2) Diabetes mellitus, especially type 2 diabetes mellitus, including the prevention of the sequelae associated therewith. Particular aspects in this context are:
   a) Improvement of hyperglycemia
   b) Improvement of insulin resistance
   c) Improvement of glucose tolerance
   d) Protection of pancreatic beta cells
   e) Improvement of beta cell function
   f) Prevention of micro- and macrovascular disorders, such as
      a. Retinopathy
      b. Atherosclerosis
      c. Nephropathy and microalbuminuria
      d. Neuropathy
   g) Chronic low grade inflammation
3) Various other conditions which may be associated with the metabolic syndrome or the syndrome X, such as
   a) Increased abdominal girth
   b) Obesity
   c) Liver disorders
      a. Fatty liver
      b. Steatosis
      c. Steatohepatitis
      d. Cirrhosis
   d) Dyslipidemia (e.g. hypertriglyceridemia, hypercholesterolemia, hyperlipoproteinemia and/or low HDL)
   e) Insulin resistance
   f) Hypercoagulability
   g) Hyperuricemia
   h) Thromboses, hypercoagulable and prothrombotic states (arterial and venous)
   i) High blood pressure
   j) Endothelial dysfunction
   k) Heart failure, for example (but not limited to) following myocardial infarction, hypertensive heart disease or cardiomyopathy
4) Cardiovascular diseases, for example (but not limited to) myocardial infarction and stroke
5) Bone-related diseases and disorders characterized by redcued bone mass, such as:
   a) Osteoporosis
   b) Rheumatoid arthritis
   c) Osteoarthritis.

All publications, including patents, patent applications, and scientific articles mentioned in this specification, are herein incorporated by reference in their entirety for all purposes to the same extent as if each individual publication, including patent, patent application, or scientific article, were specifically and individually indicated to be incorporated by reference.

Although the foregoing disclosure has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the present disclosure.

The invention claimed is:

1. A compound of formula I

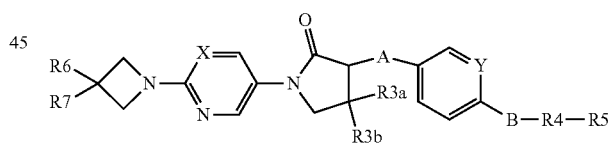

wherein:
X is N or C—R1;
Y is N or C—R2;
A is O or CH$_2$;
R1 is H, F or CN;
R2 is H or F;
R3a and R3b are independently H or (C$_1$-C$_6$)-alkyl;
B is a bond, O or C=O;
R4 is a bond or (CH$_2$)$_p$;
p is 1 or 2;
R5 is CF$_3$, (C$_3$-C$_8$)-cycloalkyl, phenyl or 5- or 6-membered heteroaryl ring;
   wherein the groups (C$_3$-C$_8$)-cycloalkyl, phenyl and 5- or 6-membered heteroaryl ring are optionally substituted with 1 to 3 groups selected from the group consisting of F and (C$_1$-C$_4$)-alkyl;
R6 is H or (C$_1$-C$_6$)-alkyl;

R7 is OH, NH₂, (CH₂)ₙ—COOR13, (CH₂)ₙ—CONR14R15, S(O)ₘR16, NHCO—R19, O(CO)NR20R21, COR22,

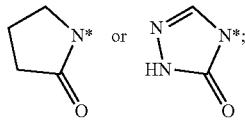

or R6 and R7, together with the carbon atom to which they are attached, form a ring of formula L, which is spiro connected to the azetidine moiety of formula I in the position marked by the asterix;

L is

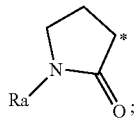

Ra is H or (C₁-C₆)-alkyl;
n is 0 or 1;
m is 0, 1 or 2;
R13 is H or (C₁-C₂)-alkyl, optionally substituted with NH₂, NH(C₁-C₂)-alkyl or N((C₁-C₂)-alkyl)₂;
R14 and R15 are independently H, (C₃-C₆)-cycloalkyl, (C₁-C₆)-alkyl or (C₁-C₆)-alkyl substituted with 1 to 3 groups selected from the group consisting of CONH₂ and OH;
R16 is (C₁-C₆)-alkyl;
R19 is (C₁-C₂)-alkylene-O—(C₁-C₂)-alkyl or (C₁-C₂)-alkyl;
R20 is H or (C₁-C₂)-alkyl;
R21 is H or (C₁-C₂)-alkyl; and
R22 is azetidinyl, pyrrolidinyl, piperidinyl or piperazinyl;
wherein the azetidinyl, pyrrolidinyl, piperidinyl or piperazinyl is optionally substituted with 1 to 3 groups selected from the group consisting of OH and COCH₃, or a stereoisomer or a physiologically acceptable salt thereof.

2. The compound of formula I according to claim 1, or a stereoisomer or a physiologically acceptable salt thereof, wherein the 3-position of the pyrrolidinone ring depicted in formula I has (R)-configuration.

3. The compound of formula I according to claim 1, or a stereoisomer or a physiologically acceptable salt thereof, wherein:
A is O.

4. The compound of formula I according to claim 1, or a stereoisomer or a physiologically acceptable salt thereof, wherein:
R7 is OH, NH₂ (CH₂)ₙ—COOR13, (CH₂)ₙ—CONR14R15, S(O)ₘR16, NHCO—R19, COR22,

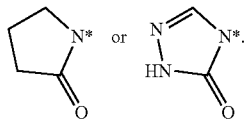

5. The compound of formula I according to claim 1, which is a compound of formula Ia

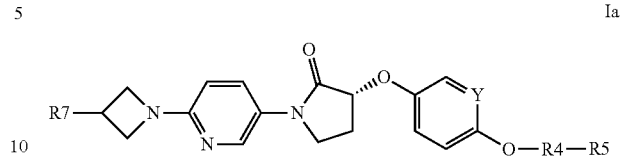

wherein:
R4 is (CH₂)ₚ;
p is 1 or 2;
R5 is CF₃ or cyclopropyl;
R7 is OH, COOR13, CONR14R15, S(O)ₘR16 or COR22;
m is 0, 1 or 2;
R13 is H or (C₁-C₂)-alkyl;
R14 and R15 are independently H, (C₃-C₆)-cycloalkyl, (C₁-C₆)-alkyl or (C₁-C₆)-alkyl substituted with 1 to 3 groups selected from the group consisting of CONH₂ and OH;
R16 is (C₁-C₆)-alkyl; and
R22 is azetidinyl, pyrrolidinyl, piperidinyl or piperazinyl;
wherein the azetidinyl, pyrrolidinyl, piperidinyl or piperazinyl is optionally substituted with 1 to 3 groups selected from the group consisting of OH and COCH₃, or a stereoisomer or a physiologically acceptable salt thereof.

6. The compound of formula Ia according to claim 5, or a physiologically acceptable salt thereof, wherein:
R4 is CH₂;
R7 is OH, COOR13, CONR14R15 or S(O)₂R16;
R13 is H or (C₁-C₂)-alkyl;
R14 and R15 are independently H, (C₃-C₆)-cycloalkyl, (C₁-C₆)-alkyl or (C₁-C₆)-alkyl substituted with 1 to 3 groups selected from the group consisting of CONH₂ and OH; and
R16 is (C₁-C₆)-alkyl.

7. The compound of formula Ia according to claim 6, or a physiologically acceptable salt thereof, wherein:
R4 is CH₂;
R5 is CF₃;
R7 CONR14R15 or S(O)₂R16;
R14 and R15 are independently H, (C₃-C₆)-cycloalkyl, (C₁-C₆)-alkyl or (C₁-C₆)-alkyl substituted with 1 to 3 groups selected from the group consisting of CONH₂ and OH; and
R16 is (C₁-C₆)-alkyl.

8. The compound of formula Ia according to claim 6, or a physiologically acceptable salt thereof, wherein:
R4 is CH₂;
R5 is CF₃;
R7 CONR14R15; and
R14 and R15 are independently H, (C₃-C₆)-cycloalkyl, (C₁-C₆)-alkyl or (C₁-C₆)-alkyl substituted with 1 to 3 groups selected from the group consisting of CONH₂ and OH.

9. The compound of formula I according to claim 1, wherein the compound is selected from the group consisting of compounds 1-01 to 1-54, 2-01 to 2-11, 3-01 to 3-04, 4-01 to 4-27 and 5-01 to 5-05, 1-01 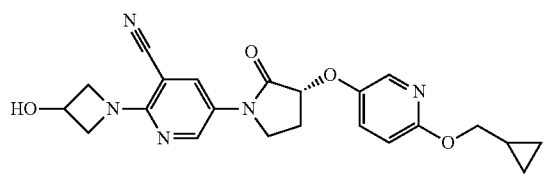
1-02 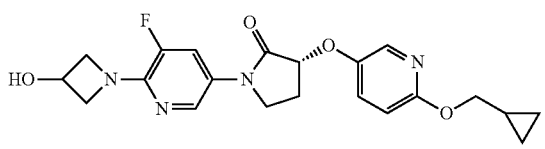
1-03 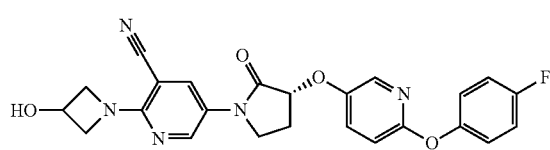
1-04 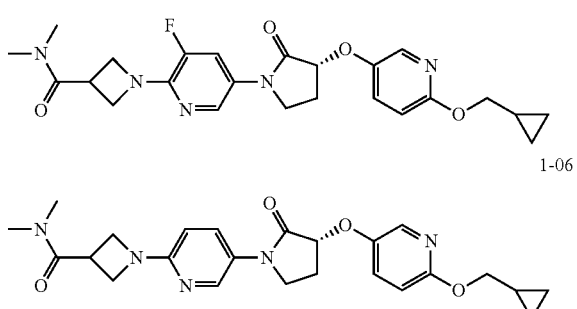
1-05 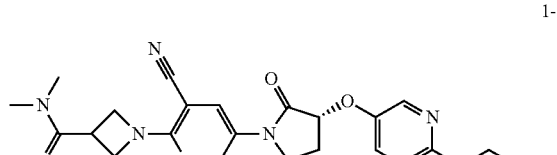
1-06
1-07 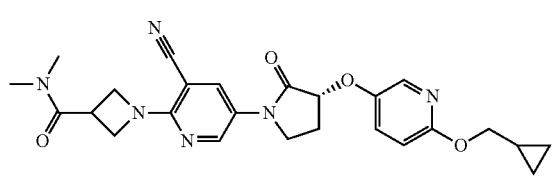
1-08 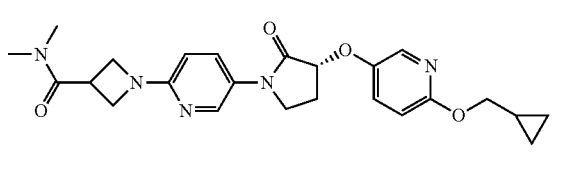
1-09 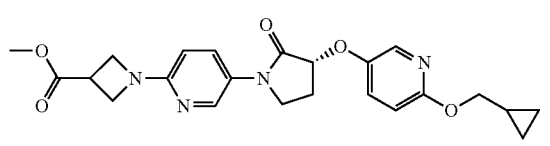
1-10 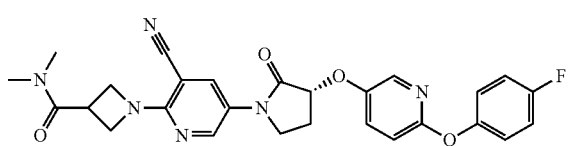
1-11 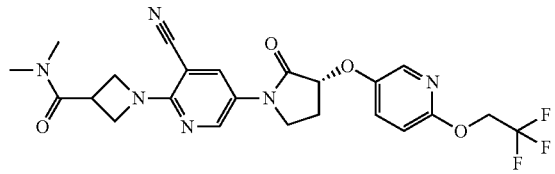
1-12 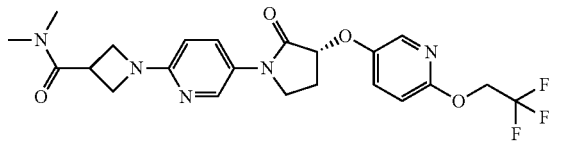
1-13 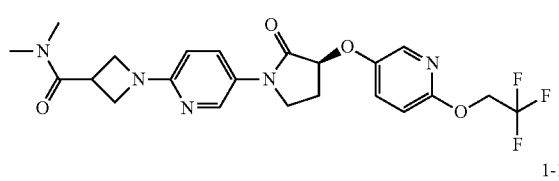
1-14 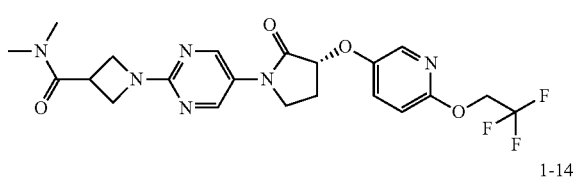
1-15 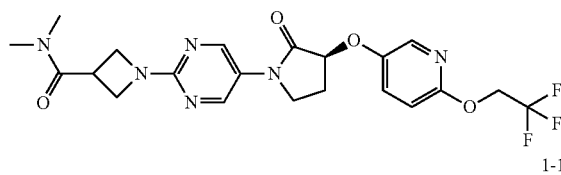
1-16 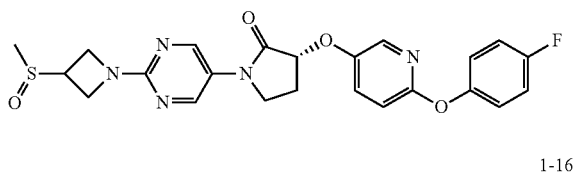
1-17 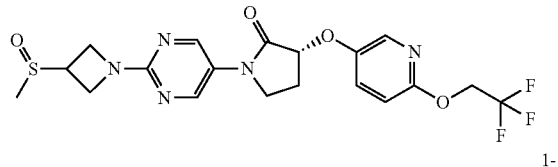
1-18 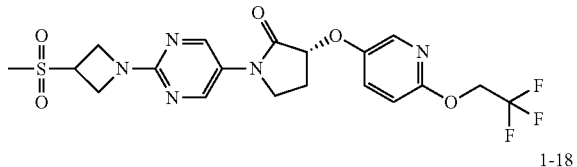
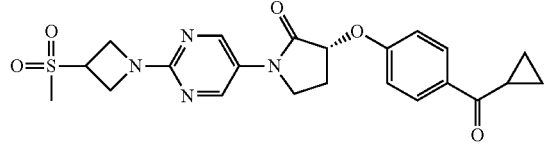

-continued
1-19
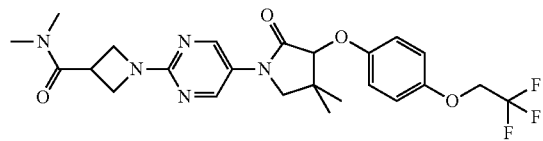
1-20
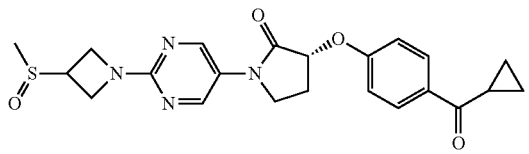
STEREOISOMER 1
1-21
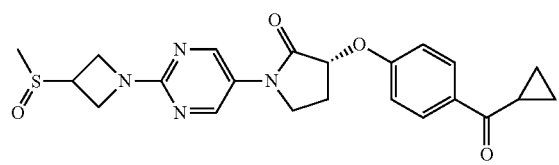
STEREOISOMER 2
1-22
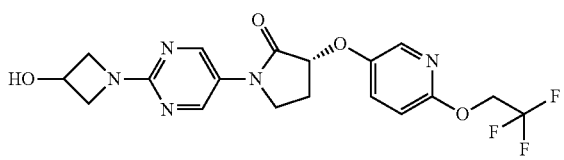
1-23
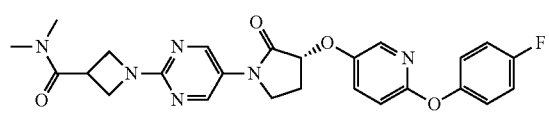
1-24
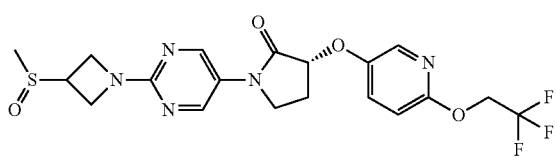
STEREOISOMER 1
1-25
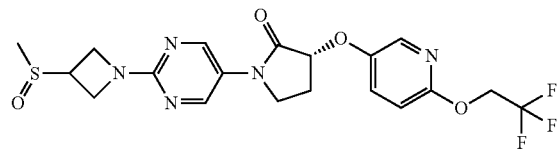
STEREOISOMER 2
1-26
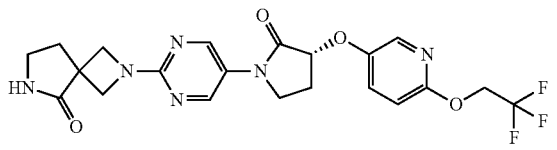
1-27
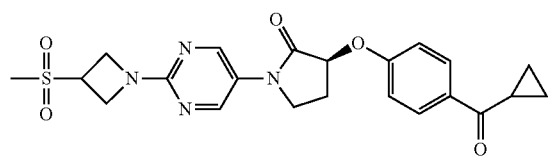
1-28
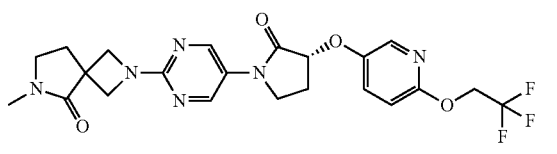
1-29
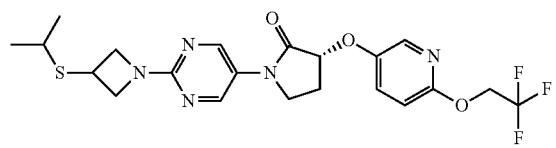
1-30
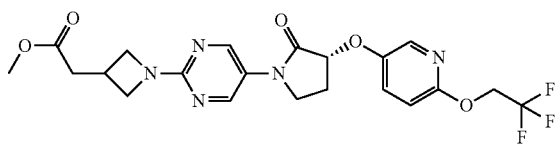
1-31
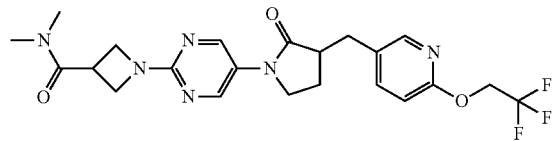
1-32
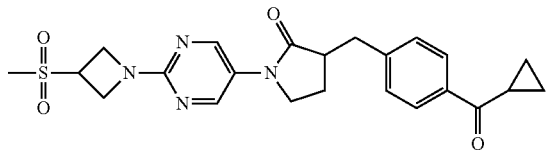
1-33
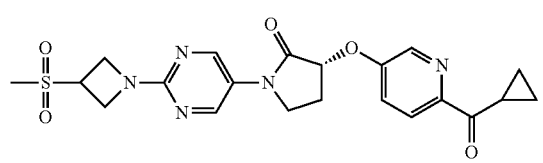
1-34
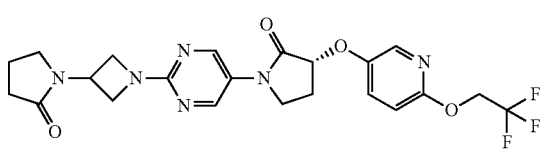

-continued
1-35
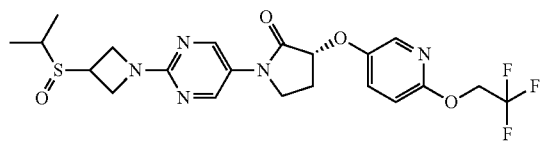
STEREOISOMER 1
1-36
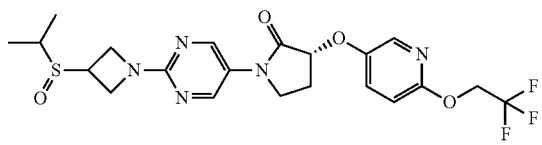
STEREOISOMER 2
1-37
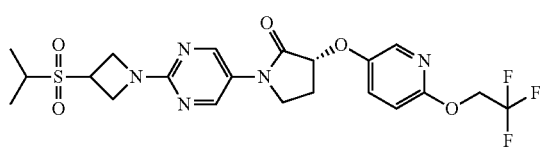
1-38
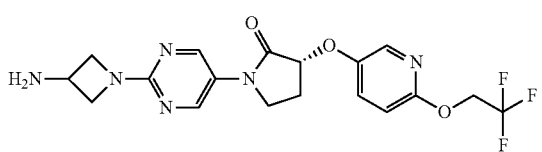
1-39
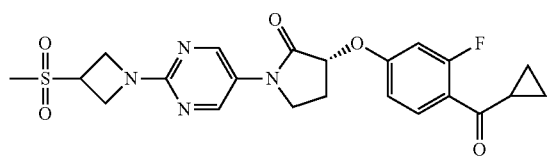
1-40
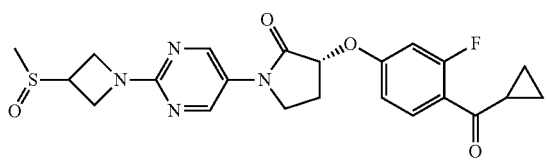
1-41
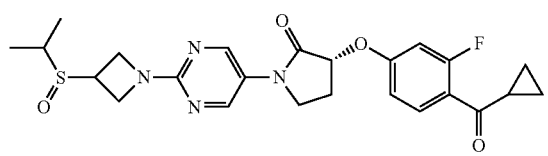
1-42
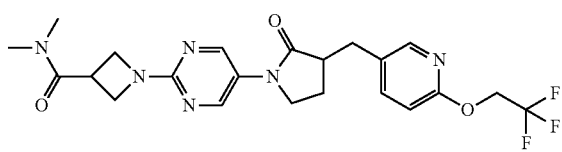
STEREOISOMER 1
1-43
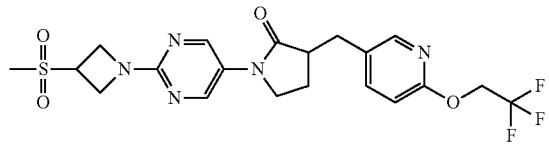
STEREOISOMER 1
1-44
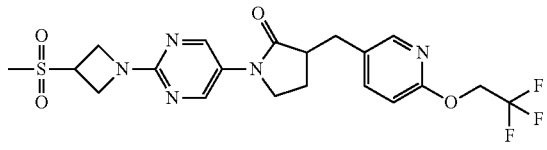
STEREOISOMER 2
1-45
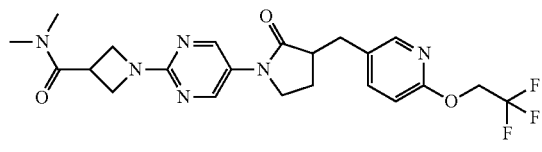
STEREOISOMER 2
1-46
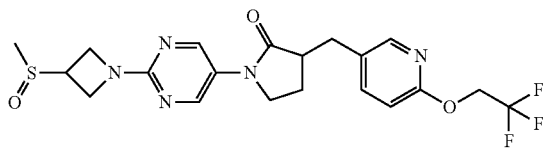
STEREOISOMER 1
1-47
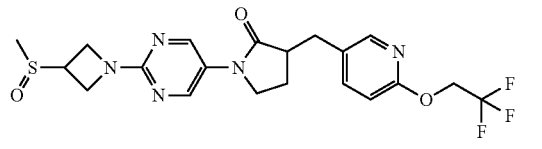
STEREOISOMER 2
1-48
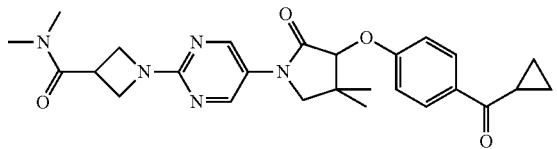
1-49
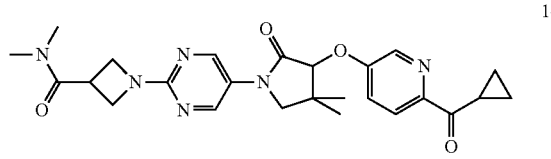
1-50
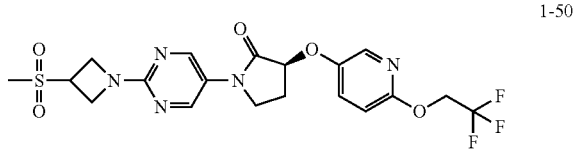

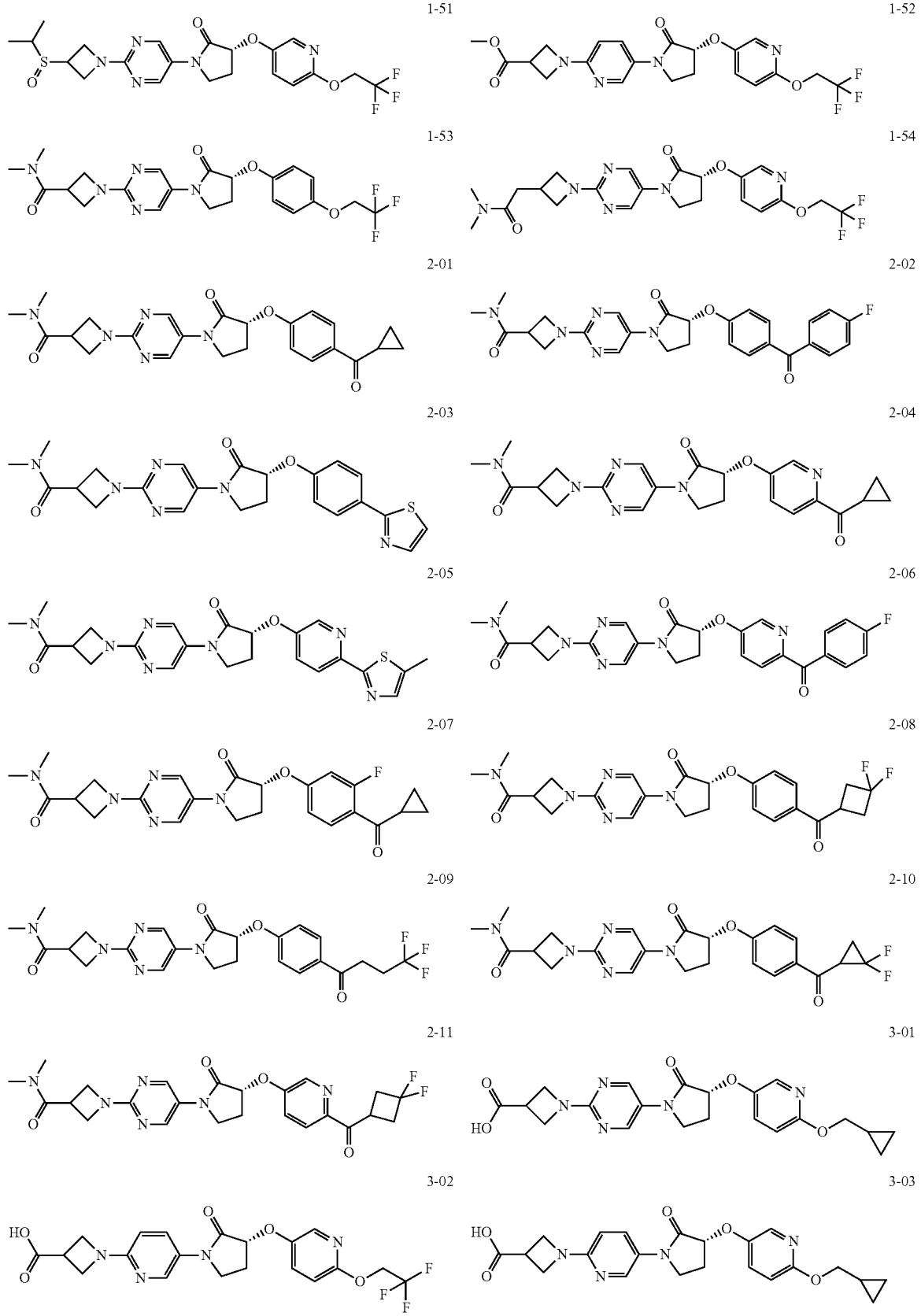

-continued
3-04
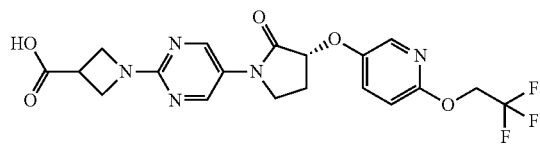
4-01
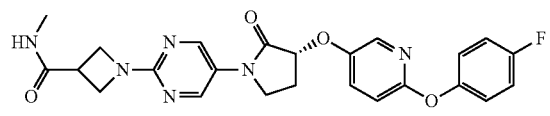
4-02
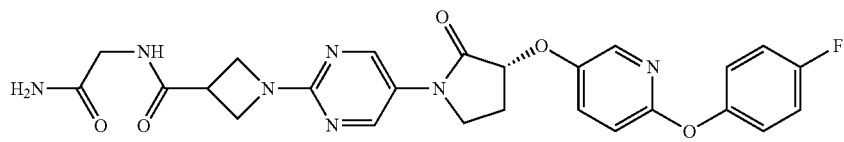
4-03
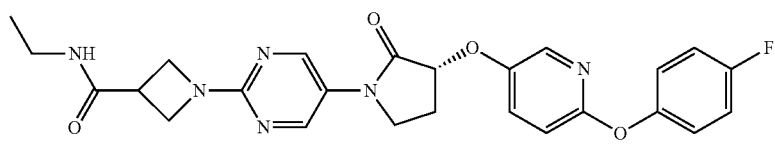
4-04
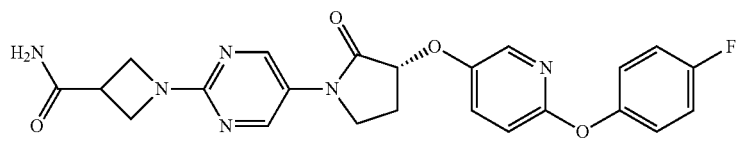
4-05
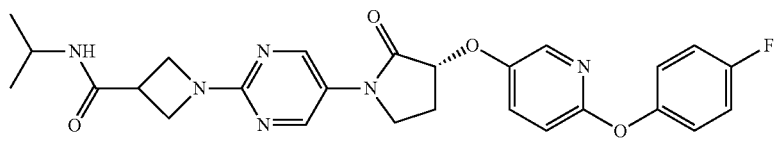
4-06
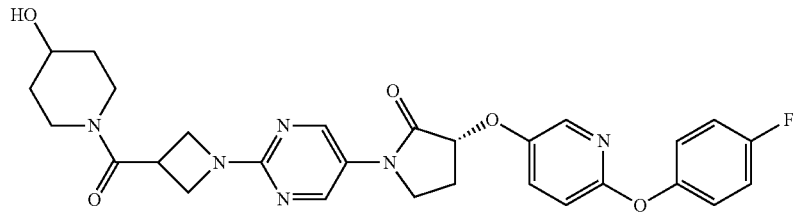
4-07
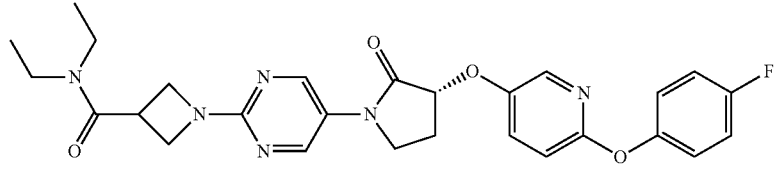
4-08
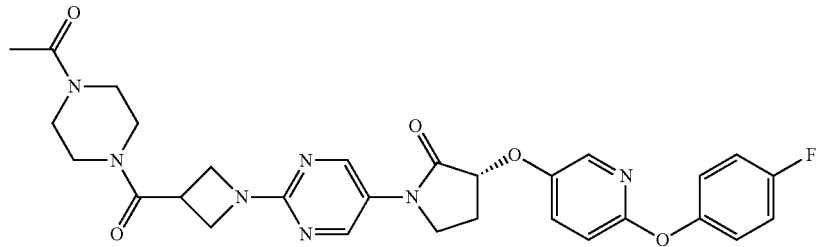
4-09
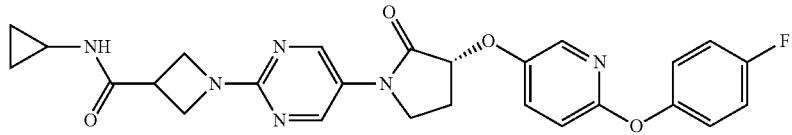

4-10
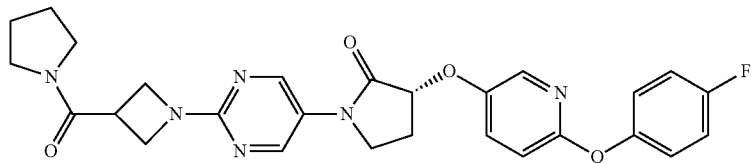
4-11
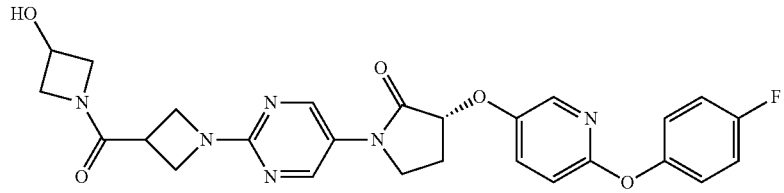
4-12
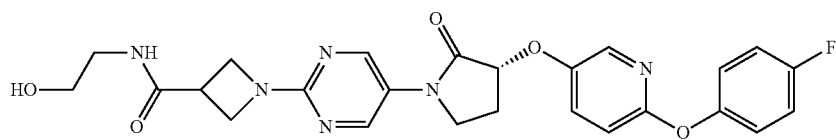
4-13 4-14
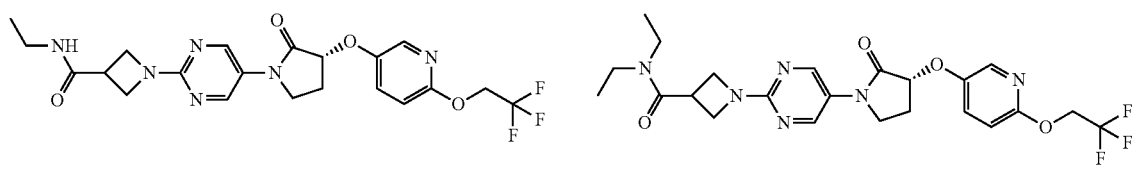
4-15
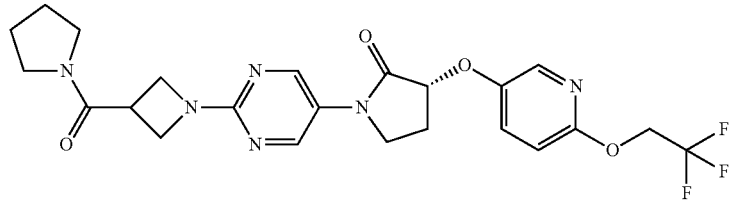
4-16
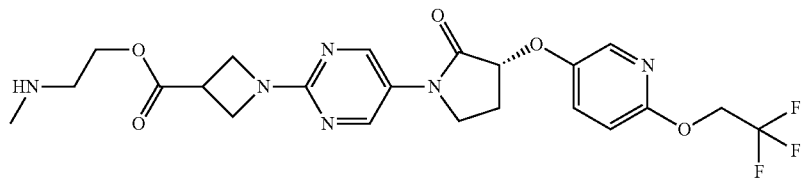
4-17
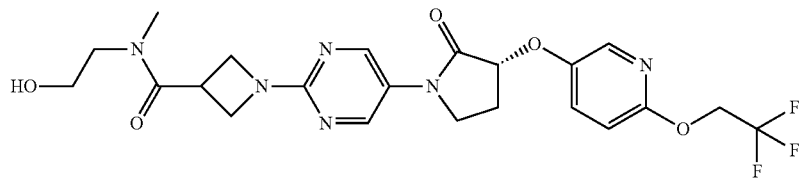
4-18
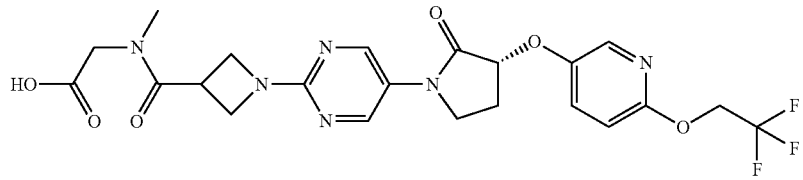

-continued
4-19
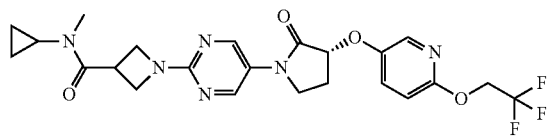
4-20
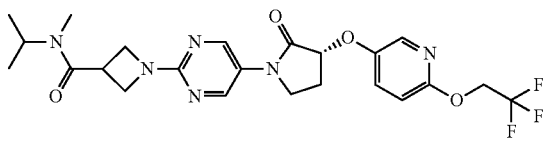
4-21
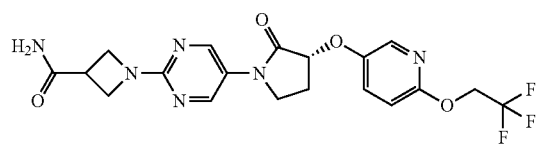
4-22
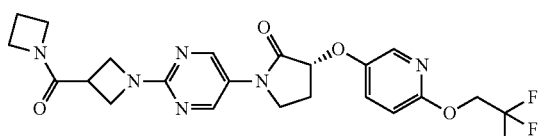
4-23
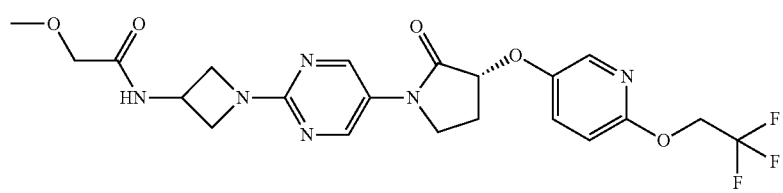
4-24
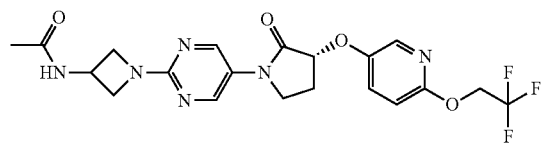
4-25
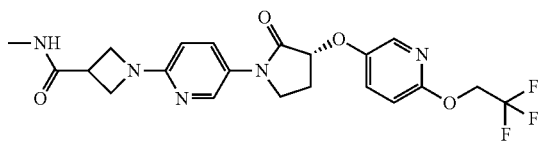
4-26
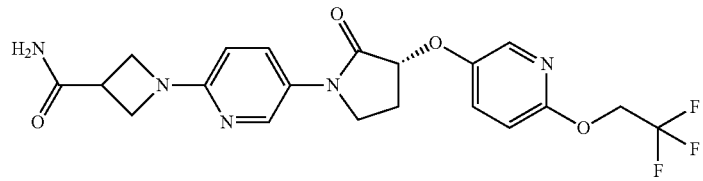
4-27
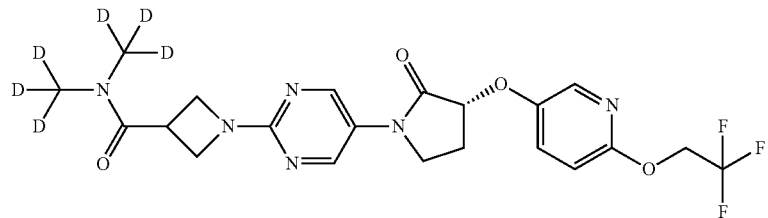
5-01
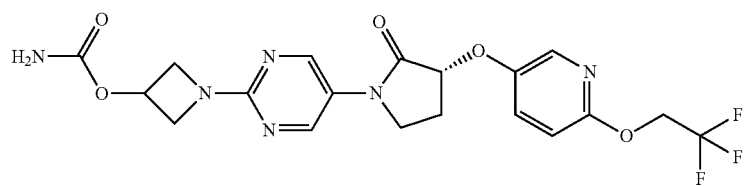
5-02
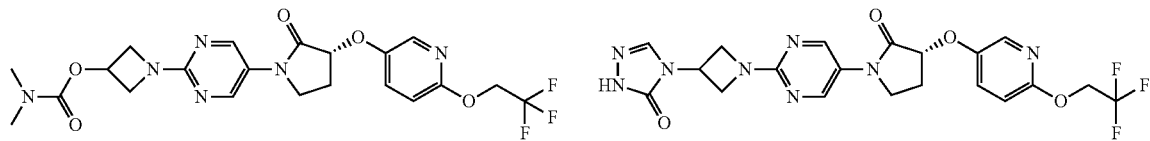
5-03
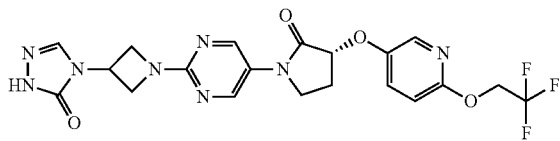

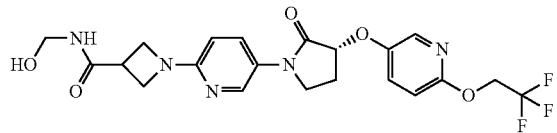
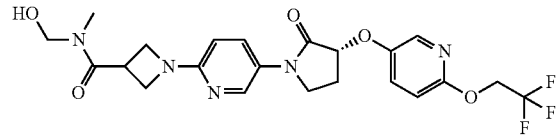

or a pharmaceutically acceptable salt thereof.

10. The compound according to claim 9, which is

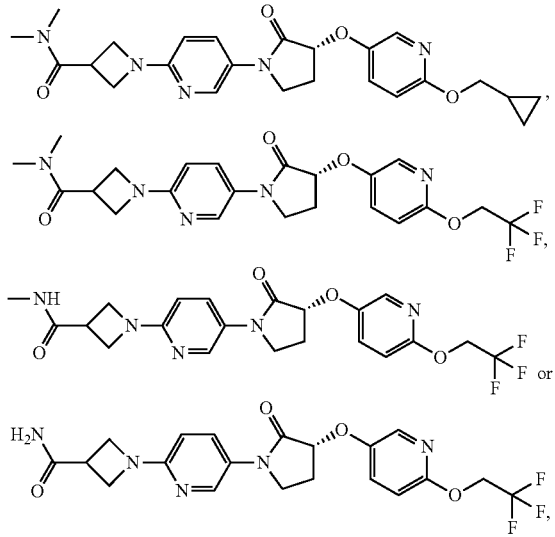

or a pharmaceutically acceptable salt thereof.

11. The compound according to claim 10, which is

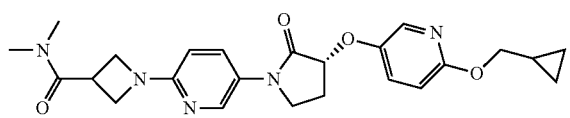 [SMILES: CN(C)C(=O)C1CN(c2ccc(N3CC[C@@H](Oc4ccc(OCC5CC5)nc4)C3=O)cn2)C1]

or a pharmaceutically acceptable salt thereof.

12. The compound according to claim 10, which is

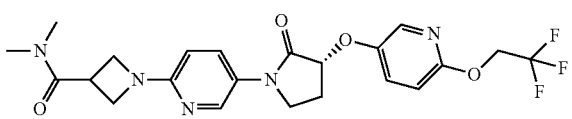 [SMILES: CN(C)C(=O)C1CN(c2ccc(N3CC[C@@H](Oc4ccc(OCC(F)(F)F)nc4)C3=O)cn2)C1]

or a pharmaceutically acceptable salt thereof.

13. The compound according to claim 10, which is

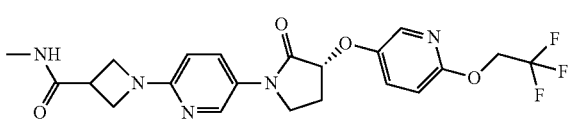 [SMILES: CNC(=O)C1CN(c2ccc(N3CC[C@@H](Oc4ccc(OCC(F)(F)F)nc4)C3=O)cn2)C1]

or a pharmaceutically acceptable salt thereof.

14. The compound according to claim 10, which is

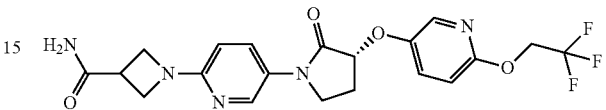

or a pharmaceutically acceptable salt thereof.

15. The compound according to claim 9, which is

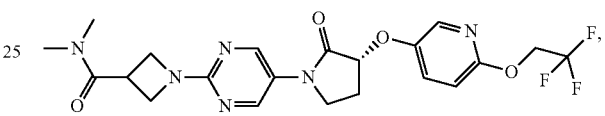
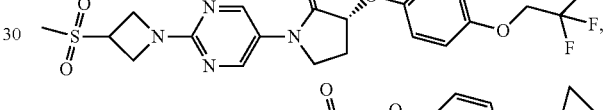
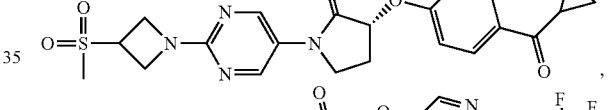
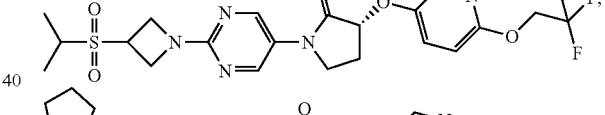
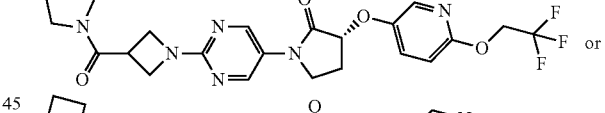
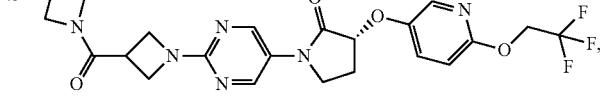

or a pharmaceutically acceptable salt thereof.

16. The compound of formula I according to claim 1, which is

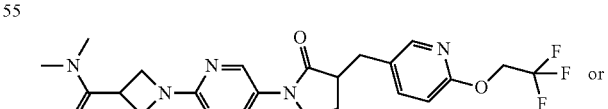
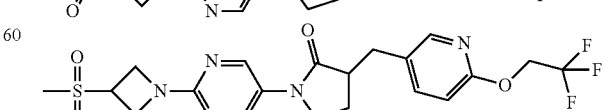

or a stereoisomer or a physiologically acceptable salt thereof.

17. A pharmaceutical composition or kit comprising an effective amount of at least one compound according to claim 1, or a stereoisomer or a physiologically acceptable salt thereof, and a pharmaceutically acceptable carrier.

18. The pharmaceutical composition or kit according to claim 17, further comprising one or more active ingredients selected from the group consisting of:

Insulin and insulin derivatives, GLP-1, GLP-1 analogues and GLP-1 receptor agonists, polymer bound GLP-1 and GLP-1 analogues, dual GLP-1/GIP agonists, dual GLP-1/glucagon receptor agonists, PYY3-36 or analogues thereof, pancreatic polypeptide or analogues thereof, glucagon receptor agonists or antagonists, GIP receptor agonists or antagonists, ghrelin antagonists or inverse agonists, xenin and analogues thereof, DDP-IV inhibitors, SGLT-2 inhibitors, dual SGLT-1/SGLT-2 inhibitors, biguanides, thiazolidinediones, PPAR agonists, PPAR modulators, sulfonylureas, meglitinides, alpha-glucosidase inhibitors, amylin and amylin analogues, GPR119 agonists, GPR40 agonists, GPR120 agonists, GPR142 agonists, TGR5 agonists, AMPK stimulants, AMPK activators, inhibitors of 11-beta-HSD, activators of glucokinase, inhibitors of DGAT, inhibitors of protein tyrosine phosphatase 1, inhibitors of glucose-6-phosphatase, inhibitors of fructose-1,6-bisphosphatase, inhibitors of glycogen phosphorylase, inhibitors of phosphoenol pyruvate carboxykinase, inhibitors of glycogen synthase kinase, inhibitors of pyruvate dehydrogenase kinase, CCR-2 antagonists, modulators of glucose transporter-4, somatostatin receptor 3 agonists, HMG-CoA-reductase inhibitors, fibrates, nicotinic acid and derivatives thereof, nicotinic acid receptor 1 agonists, ACAT inhibitors, cholesterol absorption inhibitors, bile acid-binding substances, IBAT inhibitors, MTP inhibitors, modulators of PCSK9, LDL receptor up-regulators (liver selective thyroid hormone receptor beta agonists), HDL-raising compounds, lipid metabolism modulators, PLA2 inhibitors, ApoA-I enhancers, cholesterol synthesis inhibitors, omega-3 fatty acids and derivatives thereof, active substances for the treatment of obesity, CB1 receptor antagonists, MCH-1 antagonists, MC4 receptor agonists and partial agonists, NPY5 or NPY2 antagonists, NPY4 agonists, beta-3 adrenergic receptor agonists, leptin or leptin mimetics, 5HT2c receptor agonists, lipase inhibitors, angiogenesis inhibitors, H3 antagonists, AgRP inhibitors, triple monoamine uptake inhibitors, MetAP2 inhibitors, antisense oligonucleotides against production of fibroblast growth factor receptor 4 or prohibitin targeting peptide-1, drugs for influencing high blood pressure, chronic heart failure or atherosclerosis, angiotensin II receptor antagonists, dual angiotensin receptor blockers (ARB), angiotensin converting enzyme (ACE) inhibitors, angiotensin converting enzyme 2 (ACE-2) activators, renin inhibitors, prorenin inhibitors, endothelin converting enzyme (ECE) inhibitors, endothelin receptor blockers, endothelin antagonists, diuretics, aldosterone antagonists, aldosterone synthase inhibitors, alpha-blockers, antagonists of the alpha-2 adrenergic receptor, beta-blockers, mixed alpha-/beta-blockers, calcium antagonists/calcium channel blockers (CBBs), dual mineralocorticoid/CCBs, centrally acting antihypertensives, inhibitors of neutral endopeptidase, aminopeptidase-A inhibitors, vasopeptide inhibitors, dual vasopeptide inhibitors, neprilysin-ACE inhibitors, neprilysin-ECE inhibitors, dual-acting angiotensin (AT) receptor-neprilysin inhibitors, dual AT1/endothelin-1 (ETA) antagonists, advanced glycation end-product breakers, recombinant renalase, blood pressure vaccines, anti-RAAS vaccines, AT1- or AT2-vaccines, modulators of genetic polymorphisms with antihypertensive response and thrombocyte aggregation inhibitors.

19. The pharmaceutical composition or kit according to claim 17, further comprising metformin.

20. The pharmaceutical composition or kit according to claim 17, further comprising at least one DPP-IV inhibitor.

21. The pharmaceutical composition or kit according to claim 20, wherein the at least one DPP-IV inhibitor is selected from the group consisting of alogliptin, linagliptin, saxagliptin, sitagliptin, anagliptin, teneligliptin, trelagliptin, vildagliptin, gemigliptin, omarigliptin, evogliptin and dutogliptin.

22. The pharmaceutical composition or kit according to claim 17, further comprising at least one SGLT-2 inhibitor or at least one dual SLGT-1/SGLT-2 inhibitor.

23. The pharmaceutical composition or kit according to claim 22, wherein the at least one SGLT-2 inhibitor is selected from the group consisting of canagliflozin, dapagliflozin, remogliflozin, remogliflozin etabonate, sergliflozin, empagliflozin, ipragliflozin, tofogliflozin, luseogliflozin and ertugliflozin.

24. The pharmaceutical composition or kit according to claim 22, wherein the at least one dual SGLT-1/SGLT-2 inhibitor is sotagliflozin.

25. The pharmaceutical composition or kit according to claim 17, further comprising at least one sulfonylurea.

26. The pharmaceutical composition or kit according to claim 25, wherein the at least one sulfonylurea is selected from the group consisting of tolbutamide, glibenclamide, glimepiride and glipizide.

27. The pharmaceutical composition or kit according to claim 17, further comprising ezetimibe.

28. The pharmaceutical composition or kit according to claim 17, further comprising at least one HMG-CoA reductase inhibitor.

29. The pharmaceutical composition or kit according to claim 28, wherein the at least one HMG-CoA reductase inhibitor is selected from the group consisting of simvastatin, atorvastatin, rosuvastatin, pravastatin, fluvastatin, pitavastatin, lovastatin, mevastatin, rivastatin and cerivastatin.

30. The pharmaceutical composition or kit according to claim 17, further comprising at least one PPAR agonist or PPAR modulator.

31. The pharmaceutical composition or kit according to claim 30, wherein the at least one PPAR agonist or PPAR modulator is selected from the group consisting of fenofibrate, pemafibrate, pioglitazone, rosiglitazone and lobeglitazone and saroglitazar.

32. The pharmaceutical composition or kit according to claim 17, further comprising acarbose.

33. A method for treatment of diabetes mellitus in a patient in need thereof, comprising administering to the patient an effective amount of the compound of formula I according to claim 1, or a stereoisomer or a physiologically acceptable salt thereof.

34. A method for treatment of obesity in a patient in need thereof, comprising administering to the patient an effective amount of the compound of formula I according to claim 1, or a stereoisomer or a physiologically acceptable salt thereof.

35. A method for treatment of dyslipidemia in a patient in need thereof, comprising administering to the patient an effective amount of the compound of formula I according to claim 1, or a stereoisomer or a physiologically acceptable salt thereof.

36. A method for treatment of hypertriglyceridemia in a patient in need thereof, comprising administering to the patient an effective amount of the compound of formula I according to claim 1, or a stereoisomer or a physiologically acceptable salt thereof.

37. A method for treating diabetes mellitus, obesity or dyslipidemia in a patient in need thereof, comprising administering to the patient an effective amount of at least one compound of formula I according to claim 1, or a stereoisomer or a physiologically acceptable salt thereof.

38. A method for treating diabetes mellitus, obesity, or dyslipidemia in a patient in need thereof, comprising administering to the patient an effective amount of at least one compound of formula I according to claim 1, or a stereoisomer or a physiologically acceptable salt thereof, and an effective amount of at least one other additional active ingredient useful for treating diabetes mellitus, obesity, dyslipidemia or high blood pressure.

39. The method of claim 38, wherein the effective amounts of the at least one compound of formula I, or a stereoisomer or a physiologically acceptable salt thereof, and of the at least one other additional active ingredient are adminstered to the patient simultaneously.

40. The method according to claim 38, wherein the effective amounts of the at least one compound of formula I, or a stereoisomer or a physiologically acceptable salt thereof, and of the at least one other additional active ingredient are adminstered to the patient sequentially.

41. The method according to claim 38, wherein the effective amounts of the at least one compound of formula I, or a stereoisomer or a physiologically acceptable salt thereof, and of two other additional active ingredients are adminstered to the patient simultaneously.

42. The pharmaceutical composition or kit according to claim 17, further comprising metformin and at least one other additional active ingredient.

43. The pharmaceutical composition or kit according to claim 42, comprising metformin and at least one DPP-IV inhibitor.

44. The pharmaceutical composition according to claim 42, comprising metformin and at least one SGLT-2 inhibitor or dual SGLT-1/SGLT-2 inhibitor.

* * * * *

UNITED STATES PATENT AND TRADEMARK OFFICE
CERTIFICATE OF CORRECTION

PATENT NO. : 10,392,366 B2
APPLICATION NO. : 15/899842
DATED : August 27, 2019
INVENTOR(S) : Lothar Schwink et al.

It is certified that error appears in the above-identified patent and that said Letters Patent is hereby corrected as shown below:

In the Claims

In Claim 1, Column 77, Lines 5-10: replace " 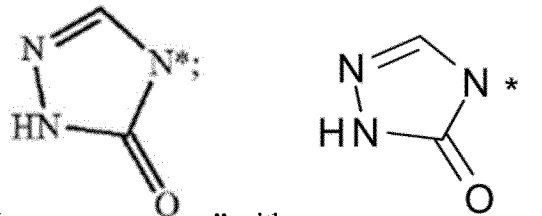 " with -- ;

In Claim 1, Column 77, Line 15: replace "asterix" with -- asterisk --;

In Claim 2, Column 77, Line 49: replace "has (R)-configuration" with -- has ($R$)-configuration --;

In Claim 4, Column 77, Lines 61-64: replace " 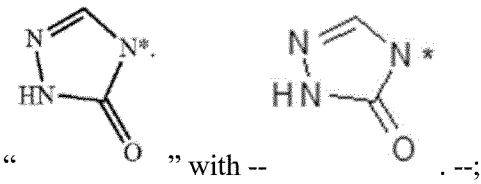 " with -- . --;

In Claim 5, Column 78, Line 8: replace the structure

" 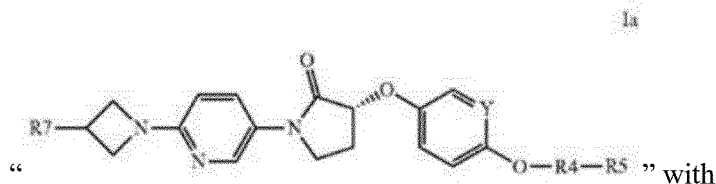 " with

Signed and Sealed this
Twenty-fourth Day of December, 2019

Andrei Iancu
*Director of the United States Patent and Trademark Office*

CERTIFICATE OF CORRECTION (continued)
U.S. Pat. No. 10,392,366 B2

Page 2 of 2

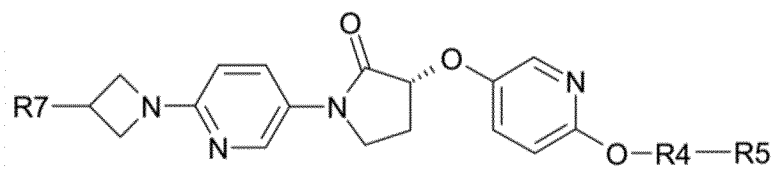

Ia

In Claim 7, Column 78, Line 47: replace "R7 CONR14R15" with -- R7 is CONR14R15 --;

In Claim 8, Column 78, Line 59: replace "R7 CONR14R15" with -- R7 is CONR14R15 --;

In Claim 9, Column 89, compound 4-18: replace the structure

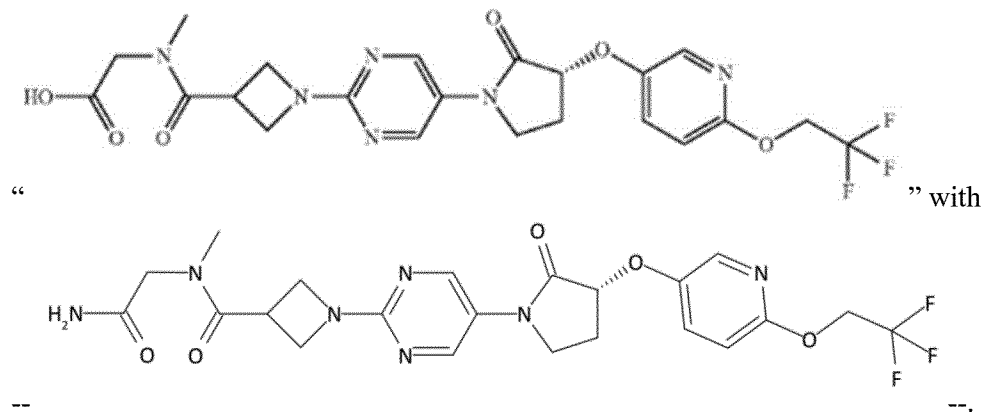

" with

" --.